US008715970B2

(12) United States Patent
Hauer et al.

(10) Patent No.: US 8,715,970 B2
(45) Date of Patent: May 6, 2014

(54) ENZYMATICALLY CATALYZED METHOD OF PREPARING MONO-ACYLATED POLYOLS

(75) Inventors: Bernhard Hauer, Fussgönheim (DE); Cecilia Kvarnström Branneby, Stockholm (SE); Karl Hult, Stockholm (SE); Anders Magnusson, Frankfurt (DE); Anders Hamberg, Bagarmossen (SE)

(73) Assignee: BASF SE (DE)

( * ) Notice: Subject to any disclaimer, the term of this patent is extended or adjusted under 35 U.S.C. 154(b) by 0 days.

(21) Appl. No.: 13/496,342

(22) PCT Filed: Sep. 16, 2010

(86) PCT No.: PCT/EP2010/063645
§ 371 (c)(1),
(2), (4) Date: Mar. 15, 2012

(87) PCT Pub. No.: WO2011/033039
PCT Pub. Date: Mar. 24, 2011

(65) Prior Publication Data
US 2012/0171738 A1 Jul. 5, 2012

Related U.S. Application Data
(60) Provisional application No. 61/245,298, filed on Sep. 24, 2009.

(30) Foreign Application Priority Data
Sep. 16, 2009 (EP) ..................................... 09170458

(51) Int. Cl.
C12P 7/62 (2006.01)
C12N 1/21 (2006.01)
(52) U.S. Cl.
USPC .......................................... 435/135; 435/198
(58) Field of Classification Search
None
See application file for complete search history.

(56) References Cited

U.S. PATENT DOCUMENTS

| | | | |
|---|---|---|---|
| 6,596,520 B1 | 7/2003 | Friedrich et al. | |
| 8,206,969 B2 | 6/2012 | Hauer et al. | |
| 2010/0151502 A1 | 6/2010 | Hauer et al. | |
| 2010/0273223 A1 | 10/2010 | Hauer et al. | |
| 2010/0291640 A1 | 11/2010 | Stuermer et al. | |
| 2010/0304448 A1 | 12/2010 | Sturmer et al. | |
| 2010/0311037 A1 | 12/2010 | Hauer et al. | |
| 2011/0137002 A1 | 6/2011 | Hauer et al. | |
| 2011/0171700 A1 | 7/2011 | Breuer et al. | |
| 2012/0070867 A1 | 3/2012 | Maurer et al. | |
| 2012/0123155 A1 | 5/2012 | Hauer et al. | |

FOREIGN PATENT DOCUMENTS

| | | |
|---|---|---|
| DE | 100193773 | 10/2001 |
| DE | 102006016023 A1 | 10/2007 |
| EP | 0407959 A2 | 1/1991 |
| EP | 1 069 183 A2 | 1/2001 |
| EP | 1149849 A1 | 10/2001 |
| WO | WO-2008065060 A2 | 6/2008 |

OTHER PUBLICATIONS

Hayes et al Biotecnol and Bioengr 1992, vol. 40, pp. 110-118.*
U.S. Appl. No. 13/497,985, Hauer et al.
Anderson, et al., "One Biocatalyst—Many Applications: The Use of *Candida antarctica* B-Lipase in Organic Synthesis", *Biocatalysis and Biotransformation*, vol. 16, pp. 181-204 (1998).
Branneby, et al., "Carbon-Carbon Bonds by Hydrolytic Enzymes", *J. Am. Chem. Soc.*, vol. 125, pp. 874-875 (2003).
Castillo, et al., "Lipase-Catalyzed Synthesis of Xylitol Monoesters: Solvent Engineering Approach", *Journal of Biotechnology*, vol. 102, pp. 251-259 (2003).
Chodorge, et al, "Rational Strategies for Directed Evolution of Biocatalysts—Application to *Candida antarctica* Lipase B (CALB)", *Adv. Synth. Catal.*, vol. 347, pp. 1022-1026 (2005).
Dubreucq, et al., "Optimization of Lipase-Catalyzed Sorbitol Monoester Synthesis in Organic Medium", *Journal of Surfactants and Detergents*, vol. 3, No. 3, pp. 327-333 (2000).
Hayes, et al., "Formation of Polyol-Fatty Acid Esters by Lipases in Reverse Micella Media", *Biotechnology and Bioengineering*, vol. 40, pp. 110-118 (1992).
Larsen, et al., "Expression of *Candida antarctica* Lipase B in *Pichia pastoris* and Various *Escherichia coli* Systems", *Protein Expression and Purification*, vol. 62, pp. 90-97 (2008).
Magnusson, et al al., "Creating Space for Large Secondary Alcohols by Rational Redesign of *Candida antarctica* Lipase B", *ChemBioChem*, vol. 6, pp. 1051-1056 (2005).
Magnusson, et al., "Creation of an Enantioselective Hydrolase by Engineered Substrate-Assisted Catalysis", *J. Am. Chem. Soc.*, vol. 123, pp. 4354-4355 (2001).
Martinelle, et al., "On the Interfacial Activation of *Candida antarctica* Lipase A and B as Compared with *Humicola lanuginosa* Lipase", *Biochemica et Biophysica Acta*, Vo. 1258, pp. 272-276 (1995).
Ollis, et al., "The α/β Hydrolase Fold", *Protein Engineering*, vol. 5, No. 3, pp. 197-211 (1992).
Patkar, et al., "Effect of Mutations in *Candida antarctica* B Lipase", *Chemistry and Physics of Lipids*, vol. 93, pp. 95-101 (1998).

(Continued)

*Primary Examiner* — Tekchand Saidha
*Assistant Examiner* — Md. Younus Meah
(74) *Attorney, Agent, or Firm* — Novak Druce Connolly Bove + Quigg LLP

(57) ABSTRACT

The present invention relates to a biocatalytic method of preparing a mono-acylated polyol catalyzed by triacylglycerol lipase mutants, as for example derived from *Candida antarctica* lipase B (CALB); a biocatalytic method of enantioselectively preparing an asymmetric mono-acylated polyol, catalyzed by the same enzyme mutants; as well as the use of a mutated triacylglycerol lipase in a method of preparing mono-acylated polyols. The invention also provides novel mutants, coding sequences thereof, and recombinant microorganisms carrying said coding sequences.

20 Claims, 14 Drawing Sheets

(56) References Cited

OTHER PUBLICATIONS

Rotticci, "Understanding and Engineering the Enantioselectivity of *Candida antarctica* Lipase B Towards Sec-Alcohols", *Royal Institute of Technology, Department of Chemistry, Organic Chemistry*, Stockholm (2000).

Rotticci, et al., "Improved Enantioselectivity of a Lipase by Rational Protein Engineering", *Chembiochem*, vol. 2, pp. 766-770 (2001).

Rotticci-Mulder, et al., "Expression in *Pichia pastoris* of *Candida antarctica* LipaseB and Lipase B Fused to a Cellulose-Binding Doman", *Protein Expression and Purification*, vol. 21, pp. 386-392 (2001).

Rotticci, et al., "An Active-Site Titration Method for Lipases", *Biochimica et Biophysica Acta*, vol. 1483, pp. 132-140 (2000).

Schmid, et al., "Lipases: Interfacial Enzymes with Attractive Applications", *Angew. Chem. Int. Ed.*, vol. 37, pp. 1608-1633 (1998).

Suen, et al., "Improved Activity and Thermostability of *Candida antarctica* Lipase B by DNA Family Shuffling", *Protein Engineering, Design & Selection*, vol. 17, No. 2, pp. 133-140 (2004).

Trodler, et al., "Rational Design of a New One-Step Purification Strategy for *Candida antarctica* Lipase B by Ion-Exchange Chromatography", *Journal of chromatography A.*, vol. 1179, pp. 161-167 (2008).

Uppenberg et al., The Sequence, Crystal Structure Determination and Refinement of Two Crystal Forms of Lipase B from *Candida antarctia, Structure*, vol. 15, No. 2, pp. 293-308 (1994).

Zhang et al., "Improving Tolerance of *Candida antarctica* Lipase B Towards Irreversible Thermal Inactivation Through Directed Evolution", *Protein Engineering*, vol. 16, No. 8, pp. 599-605 (2003).

* cited by examiner (A)

(B)

Substrate Butandiol in ethyl acetate

(A)

(B)

Substrate Glycol in ethyl acetate (A)   (B)

Product distribution, glycol in ethyl acetate (A)

(B)

Substrate glycol in ethyl acetate (A)

(B)

Substrate 2-methyl-1,3-propanediol and vinylbutyrate in MTBE (A)

(B)

Substrate 1,4-butanediol and vinylbutyrate in MTBE (A)

(B)

Competition experiments substrates 1,2-ethanediol (A) and 1,4-butanediol (B) in competition with 1-butanol. Ethyl acetate was used as acyl donor and solvent.

(A)

(B)

Competition experiments substrates 1,2-ethanediol (A) and 1,4-butanediol (B) in competition with 1-butanol. Vinyl butyrate was used as acyl donor and MTBE as solvent.

(A)

(B)

Converted 1,2-ethanediol per gram active enzyme expressed as functions of time. In A ethyl acetate was used as acyldonor and solvent. In B vinyl butyrate was used as acyl donor and MTBE as solvent.

ENZYMATICALLY CATALYZED METHOD OF PREPARING MONO-ACYLATED POLYOLS

RELATED APPLICATIONS

This application is a national stage application (under 35 U.S.C. §371) of PCT/EP2010/063645, filed Sep. 16, 2010, which claims benefit of European Application No. 09170458.5, filed Sep. 16, 2009, and U.S. Provisional Patent Application No. 61/245,298, filed Sep. 24, 2009.

SUBMISSION OF SEQUENCE LISTING

The Sequence Listing associated with this application is filed in electronic format via EFS-Web and hereby incorporated by reference into the specification in its entirety. The name of the text file containing the Sequence Listing is Sequence Listing_13111_00204_US. The size of the text file is 18 KB and the text file was created on Mar. 14, 2012.

The present invention relates to a biocatalytic method of preparing a mono-acylated polyol catalyzed by triacylglycerol lipase mutants, as for example derived from *Candida antarctica* lipase B (CALB); a biocatalytic method of enantioselectively preparing an asymmetric mono-acylated polyol, catalyzed by the same enzyme mutants; as well as the use of a mutated triacylglycerol lipase in a method of preparing mono-acylated polyols. The invention also provides novel mutants, coding sequences thereof, and recombinant microorganisms carrying said coding sequences.

BACKGROUND OF THE INVENTION

Triacylglycerol lipases (EC 3.1.1.3) are valued, efficient catalysts for a great variety of industrial uses, for example in the detergents industry, oil chemistry, the food industry and in the production of fine chemicals (Schmid R. D., Verger, R., *Angew. Chem. Int. Ausg.* 37: 1608-33 (1998)). Lipases are carboxylic ester hydrolases, which catalyze both the hydrolysis and the synthesis of triglycerides and other generally hydrophobic esters. All triacylglycerol lipases, whose three-dimensional crystal structure has been elucidated, belong to the α/β-hydrolase folding protein family, which have a similar overall architecture (Ollis D. L., Cheah, E., Cygler, M., Dijkstra, B., Frolow, F., Franken, S. M., Harel, M., Remingon, S. M., Silman, L., Schrag, J. D., *Protein Eng.* 5: 197-211 (1992)).

*Candida antarctica-lipase* B (also designated herein as CALB) is an efficient catalyst for many reactions and is used for example for stereoselective transformations and polyester synthesis (Anderson E. M., Larsson, K. M., Kirk, O., *Biocat. Biotransform.* 16: 181-204 (1998)) CALB has a solvent-accessible active center (Uppenberg J., Hansen, M. T., Patkar, S., Jones, A., *Structure* 2: 293-308 (1994)) and does not display interphase activation (Martinelle M., Holmquist M., Hult K., *Biochim. Biophys. Acta* 1258(3): 272-6 (1995)). The active center is a narrow funnel and for this reason CALB has a higher activity with respect to carboxylic acid esters, for example ethyl octanoate, than with respect to triglycerides (Martinelle 1995, supra). The fact that the activity of CALB in organic media is comparable to that in water, and in particular the high enantioselectivity of CALB for secondary alcohols make this enzyme one of the most important lipases currently in use in biotechnology.

Modification of CALB by random mutagenesis was described recently (Chodrorge M., Fourage L., Ullmann C., Duvivier V., Masson J. M., Lefèvre F., *Adv. Synth. Catal.* 347: 1022-1026 (2005). Several attempts to improve CALB for special applications through rational enzyme design have also been reported in the literature. Although some of these led to good results (Patkar S., Vind J., Kelstrup E., Christensen M. W., Svendsen A., Borch K., Kirk O., *Chem. Phys. Lipids* 93(1-2): 95-101 (1988); Rotticci D. "Understanding and Engineering the Enantioselectivity of *Candida antarctica* Lipase B towards sec-Alcohols". Stockholm: Royal institute of Technology 1-61 (2000)), the possibilities for rational enzyme design are still limited through insufficient understanding of the catalytic properties of the enzyme.

Zhang et al. report in Protein Engineering, vol. 16, no. 8 (2003) 599 on experiments aiming at an improvement of the tolerance of CALB to irreversible thermal inactivation. By applying directed evolution techniques single mutants containing the mutation V210I, V221D or A281E were prepared. The double mutant (V210I, A281E) and the triple mutant (V210I, A281E, V221D) as well as the single mutant A281E showed a significant improvement of their melting point ($T_m$) versus the $T_m$ of the wild-type enzyme.

Another approach for improving the activity and thermal stability of CALB was described by Suen et al. in Protein Engineering, Design & Selection, vol. 17, no. 2 (2004), 133. The technique of DNA family shuffling was used to create chimeric lipase B proteins derived from *Candida antarctica* and *Crytococcus tzukubaensis* as well as *Hyphozyma* sp. By high-throughput screening chimeras could be identified showing a higher activity towards the substrate 3-(3',4'-dichlorophenyl)glutarate, an improved half-life at 45° C. and an improved melting point ($T_m$).

Magnusson et al. describe in J. Am. Chem. Soc. 123 (2001), 4354 mono-mutants of CALB which differ in their enantioselectivity with respect to the hydrolysis of the two ethylesters ethyl-3-hydroxybutanoat and ethyl-2-hydroxypropanoat. In particular, the mono-mutants T40A and T40V are described therein. The preparation of monoacylated polyols is not taught or suggested.

Rotticci et al. disclose in ChemBiochem. 2 (2001), 766 experiments for improving the enantioselectivity of CALB towards different optically active secondary mono-alcohols. In particular, the single mutants S47A, S47N, S47H, T42N, T42D, T42H, T42V, W104H, as well as the double mutant (T42V, S47A) have been prepared via rational design and further investigated.

Branneby et al. disclose in J. Am. Chem. Soc. 125 (2003), 874 the single mutants S105A and S105G of CALB and their behaviour during aldol condensation reactions.

Magnussen et al. disclose in ChemBiochem. (2005) 1051 mutants of CALB having an enlarged substrate pocket, which mutants have the ability to utilize larger secondary mono-alcohols. In particular, the single mutants T42V, S47A, W104A, W104H, W104Q and the double mutant (T42V, S47A) were investigated.

Consequently, none of the above-mentioned documents teaches or suggests making use of CALB enzymes in methods for monoacylating polyols, in particular non-cyclic polyols.

The selective preparation of monoacylated polyols is considered to be difficult to achieve because of the fact that a monoacylated intermediate is expected to be quickly further esterified by the same enzyme, so that monoesters of polyols are expected to be merely intermediary formed during the course of the reaction and with the progress of the esterification reaction the proportion of monoesterified products is more and more diminished.

Therefore, there was a continued need for providing an enzymatically catalyzed method for selectively monoacylating polyols, such as diols, in particular non-cyclic diols. In particular, there was a need fur methods allowing the improved, preferential preparation of monoacylated polyols. An improvement in this respect may be characterized by an increased maximum yield of monoester, an improved molar ratio of monoester product to higher or fully esterified products, as for example diesters, an improved molar ratio of monoester product to total esterified products, and/or a higher monoester yields at higher degrees of conversion.

There was a further need for methods for enantioselectively preparing such monoacylated polyols, in the case of enzyme substrates having an asymmetric carbon atom.

SUMMARY OF THE INVENTION

The above-mentioned problems could, surprisingly, be solved by providing an enzymatically catalyzed method of preparing a mono-acylated polyol, which method makes use of mutated triacylglycerole lipase enzymes, like mutants of CALB, which were engineered to show improved selectivity, i.p. regioselectivity, allowing the preferential formation of monoacylated polyols.

The present invention allows performing polyol esterification reactions during the course of which the monoester product is produced in a significant molar excess over fully esterified products not only at low but, surprisingly, also at high degrees of polyol conversion. For example, a product distribution (defined as the ratio of monoester to the sum of all esterified products) of at least 90% are observed at degrees of conversion up to about 50 to 90%, thus allowing to proceed the reaction almost to completion, and isolating of the desired monoester product in high yields from the reaction mixture.

The invention will be further explained by making reference to the attached drawings.

DESCRIPTION OF DRAWINGS

FIG. 2 illustrates schematically the participation of amino acid residues in position 106 and 40 of the CALB oxianion hole in the stabilization of the oxianion intermediate as formed during transesterification reactions.

In B, vinyl butyrate is used as acyl donor and MTBE as solvent. The reaction rates differ between wild type and T40A CALB, showing that the wild type (rhombi) is a more efficient catalyst than the T40A (squares) variant. The difference in reaction rates is greater when ethyl acetate is used as acyl donor than for vinyl butyrate.

Figure 12:
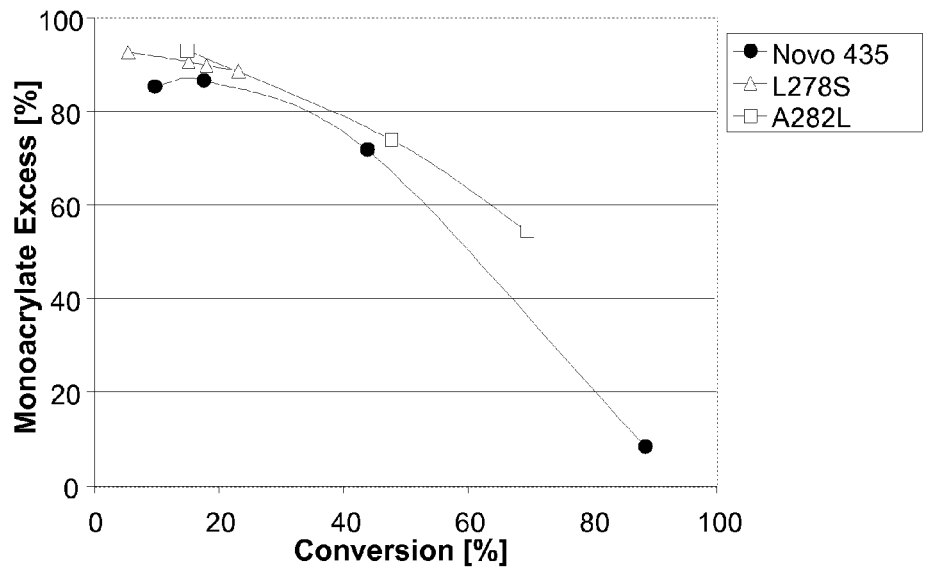

FIG. 12 shows the excess of 4-hydroxybutanediol over butanediole diacrylate at various rates of conversion after enzymatic catalysis by a commercially available enzyme (Novo 435) (represented by filled dots), the A282L mutant (open squares) or the L278S mutant (open triangles). In the respective ranges tested, both CALB mutants show a measurable excess of 4-hydroxybutanediol over a wide range of achieved conversions.

Figure 13:
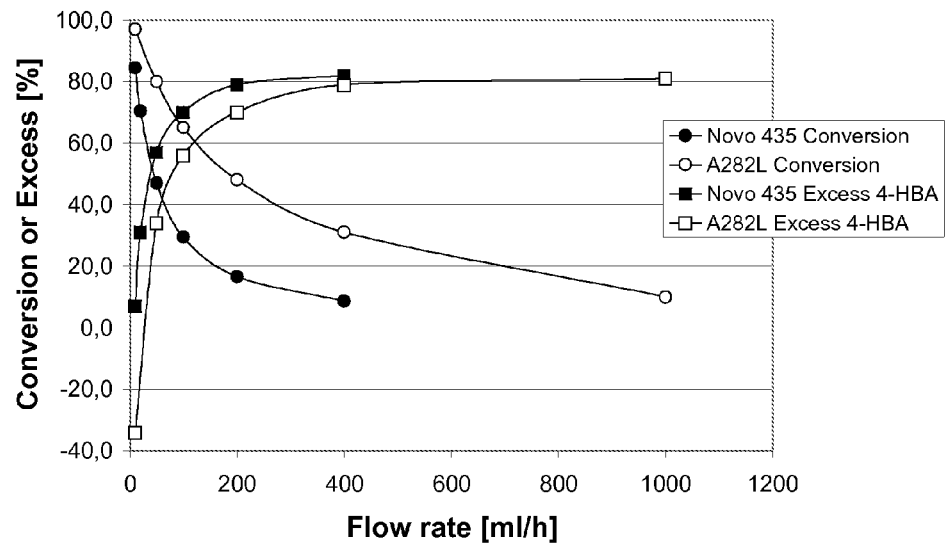

FIG. 13 shows the dependency of product excess or conversion rates from flow rates for CALB Novo 435 and CALB A282L. Filled or open dots represent conversion by Novo 435 or A282L, resp., and filled or open squares represent excess of 4-HBA achieved by Novo 435 or A282L, resp., at a given conversion.

Figure 14A:
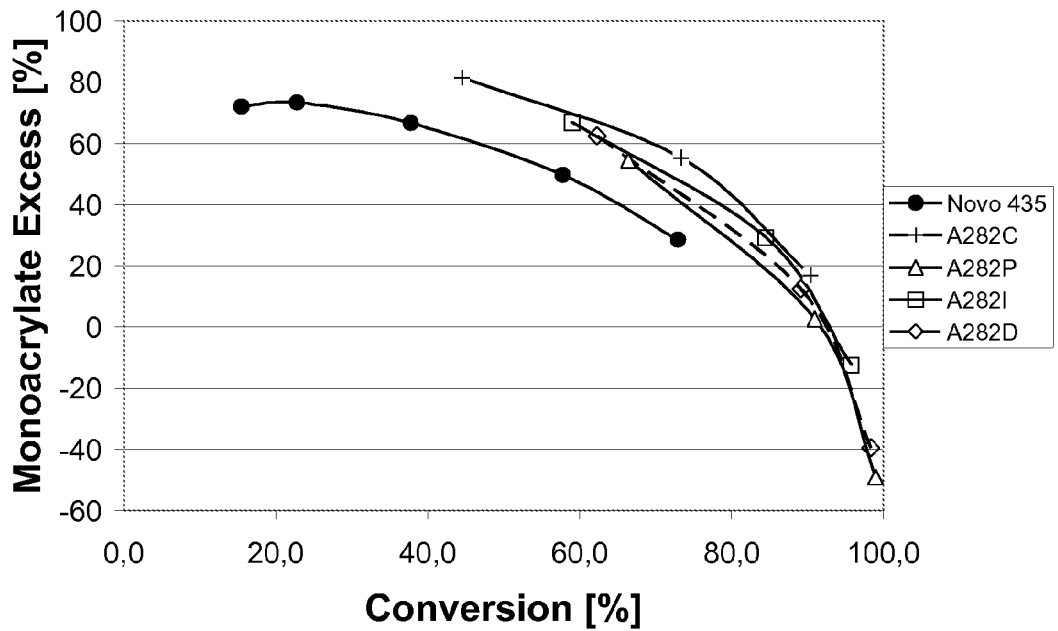
Figure 14B:
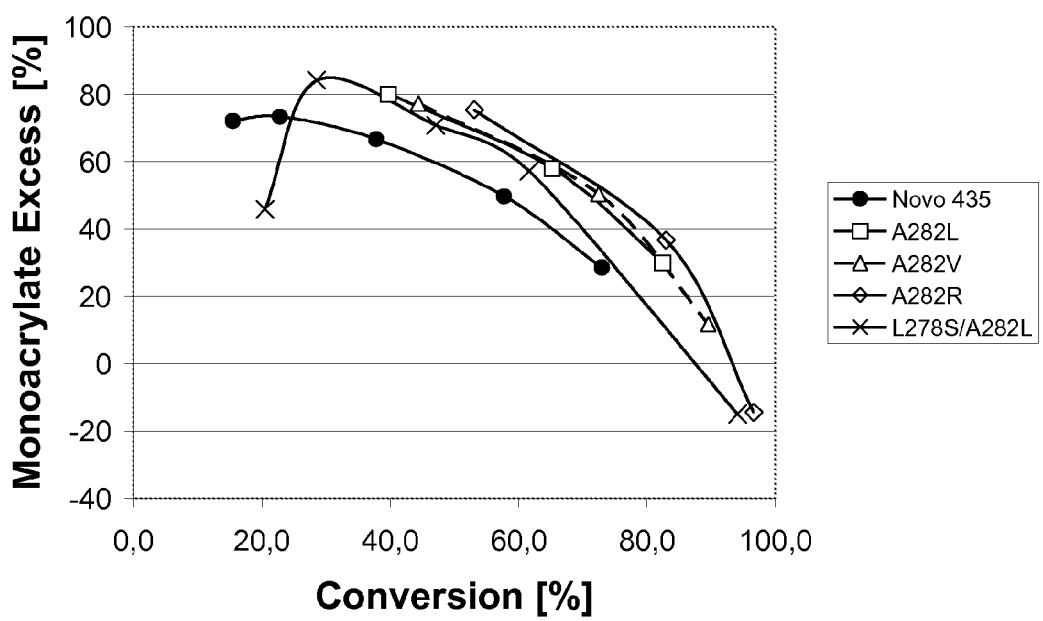

FIG. 14 shows the excess of produced monoacrylate versus the degree of conversion in comparison of CALB Novo 435 and selected CALB mutants according to the invention. The results are based on samples taken directly from the medium. FIG. 14A: comprises results from A282C (labelled by crosses); A282P (open triangles); A282I (open squares); A282D (open diamonds, dashed line); FIG. 14B comprises results from A282L (open squares); A282V (open triangles, dashed line); A282R (open diamonds) and L278S/A282L (crosses), while both in FIG. 14A and FIG. 14B Novo 435 is represented by filled dots.

Figure 15A:
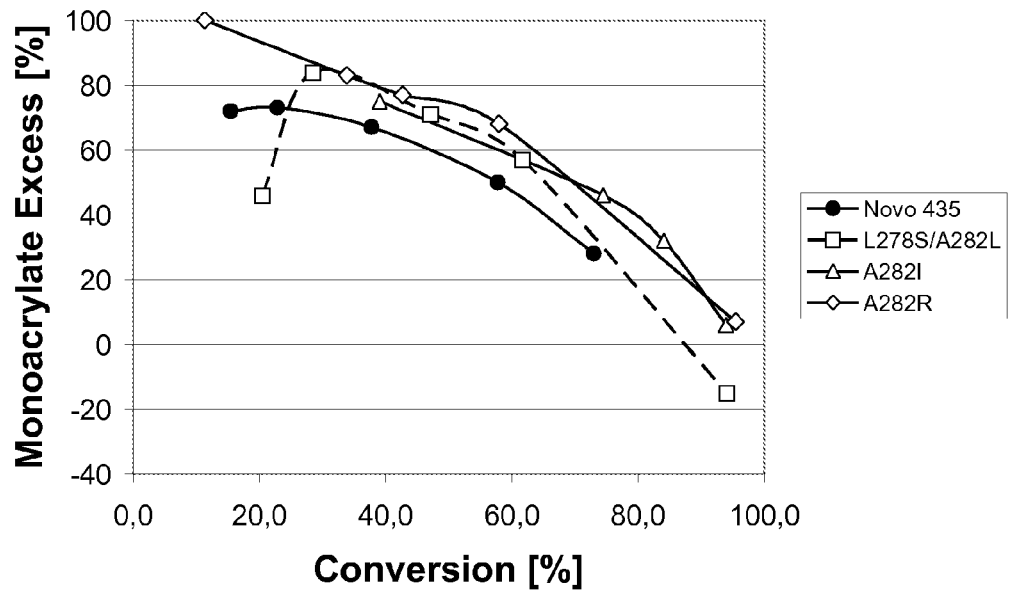
Figure 15B:
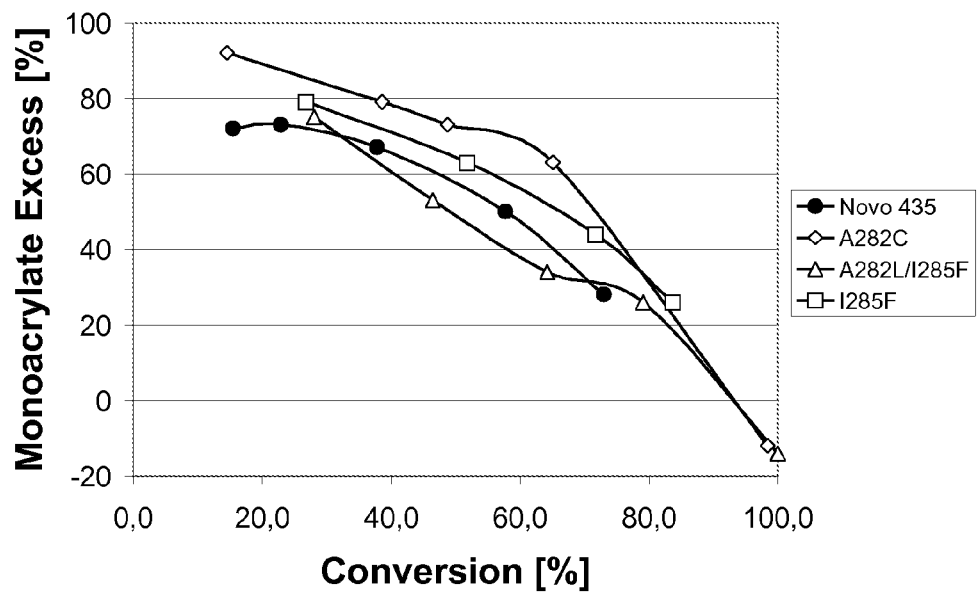

FIG. 15 shows the excess of produced monoacrylate versus degree of conversion in comparison of CALB Novo 435 and selected CALB mutants according to the invention. The results are based on enzyme immobilized on Resindinon Diaion HP20 L beads (Resindion SRL, a subsidiary of Mitsubishi Chemical). FIG. 15A comprises results from: A282I (represented by open triangles), A282R (open diamonds), and L278S/A282L (open squares, dashed line); FIG. 15B comprises results from A282C (open diamonds), I285F (open squares) and A282L/I285F (open triangles), while both in FIG. 15A and FIG. 15B Novo 435 is represented by filled dots.

DETAILED DESCRIPTION OF THE INVENTION

1. General Definitions

In the absence of information to the contrary the following general definitions shall apply:

According to the invention, "triacylglycerol lipases" means enzymes of class E.C. 3.1.1.3 according to the IUBMB enzyme nomenclature (http://www.iubmb.unibe.ch; http://www.chem.qmul.ac.uk/iubmb/enzyme/).

According to a special embodiment of the method according to the invention, the functionally expressed triacylglycerol lipase is lipase B, the gene product of CALB from *Candida antarctica*. The CALB gene was described (Uppenberg et al., 1994) and its nucleotide or protein sequence was deposited under the access numbers Z30645 and CAA83122.1 at GenBank. Unless designated more precisely, here CALB means a nucleotide sequence with this access number. Another example of a triacylglycerol lipase is lipase B from *Pseudozyma tsukubaensis* (Suen, W. C., Zhang, N., Xiao, L., Madison, V., Zaks, A. *Protein Eng. Des. Sel.* 17(2): 133-40 (2004)).

An "enzymatically catalyzed" or "biocatalytic" method means that said method is performed under the catalytic action of an enzyme, including enzyme mutants, as herein defined. Thus the method can either be performed in the presence of said enzyme in isolated (purified, enriched) or crude form or in the presence of a cellular system, in particular, natural or recombinant microbial cells containing said enzyme in active form, and having the ability to catalyze the conversion reaction as disclosed herein.

The terms "selectively mono-acylating polyols" or "increasing the selectivity for mono-acylating polyols" in general means that a monoester of said polyol is produced in a higher proportion or amount (compared on a molar basis) than at least one, preferably all, higher esterified polyol components during the course of the esterification reaction disclosed herein, i.e. either during the entire course of said reaction (i.e. between initiation and termination of the reaction), at a certain point of time of said reaction, or during an "interval" of said reaction. In particular, said selectivity may be observed during an "interval" corresponding 1 to 99%, 2 to 95%, 3 to 90%, 5 to 85%, 10 to 80%, 15 to 75%, 20 to 70%, 25 to 65%, 30 to 60, or 40 to 50% conversion of the initial amount of polyol substrate. Said higher proportion or amount may, for example, be expressed in terms of:

- a higher maximum yield of the monoacylated polyol observed during the entire course of the reaction or said interval thereof;
- a higher relative amount of the monoacylated product at a defined % conversion value of the polyol; and/or
- an identical relative amount of the monoacylated product at a higher % degree of conversion value;

each of which being observed relative to a reference method, said reference method being performed under otherwise identical condition with the corresponding non-mutated lipase enzyme.

The term "product distribution" describes the proportion of the partial amount of a certain reaction product formed at a certain point of time or "interval" during the course of the enzyme catalyzed method described herein relative to the total amount of all products formed by of said method, expressed in percent. Thus the "product distribution" for a monoester of a certain polyol defines the proportion (in percent) of said monoester relative to the total amount of esters (mono- and polyesters), which have been produced under the influence of an enzyme as defined herein at a certain point of time or within a defined interval after initiation of said enzymatic esterification reaction.

"Optically active" compounds are those having at least one certer of asymmetry, i.p. at least one asymmetric carbon atom.

The term "about" indicates a potential variation of ±25% of the stated value, in particular ±15%, ±10%, ±5%, ±2% or ±1%.

The term "substantially" indicates a potential variation of ±10% of the stated value, in particular ±5%, ±1%, ±0.5%, ±0.2% or ±0.1% or less.

"Stereoselectivity" or "enantioselectivity" describes the ability to produce an optically active compound in a stereoisomerically or enantiomerically pure form or to specifically convert a particular stereoisomer or An enzymatically catalyzed method of preparing mono-acylated polyols enantiomer out of a plurality of stereisomers or enantiomers. More specifically, this means that a product of the invention is enriched with respect to a specific stereoisomer or enantiomer. This may be quantified via the enantiomeric purity % ee-parameter calculated according to the formula:

$$\% \ ee = [X_A - X_B]/[X_A + X_B] * 100,$$

wherein $X_A$ and $X_B$ represent the molar ratio (Molenbruch) of the enantiomers A and B.

Enantiomeric purities of at least 90% ee, like at least 95% ee, or at lest 98% ee, or at east 99% ee or more may be obtained.

The term "capable of forming a hydrogen bridge" refers to the ability of an amino acid residue of an enzyme molecule of the invention to form a hydrogen bridge with another molecule, as for example with another amino acid residue of said enzyme or with a substrate molecule or an intermediate state thereof located at or within said enzyme molecule.

An condition "which stabilizes" an oxyanion transition state means a condition which makes said oxyanion state energetically more favorable if compared to the non-stabilized state. Stabilization may, for example, be effected by a delocalization of the negative charge of the anion.

The "substrate pocket" of an enzyme as defined herein, or its "reactivity centre" harbours during the reaction to be catalyzed a substrate molecule of and converts it to a product of formula I. Said substrate pocket is composed of certain "structural elements" i.e. portions of said substrate pocket with different function. Said structural elements are in "functional arrangement" to each other, i.e. they cooperate during the reaction to be catalyzed.

A "sequence motif" or "pattern" represents a characteristic arrangement or "fingerprint" of a plurality of amino acid residues which are either adjacent to each other within a specific amino acid sequence or are separated from each other in a defined manner, i.e. by intermediate spacer sequences of characteristic length.

An "extended substrate specificity" refers to enzymes which, if compared to a reference enzyme, convert additional structurally different substrates.

An "altered/modified substrate specificity" refers to enzymes which, if compared to a reference enzyme, convert a partially or completely different set of substrate molecules. Thus, the term "altered substrate specificity" may describes a situation where a lipase enzyme, for example effected by mutation, is better adapted for the acylation of a specific substrate molecule than a reference enzyme (as for example the non-mutated enzyme). For example, a higher preference or specificity may be caused by a higher substrate affinity of the binding pocked formed by the enzyme variants.

An "altered/modified regioselectivity" refers to enzymes which, if compared to a reference enzyme, convert the one or more potential reactive sites of a substrate molecule with altered preference. Thus, the term "altered regioselectivity" may describes a situation where a lipase enzyme, for example effected by mutation, is better adapted for the mono-acylation of a specific substrate molecule having more than one acylatable functional groups than a reference enzyme (as for example the non-mutated enzyme).

Due to the reversibility of enzymatic reactions the present invention may also relate to the corresponding reverse (i.e. deacylation) reaction of the biocatalytic acylation reactions described herein.

2. Particular Embodiments of the Invention

The present invention provides the following particular embodiments:
1. A biocatalytic, enzymatically catalyzed method of preparing a mono-acylated polyol, in particular mono-acylated diol, of the general formula (I):

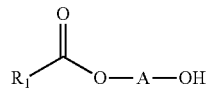
(I)

wherein
$R_1$ represents an optionally substituted, linear or branched, saturated or non-saturated hydrocarbyl residue; and
A represents an optionally substituted, linear or branched, non-cyclic, hydrocarbylene residue, in particular having at least two carbon atoms, and, in particular, wherein the oxygen atoms are linked to different carbon atoms;
which method comprises
a) reacting a polyol of the formula (II) and an acyl donor compound of the formula (III)

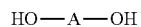
(II)

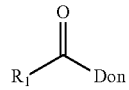
(III)

wherein $R_1$ and A are as defined above, in particular, wherein the hydroxyl groups are linked to different carbon atoms, and
Don represents a donor molecule residue carrying the said acyl group, and is preferably selected from —OR groups, wherein R represents an optionally substituted, linear or branched, saturated or non-saturated, hydrocarbyl residue;
in the presence of a mutated triacylglycerole lipase (EC 3.1.1.3) until a mono-acylated polyol of the above formula (I) is formed; and
b) obtaining a monoacylated polyol product.
2. The method of embodiment 1, wherein said mutated lipase contains at least one amino acid mutation, which increases the selectivity of the lipase for the mono-acylation of said polyol, if compared to the corresponding non-mutated lipase.
3. The method of one of the preceding embodiments, wherein said mutant comprises at least one mutation, which removes a stabilizing functional amino acid group, in particular an amino acid side chain capable of forming a hydrogen bridge, from that part of the reactive center of the enzyme which stabilizes an oxyanion transition state of the carbonyl group of the mono-acylated polyol of formula (I) to be formed.
4. The method of one of the preceding embodiments, wherein the enzyme is mutated such that
a) a maximum monoester yield is obtained which is at last 1%, as for example 2 to 1000, 5 to 500, 10 to 200, 15 to 100, 10 to 80 or 15 to 50%, above the maximum yield as obtained by the corresponding wild-type enzyme;
b) a 3:1 molar ratio of monoester to polyester is reached at a conversion rate of the polyol which is at last 1% as for example 2 to 1000, 5 to 500, to 200, 15 to 100, 10 to 80 or 15 to 50%, above the corresponding conversion rate as obtained by the corresponding wild-type enzyme; and/or
c) the ratio of reaction times ($T_{90}$(mutant)/$T_{90}$(wild-type)) to reach 90% (on molar basis) monoacylated polyol based on the total amount of polyol is above 1, as for example in the range of about 2 to 1000, 5 to 500, 10 to 200, 15 to 100, 10 to 80 or 15 to 50.

5. The method of one of the preceding embodiments, wherein said enzyme is a mutant of *Candida antarctica* lipase B (CALB) comprising an amino acid sequence of SEQ ID NO: 2, mutated in at least one position, as for example 1, 2, 3, 4, 5, 6, 7, 8, 9, or 10 positions.

6. The method of embodiment 5, wherein said mutant comprises an amino acid sequence of SEQ ID NO:2 wherein at least the amino acid Thr40 is mutated.

7. The method of embodiment 6, wherein the mutation is such that substantially no stabilizing interaction between the oxyanion intermediate and the amino acid residue in position 40 occurs.

8. The method of embodiment 7 wherein the mutation comprises the single mutations Thr40Ala, Thr40Val or Thr40Ser.

9. The method of embodiment 8, wherein said mutant is selected from mutants having an amino acid sequence of SEQ ID NO: 4 or variants of said mutant having a sequence identity of at least 60%, which variants still contain a mutation in an amino acid position corresponding to position Thr40 of SEQ ID NO:2 or 4.

10. The method of one of the embodiments 7 to 9, wherein the mutant additionally comprises at least one mutation in one of the amino acid positions Leu 278, Ile 285 and Pro 280 of SEQ ID NO: 2 or 4.

11. The method of embodiment 10, wherein the mutants and the variants thereof are not mutated in other amino acid positions contributing to the catalytic site of the enzyme.

12. The method of embodiment 11, wherein the mutants are not mutated in amino acid positions Ser105, Asp187, His224 (catalytic triade) and Gln106 and wherein the variants are not mutated in amino acid positions corresponding thereto.

13. The method of any one of embodiments 5 to 12, wherein in SEQ ID NO:2, or in SEQ ID NO:2 comprising a mutation at amino acid Thr40 according to SEQ ID NO:4, one or more of Leu278, Ala281, Ala282 or Ile285 are mutated.

14. The method of embodiment 13, wherein the one or more mutations are independently selected from:
Leu 278Ser for Leu278,
Ala281Val or Ala281Glu for Ala281, and
Ala282Leu, Ala282Thr, Ala282Cys, Ala282Pro, Ala282Ile, Ala282Asp,
Ala282Val, Ala282Met or Ala282Arg for Ala282.

15. The method of embodiment 14, wherein SEQ ID NO:2 comprises one mutation, selected from Ala281Val, Ala281Glu, Ala282Leu, Ala282Thr, Ala282Cys, Ala282Pro, Ala282Ile, Ala282Asp, Ala282Val, Ala282Met, Ala282Arg and Ile285Phe, or wherein SEQ ID NO:2 comprises the double mutation Leu278Ser and Ala282Leu.

16. The method of one of the preceding embodiments, wherein the reaction is performed in the presence of the isolated enzyme mutant or a recombinant microorganism functionally expressing said mutant.

17. The method of one of the preceding embodiments, wherein the polyol is a compound of formula (II) wherein A is selected from the groups —(CH$_2$)$_n$— and —(CH$_2$)$_m$—CR$_2$R$_3$—(CH$_2$)$_m'$— wherein
n is an integer of 2-6,
m and m' independently of each other are integers of 1-3

R$_2$ and R$_3$ independently of each other are selected from H, OH, SH, NH$_2$, optionally substituted carbo- or heterocyclic rings and hydrocarbyl-residues, provided that R$_2$ and R$_3$ are not simultaneously H.

18. The method of one of the preceding embodiments, wherein the donor of formula (III) is selected from compounds wherein R$_1$ is C$_1$-C$_6$-alkyl and Don is an —OR residue, wherein R is selected from C$_1$-C$_6$-alkyl and C$_2$-C$_4$-alkenyl.

19. An biocatalytic, enzymatically catalyzed, method of enantioselectively preparing an asymmetric mono-acylated polyol of the general formula (I):

wherein
R$_1$ represents an optionally substituted, linear or branched, non-cyclic, saturated or non-saturated hydrocarbyl residue; and
A* represents an optionally substituted, linear or branched, asymmetric hydrocarbylene residue, having at least two carbon atoms, and, in particular, wherein the oxygen atoms are linked to different carbon atoms;
which method comprises
a) reacting a stereoisomeric mixture of a polyol of the formula (II') and an acyl donor compound of the formula (III)

wherein R$_1$ and A* are as defined above, in particular, wherein the hydroxyl groups are linked to different carbon atoms, and
Don represents a donor molecule residue carrying the said acyl group, and is preferably selected from —OR groups, wherein R represents an optionally substituted, linear or branched, saturated or non-saturated hydrocarbyl residue;
in the presence of a mutated triacylglycerol lipase (EC 3.1.1.3) until a mono-acylated polyol of the above formula (I) is formed; and
b) obtaining an asymmetric monoacylated polyol product.

20. The method of embodiment 19 wherein an enzyme mutant as defined in anyone of the embodiments 2 to 15 in the form of an isolated enzyme mutant or a recombinant microorganism functionally expressing said mutant is applied.

21. The method of embodiment 19 or 20, wherein the polyol is a compound of formula (II') wherein A* is selected from the groups —(CH$_2$)$_m$—CHR$_2$—(CH$_2$)$_m'$— wherein m, m' and R$_2$ are as defined above.

22. The use of a mutated triacylglycerol lipase (EC 3.1.1.3) in a method of preparing a mono-acylated polyol of the general formula (I) or (I') as defined above.

23. A *Candida antarctica* lipase B (CALB) mutant showing a pattern of at least two mutations of the amino acid sequence of SEQ ID NO:2 or 4, which pattern is selected from the pattern as shown in Table A below.

24. The mutant of embodiment 23 showing additionally one mutation selected from Val210 Ile, Ala281 Glu, Val221 Asp in a sequence of SEQ ID NO:2 or 4.

25. A *Candida antarctica* lipase B (CALB) mutant, having one or more mutations in the amino acid sequence of SEQ ID NO:2, which are independently selected from
Leu278Ser for Leu278,
Ala281Val or Ala281Glu for Ala281, and
Ala282Leu, Ala282Thr, Ala282Cys, Ala282Pro, Ala282Ile, Ala282Asp,
Ala282Val, Ala282Met or Ala282Arg for Ala282.

26. The mutant of embodiment 25, having one mutation in SEQ ID NO:2, selected from Ala281Val, Ala281Glu, Ala282Leu, Ala282Thr, Ala282Cys, Ala282Pro, Ala282Ile, Ala282Asp, Ala282Val, Ala282Met, Ala282Arg and Ile285Phe, or having in SEQ ID NO:2 the double mutation Leu278Ser and Ala282Leu.

27. The mutant of embodiment 23 or 24, additionally having at least one of the mutations as defined in any one of embodiments 25 or 26.

28. A nucleic acid molecule encoding a mutant of one of the embodiments 20 to 27.

29. An expression vector, comprising, optionally under the control of a regulatory nucleic acid sequence, at least one coding sequence of embodiment 28.

24. A microbial host carrying at least one expression vector of embodiment 23 or coding sequence of embodiment 22.

TABLE A

| Specific Mutation pattern: | | | |
|---|---|---|---|
| Thr40 | Leu278 | Ile285 | Pro280 |
| 2-fold mutants | | | |
| Ala | Phe | | |
| Ala | Trp | | |
| Ala | Ala | | |
| Ala | Ser | | |
| Ala | Asn | | |
| Ala | | Leu | |
| Ala | | Ser | |
| Ala | | Phe | |
| Ala | | Gln | |
| Ala | | | Ala |
| Val | Phe | | |
| Val | Trp | | |
| Val | Ala | | |
| Val | Ser | | |
| Val | Asn | | |
| Val | | Leu | |
| Val | | Ser | |
| Val | | Phe | |
| Val | | Gln | |
| Val | | | Ala |
| Ser | Trp | | |
| Ser | Ala | | |
| Ser | Ser | | |
| Ser | Asn | | |
| Ser | | Leu | |
| Ser | | Ser | |
| Ser | | Phe | |
| Ser | | Gln | |
| Ser | | | Ala |
| 3-fold mutants | | | |
| Ala | Phe | Leu | |
| Ala | Phe | Ser | |
| Ala | Phe | Phe | |

TABLE A-continued

| Specific Mutation pattern: | | | |
|---|---|---|---|
| Thr40 | Leu278 | Ile285 | Pro280 |
| Ala | Phe | Gln | |
| Ala | Phe | | Ala |
| Ala | Trp | Leu | |
| Ala | Trp | Ser | |
| Ala | Trp | Phe | |
| Ala | Trp | Gln | |
| Ala | Trp | | Ala |
| Ala | Ala | Leu | |
| Ala | Ala | Ser | |
| Ala | Ala | Phe | |
| Ala | Ala | Gln | |
| Ala | Ala | | Ala |
| Ala | Ser | Leu | |
| Ala | Ser | Ser | |
| Ala | Ser | Phe | |
| Ala | Ser | Gln | |
| Ala | Ser | | Ala |
| Ala | Asn | Leu | |
| Ala | Asn | Ser | |
| Ala | Asn | Phe | |
| Ala | Asn | Gln | |
| Ala | Asn | | Ala |
| Val | Phe | Leu | |
| Val | Phe | Ser | |
| Val | Phe | Phe | |
| Val | Phe | Gln | |
| Val | Phe | | Ala |
| Val | Trp | Leu | |
| Val | Trp | Ser | |
| Val | Trp | Phe | |
| Val | Trp | Gln | |
| Val | Trp | | Ala |
| Val | Ala | Leu | |
| Val | Ala | Ser | |
| Val | Ala | Phe | |
| Val | Ala | Gln | |
| Val | Ala | | Ala |
| Val | Ser | Leu | |
| Val | Ser | Ser | |
| Val | Ser | Phe | |
| Val | Ser | Gln | |
| Val | Ser | | Ala |
| Val | Asn | Leu | |
| Val | Asn | Ser | |
| Val | Asn | Phe | |
| Val | Asn | Gln | |
| Val | Asn | | Ala |
| Ser | Phe | Leu | |
| Ser | Phe | Ser | |
| Ser | Phe | Phe | |
| Ser | Phe | Gln | |
| Ser | Phe | | Ala |
| Ser | Trp | Leu | |
| Ser | Trp | Ser | |
| Ser | Trp | Phe | |
| Ser | Trp | Gln | |
| Ser | Trp | | Ala |
| Ser | Ala | Leu | |
| Ser | Ala | Ser | |
| Ser | Ala | Phe | |
| Ser | Ala | Gln | |
| Ser | Ala | | Ala |
| Ser | Ser | Leu | |
| Ser | Ser | Ser | |
| Ser | Ser | Phe | |
| Ser | Ser | Gln | |
| Ser | Ser | | Ala |
| Ser | Asn | Leu | |
| Ser | Asn | Ser | |
| Ser | Asn | Phe | |
| Ser | Asn | Gln | |
| Ser | Asn | | Ala |
| 4-fold mutants | | | |
| Ala | Phe | Leu | Ala |
| Ala | Phe | Ser | Ala |

TABLE A-continued

Specific Mutation pattern:

| Thr40 | Leu278 | Ile285 | Pro280 |
|-------|--------|--------|--------|
| Ala | Phe | Phe | Ala |
| Ala | Phe | Gln | Ala |
| Ala | Trp | Leu | Ala |
| Ala | Trp | Ser | Ala |
| Ala | Trp | Phe | Ala |
| Ala | Trp | Gln | Ala |
| Ala | Ala | Leu | Ala |
| Ala | Ala | Ser | Ala |
| Ala | Ala | Phe | Ala |
| Ala | Ala | Gln | Ala |
| Ala | Ser | Leu | Ala |
| Ala | Ser | Ser | Ala |
| Ala | Ser | Phe | Ala |
| Ala | Ser | Gln | Ala |
| Ala | Asn | Leu | Ala |
| Ala | Asn | Ser | Ala |
| Ala | Asn | Phe | Ala |
| Ala | Asn | Gln | Ala |
| Val | Phe | Leu | Ala |
| Val | Phe | Ser | Ala |
| Val | Phe | Phe | Ala |
| Val | Phe | Gln | Ala |
| Val | Trp | Leu | Ala |
| Val | Trp | Ser | Ala |
| Val | Trp | Phe | Ala |
| Val | Trp | Gln | Ala |
| Val | Ala | Leu | Ala |
| Val | Ala | Ser | Ala |
| Val | Ala | Phe | Ala |
| Val | Ala | Gln | Ala |
| Val | Ser | Leu | Ala |
| Val | Ser | Ser | Ala |
| Val | Ser | Phe | Ala |
| Val | Ser | Gln | Ala |
| Val | Asn | Leu | Ala |
| Val | Asn | Ser | Ala |
| Val | Asn | Phe | Ala |
| Val | Asn | Gln | Ala |
| Ser | Phe | Leu | Ala |
| Ser | Phe | Ser | Ala |
| Ser | Phe | Phe | Ala |
| Ser | Phe | Gln | Ala |
| Ser | Trp | Leu | Ala |
| Ser | Trp | Ser | Ala |
| Ser | Trp | Phe | Ala |
| Ser | Trp | Gln | Ala |
| Ser | Ala | Leu | Ala |
| Ser | Ala | Ser | Ala |
| Ser | Ala | Phe | Ala |
| Ser | Ala | Gln | Ala |
| Ser | Ser | Leu | Ala |
| Ser | Ser | Ser | Ala |
| Ser | Ser | Phe | Ala |
| Ser | Ser | Gln | Ala |
| Ser | Asn | Leu | Ala |
| Ser | Asn | Ser | Ala |
| Ser | Asn | Phe | Ala |
| Ser | Asn | Gln | Ala |

3. Substrates a) Polyols

Polyols to be acylated according to the present invention are generally of the general Formula II $$HO-A-OH \quad (II)$$

wherein A represents an optionally substituted, linear or branched, non-cyclic, hydrocarbylene residue, having at least two carbon atoms, and wherein the hydroxyl groups are linked to different carbon atoms;

"Non-cyclic" in this context means that the HO-Groups are not linked to a carbo- or heterocyclic mono- or polynuclear ring.

A is in particular formed by a hydrocarbylene-backbone B carrying both HO-groups according to the following general formula

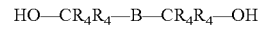

wherein
the $R_4$ residues independently of each other may be selected from H and linear or branched, in particular linear, $C_1$-$C_6$-alkyl, and
B represents a group of the formula —$(CR_5R_5)_z$—
wherein z is an integer of 0, 1, 2, 3, 4, 5 or 6 and
the $R_5$ residues independently of each other are selected from H, linear or branched, in particular linear, $C_1$-$C_6$-alkyl, optionally substituted $C_3$-$C_7$-cycloalkyl and optionally substituted aryl or heteroaryl.

In another embodiment the hydroxyl groups of the diol to be acylated independently of each other may be tertiary, secondary or primary hydroxyl groups.

Particular examples of A groups are selected from the following groups, adapted to carrying two primary hydroxyl groups:

$$—(CH_2)_n— \text{ and}$$

wherein
n is an integer of 1, 2, 3, 4, 5, or 6,
m and m' independently of each other are integers of 1, 2 or 3
$R_2$ and $R_3$ independently of each other are selected from H, OH, SH, $NH_2$, carbo- or heterocyclic ring, in particular, optionally substituted $C_3$-$C_7$-cycloalkyl, aryl or heterorayl; and, linear or branched, in particular linear, $C_1$-$C_6$-alkyl, provided that $R_2$ and $R_3$ are not simultaneously H.

b) Acyl Donors

The "acyl donor" molecule has the ability to provide an acyl group for the biocatalytic acylation reaction of the invention.

Generally the donor is of the above formula (III) wherein $R_1$ represents an optionally substituted, linear or branched, saturated or non-saturated hydrocarbyl residue, in particular $C_1$-$C_{30}$-hydrocarbyl; and Don represents a donor molecule residue carrying the said acyl group, and is preferably selected from —OR groups wherein R represents an optionally substituted, linear or branched, saturated or non-saturated, hydrocarbyl residue, in particular $C_1$-$C_6$-alkyl or $C_2$-$C_4$—alkenyl, like methyl, ethyl or vinyl.

c) Definitions

A "hydrocarbylene" residue of the present invention particularly comprises a linear —$(CH_2)_n$— backbone with n=1, 2, 3, 4, 5, 6, 7, or 8, which may be further substituted as further defined herein.

A linear or branched, saturated or non-saturated, "hydrocarbyl" residue according to the preset invention particularly refers to linear or branched, alkyl or alkenyl residues.

An "alkyl" residue comprises $C_1$-$C_8$-alkyl radicals which are linear or branched radicals having from 1 to 8 carbon atoms. Examples thereof are:

$C_1$-$C_4$-alkyl radicals selected from methyl, ethyl, n-propyl, isopropyl, n-butyl, 2-butyl, isobutyl or tert-butyl, $C_1$-$C_6$-alkyl radicals selected from $C_1$-$C_4$-alkyl radicals as defined above and additionally pentyl, 1-methylbutyl, 2-methylbutyl, 3-methylbutyl, 2,2-dimethylpropyl, 1-ethylpropyl, hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl, 1-ethyl-2-methylpropyl, $C_1$-$C_8$-alkyl radicals selected from $C_1$-$C_6$-alkyl radicals as defined above and additionally heptyl, octyl and their constitutional isomers such as 2-ethylhexyl; and $C_8$-$C_{30}$-alkyl radicals which are linear or branched radicals having from 8 to 30 carbon atoms; examples thereof being selected from octyl, nonyl, decyl, undecyl, dodecyl, tridecyl, tetradecyl, pentadecyl, hexadecyl, heptadecyl, octadecyl, nonadecyl, eicosyl, hencosyl, docosyl, tricosyl, tetracosyl, pentacosyl, hexacosyl, heptacosyl, octacosyl, nonacosyl, squalyl, their constitutional isomers, higher homologs and constitutional isomers thereof.

An "alkenyl" residue comprises $C_2$-$C_{30}$-alkenyl radicals which are monounsaturated linear or branched hydrocarbon radicals having from 2 to 30 carbon atoms.

Particular examples are:

$C_2$-$C_4$-alkenyl radicals, like ethenyl or vinyl, 1- or 2-propenyl, 1-, 2- and 3-butenyl, $C_2$-$C_8$-alkenyl radicals comprising $C_2$-$C_4$-alkenyl radicals as defined above as well as 2-methylpropen-3-yl, 2-methylpropen-1-yl, 1-, 2-, 3- and 4-pentenyl, 1-, 2-, 3-, 4- and 5-hexenyl, 1-, 2-, 3-, 4-, 5- and 6-heptenyl 1-, 2-, 3-, 4-, 5-, 6- and 7-octenyl and also their constitutional isomers; as well as $C_8$-$C_{30}$-alkenyl residues which are monounsaturated linear or branched hydrocarbon radicals having from 8 to 30 carbon atoms. Examples thereof are octenyl, nonenyl, decenyl, undecenyl, dodecenyl, tridecenyl, tetradecenyl, pentadecenyl, hexadecenyl, heptadecenyl, octadecenyl, nonadecenyl, eicosenyl, hencosenyl, docosenyl, tricosenyl, tetracosenyl, pentacosenyl, hexacosenyl, heptacosenyl, octacosenyl, nonacosenyl, squalenyl, their constitutional isomers, higher homologs and constitutional isomers thereof.

"Carbo- and heterocyclic" residues comprise, optionally condensed, aromatic or non-aromatic ring groups, having 3 to 12 carbon atoms and optionally 1, 2, 3 or 4 same or different ring-heteroatoms, like N, S and O.

As examples there may be mentioned:

aromatic carbocyclic rings like phenyl and naphthyl.

non-aromatic carbocyclic rings, in particular $C_3$-$C_7$-cycloalkyl residues like cyclopropyl, cyclopropyl-methyl, cyclopropyl-ethyl, cyclobutyl, cyclobutyl-methyl, cyclopentyl, cyclopentyl-methyl, cyclohexyl, cyclohexyl-methyl, Cycloheptyl, as well as the one- or two-fold unsaturated analogues thereof, like for example cyclobutenyl, cyclopentenyl, cyclohexenyl, cycloheptenyl, cyclohexadienyl, cycloheptadienyl;

5- to 7-membered saturated or unsaturated, aromatic or nonaromatic heterocyclic residues having 1 to 4 ring-heteroatoms, selected from O, N and S, wherein said heterocyclic group may be condensed with a further hetero or carbocyclic residue. As examples there may be mentioned residues of pyrrolidine, tetrahydrofurane, piperidine, morpholine, pyrrole, furan, thiophene, pyrazole, imidazole, oxazole, thiazole, pyridine, pyran, pyrimidine, pyridazine, pyrazine, cumarone, indole and quinoline.

Non-limiting examples of "optionally substituted" residues as defined herein comprise 1, 2, 3, 4, 5 or 6 identical or different substituents like, HO, SH, $NH_2$, $NO_2$, halogen, like F, Cl, Br, J; lower alkyl, lower alkoxy, lower alkylthio, lower alkyl, lower alkenyl, lower alkynyl or hydroxyl-lower alkyl, as defined above.

"Lower alkyl" refers to $C_1$-$C_8$-alkyl radicals as defined above.

"Lower alkoxy" preferably refers to the $C_1$-$C_8$-alkoxy analogues of the above-mentioned lower alkyl radicals.

"Lower alkylthio" preferably refers to the $C_1$-$C_8$-alkthio analogues of the above-mentioned lower alkyl radicals. Examples are methylthio, ethylthio, propylthio, isopropylthio, butylthio, sec-butylthio, isobutylthio and tert-butylthio.

"Lower alkenyl" comprises $C_2$-$C_8$-alkenyl radicals as defined above.

"Lower alkynyl" comprises the alkynyl homologues of the above "lower alkenyl" radicals.

The term "hydroxy lower-alkyl" refers to $C_1$-$C_8$-hydroxyalkyl which is a linear or branched alkyl radical having from 1 to 8, in particular from 1 to 4 carbon atoms, in which at least one hydrogen atom, for example 1 or 2 of the hydrogen atoms, is/are replaced by a hydroxyl group. Examples thereof are, hydroxymethyl, 2-hydroxy-1-ethyl, 2- and 3-hydroxy-1-propyl, 2-, 3- and 4-hydroxy-1-butyl, 2-, 3-, 4- and 5-hydroxy-1-pentyl, 2-, 3-, 4-, 5- and 6-hydroxy-1-hexyl, 2-, 3-, 4-, 5-, 6- and 7-hydroxy-1-heptyl, 2-, 3-, 4-, 5-, 6-, 7- and 8-hydroxy-1-octyl, 2,3-dihydroxy-1-propyl and their constitutional isomers.

The above definitions provided under a) b) and c) simultaneously apply to the compounds of formulae (I'), (II') and (III').

4. Enzymes and Enzyme Mutants According to the Invention

The present invention is not limited to the use of the specifically disclosed triacylglycerole lipases and mutants, but also extends to functional equivalents thereof.

"Functional equivalents" or analogs of the concretely disclosed enzymes are, within the scope of the present invention, various polypeptides thereof, which moreover possess the desired biological function or activity, e.g. enzyme activity.

For example, "functional equivalents" means enzymes, which, in a test used for enzymatic activity, display at least a 1 to 10%, or at least 20%, or at least 50%, or at least 75%, or at least 90% higher or lower activity of an enzyme, as defined herein.

"Functional equivalents", according to the invention, also means in particular mutants, which, in at least one sequence position of the amino acid sequences stated above, have an amino acid that is different from that concretely stated, but nevertheless possess one of the aforementioned biological activities. "Functional equivalents" thus comprise the mutants obtainable by one or more, as for example 1, 2, 3, 4, 5, 6, 7, 8, 9, 10, 11, 12, 13, 14, or 15, amino acid additions, substitutions, insertions, deletions and/or inversions, where the stated changes can occur in any sequence position, provided they lead to a mutant with the profile of properties according to the invention. Functional equivalence is in particular also provided if the reactivity patterns coincide qualitatively between the mutant and the unchanged polypeptide, i.e. if for example the same substrates are converted at a different rate. Examples of suitable amino acid substitutions are shown in the following table:

| Original residue | Examples of substitution |
| --- | --- |
| Ala | Ser |
| Arg | Lys |
| Asn | Gln; His |
| Asp | Glu |
| Cys | Ser |
| Gln | Asn |
| Glu | Asp |
| Gly | Pro |
| His | Asn; Gln |
| Ile | Leu; Val |
| Leu | Ile; Val |
| Lys | Arg; Gln; Glu |
| Met | Leu; Ile |
| Phe | Met; Leu; Tyr |
| Ser | Thr |
| Thr | Ser |
| Trp | Tyr |
| Tyr | Trp; Phe |
| Val | Ile; Leu |

"Functional equivalents" in the above sense are also "precursors" of the polypeptides described, as well as "functional derivatives" and "salts" of the polypeptides.

"Precursors" are in that case natural or synthetic precursors of the polypeptides with or without the desired biological activity.

The expression "salts" means salts of carboxyl groups as well as salts of acid addition of amino groups of the protein molecules according to the invention. Salts of carboxyl groups can be produced in a known way and comprise inorganic salts, for example sodium, calcium, ammonium, iron and zinc salts, and salts with organic bases, for example amines, such as triethanolamine, arginine, lysine, piperidine and the like. Salts of acid addition, for example salts with inorganic acids, such as hydrochloric acid or sulfuric acid and salts with organic acids, such as acetic acid and oxalic acid, are also covered by the invention.

"Functional derivatives" of polypeptides according to the invention can also be produced on functional amino acid side groups or at their N-terminal or C-terminal end using known techniques. Such derivatives comprise for example aliphatic esters of carboxylic acid groups, amides of carboxylic acid groups, obtainable by reaction with ammonia or with a primary or secondary amine; N-acyl derivatives of free amino groups, produced by reaction with acyl groups; or O-acyl derivatives of free hydroxy groups, produced by reaction with acyl groups.

"Functional equivalents" naturally also comprise polypeptides that can be obtained from other organisms, as well as naturally occurring variants. For example, areas of homologous sequence regions can be established by sequence comparison, and equivalent enzymes can be determined on the basis of the concrete parameters of the invention.

"Functional equivalents" also comprise fragments, preferably individual domains or sequence motifs, of the polypeptides according to the invention, which for example display the desired biological function.

"Functional equivalents" are, moreover, fusion proteins, which have one of the polypeptide sequences stated above or functional equivalents derived there from and at least one further, functionally different, heterologous sequence in functional N-terminal or C-terminal association (i.e. without substantial mutual functional impairment of the fusion protein parts). Non-limiting examples of these heterologous sequences are e.g. signal peptides, histidine anchors or enzymes.

"Functional equivalents" that are also included according to the invention are homologues of the concretely disclosed proteins. These possess percent identity values as stated above. Said values refer to the identity with the concretely disclosed amino acid sequences, and may be calculated according to the algorithm of Pearson and Lipman, Proc. Natl. Acad, Sci. (USA) 85(8), 1988, 2444-2448.

The % identity values may also be calculated from BLAST alignments, algorithm blastp (protein-protein BLAST) or by applying the Clustal setting as given below.

A percentage identity of a homologous polypeptide according to the invention means in particular the percentage identity of the amino acid residues relative to the total length of one of the amino acid sequences concretely described herein.

In the case of a possible protein glycosylation, "functional equivalents" according to the invention comprise proteins of the type designated above in deglycosylated or glycosylated form as well as modified forms that can be obtained by altering the glycosylation pattern.

Such functional equivalents or homologues of the proteins or polypeptides according to the invention can be produced by mutagenesis, e.g. by point mutation, lengthening or shortening of the protein.

Such functional equivalents or homologues of the proteins according to the invention can be identified by screening combinatorial databases of mutants, for example shortening mutants. For example, a variegated database of protein variants can be produced by combinatorial mutagenesis at the nucleic acid level, e.g. by enzymatic ligation of a mixture of synthetic oligonucleotides. There are a great many methods that can be used for the production of databases of potential homologues from a degenerated oligonucleotide sequence. Chemical synthesis of a degenerated gene sequence can be carried out in an automatic DNA synthesizer, and the synthetic gene can then be ligated in a suitable expression vector. The use of a degenerated genome makes it possible to supply all sequences in a mixture, which code for the desired set of potential protein sequences. Methods of synthesis of degenerated oligonucleotides are known to a person skilled in the art (e.g. Narang, S. A. (1983) Tetrahedron 39:3; Itakura et al. (1984) Annu. Rev. Biochem. 53:323; Itakura et al., (1984) Science 198:1056; Ike et al. (1983) Nucleic Acids Res. 11:477).

In the prior art, several techniques are known for the screening of gene products of combinatorial databases, which were produced by point mutations or shortening, and for the screening of cDNA libraries for gene products with a selected property. These techniques can be adapted for the rapid screening of the gene banks that were produced by combinatorial mutagenesis of homologues according to the invention. The techniques most frequently used for the screening of large gene banks, which are based on a high-throughput analysis, comprise cloning of the gene bank in expression vectors that can be replicated, transformation of the suitable cells with the resultant vector database and expression of the combinatorial genes in conditions in which detection of the desired activity facilitates isolation of the vector that codes for the gene whose product was detected. Recursive Ensemble Mutagenesis (REM), a technique that increases the frequency of functional mutants in the databases, can be used in combination with the screening tests, in order to identify homologues (Arkin and Yourvan (1992) PNAS 89:7811-7815; Delgrave et al. (1993) Protein Engineering 6(3):327-331).

5. Coding Nucleic Acid Sequences

The invention also relates to nucleic acid sequences that code for enzymes and mutants as defined herein.

The present invention also relates to nucleic acids with a certain degree of "identity" to the sequences specifically disclosed herein. "Identity" between two nucleic acids means identity of the nucleotides, in each case over the entire length of the nucleic acid.

For example the identity may be calculated by means of the Vector NTI Suite 7.1 program of the company Informax (USA) employing the Clustal Method (Higgins D G, Sharp P M. Fast and sensitive multiple sequence alignments on a microcomputer. Comput Appl. Biosci. 1989 April; 5(2):151-1) with the following settings:

Multiple alignment parameter:

| | |
|---|---|
| Gap opening penalty | 10 |
| Gap extension penalty | 10 |
| Gap separation penalty range | 8 |
| Gap separation penalty | off |
| % identity for alignment delay | 40 |
| Residue specific gaps | off |
| Hydrophilic residue gap | off |
| Transition weighing | 0 |

Pairwise alignment parameter:

| | |
|---|---|
| FAST algorithm | on |
| K-tuple size | 1 |
| Gap penalty | 3 |
| Window size | 5 |
| Number of best diagonals | 5 |

Alternatively the identity may be determined according to Chema, Ramu, Sugawara, Hideaki, Koike, Tadashi, Lopez, Rodrigo, Gibson, Toby J, Higgins, Desmond G, Thompson, Julie D. Multiple sequence alignment with the Clustal series of programs. (2003) Nucleic Acids Res 31 (13):3497-500, the web page: http://www.ebi.ac.uk/Tools/clustalw/index.html: and the following settings

| | |
|---|---|
| DNA Gap Open Penalty | 15.0 |
| DNA Gap Extension Penalty | 6.66 |
| DNA Matrix | Identity |
| Protein Gap Open Penalty | 10.0 |
| Protein Gap Extension Penalty | 0.2 |
| Protein matrix | Gonnet |
| Protein/DNA ENDGAP | −1 |
| Protein/DNA GAPDIST | 4 |

All the nucleic acid sequences mentioned herein (single-stranded and double-stranded DNA and RNA sequences, for example cDNA and mRNA) can be produced in a known way by chemical synthesis from the nucleotide building blocks, e.g. by fragment condensation of individual overlapping, complementary nucleic acid building blocks of the double helix. Chemical synthesis of oligonucleotides can, for example, be performed in a known way, by the phosphoamidite method (Voet, Voet, 2nd edition, Wiley Press, New York, pages 896-897). The accumulation of synthetic oligonucleotides and filling of gaps by means of the Klenow fragment of DNA polymerase and ligation reactions as well as general cloning techniques are described in Sambrook et al. (1989), see below.

The invention also relates to nucleic acid sequences (single-stranded and double-stranded DNA and RNA sequences, e.g. cDNA and mRNA), coding for one of the above polypeptides and their functional equivalents, which can be obtained for example using artificial nucleotide analogs.

The invention relates both to isolated nucleic acid molecules, which code for polypeptides or proteins according to the invention or biologically active segments thereof, and to nucleic acid fragments, which can be used for example as hybridization probes or primers for identifying or amplifying coding nucleic acids according to the invention.

The nucleic acid molecules according to the invention can in addition contain non-translated sequences from the 3' and/or 5' end of the coding genetic region.

The invention further relates to the nucleic acid molecules that are complementary to the concretely described nucleotide sequences or a segment thereof.

The nucleotide sequences according to the invention make possible the production of probes and primers that can be used for the identification and/or cloning of homologous sequences in other cellular types and organisms. Such probes or primers generally comprise a nucleotide sequence region which hybridizes under "stringent" conditions (see below) on at least about 12, preferably at least about 25, for example about 40, 50 or 75 successive nucleotides of a sense strand of a nucleic acid sequence according to the invention or of a corresponding antisense strand.

An "isolated" nucleic acid molecule is separated from other nucleic acid molecules that are present in the natural source of the nucleic acid and can moreover be substantially free from other cellular material or culture medium, if it is being produced by recombinant techniques, or can be free from chemical precursors or other chemicals, if it is being synthesized chemically.

A nucleic acid molecule according to the invention can be isolated by means of standard techniques of molecular biology and the sequence information supplied according to the invention. For example, cDNA can be isolated from a suitable cDNA library, using one of the concretely disclosed complete sequences or a segment thereof as hybridization probe and standard hybridization techniques (as described for example in Sambrook, J., Fritsch, E. F. and Maniatis, T. Molecular Cloning: A Laboratory Manual. 2nd edition, Cold Spring Harbor Laboratory, Cold Spring Harbor Laboratory Press, Cold Spring Harbor, N.Y., 1989). In addition, a nucleic acid molecule comprising one of the disclosed sequences or a segment thereof, can be isolated by the polymerase chain reaction, using the oligonucleotide primers that were constructed on the basis of this sequence. The nucleic acid amplified in this way can be cloned in a suitable vector and can be characterized by DNA sequencing. The oligonucleotides according to the invention can also be produced by standard methods of synthesis, e.g. using an automatic DNA synthesizer.

Nucleic acid sequences according to the invention or derivatives thereof, homologues or parts of these sequences, can for example be isolated by usual hybridization techniques or the PCR technique from other bacteria, e.g. via genomic or cDNA libraries. These DNA sequences hybridize in standard conditions with the sequences according to the invention.

"Hybridize" means the ability of a polynucleotide or oligonucleotide to bind to an almost complementary sequence in standard conditions, whereas nonspecific binding does not occur between non-complementary partners in these conditions. For this, the sequences can be 90-100% complementary. The property of complementary sequences of being able to bind specifically to one another is utilized for example in Northern Blotting or Southern Blotting or in primer binding in PCR or RT-PCR.

Short oligonucleotides of the conserved regions are used advantageously for hybridization. However, it is also possible to use longer fragments of the nucleic acids according to the invention or the complete sequences for the hybridization. These standard conditions vary depending on the nucleic acid used (oligonucleotide, longer fragment or complete sequence) or depending on which type of nucleic acid—DNA or RNA—is used for hybridization. For example, the melting temperatures for DNA:DNA hybrids are approx. 10° C. lower than those of DNA:RNA hybrids of the same length.

For example, depending on the particular nucleic acid, standard conditions mean temperatures between 42 and 58° C. in an aqueous buffer solution with a concentration between 0.1 to 5×SSC (1×SSC=0.15 M NaCl, 15 mM sodium citrate, pH 7.2) or additionally in the presence of 50% formamide, for example 42° C. in 5×SSC, 50% formamide. Advantageously, the hybridization conditions for DNA:DNA hybrids are 0.1× SSC and temperatures between about 20° C. to 45° C., preferably between about 30° C. to 45° C. For DNA:RNA hybrids the hybridization conditions are advantageously 0.1×SSC and temperatures between about 30° C. to 55° C., preferably between about 45° C. to 55° C. These stated temperatures for hybridization are examples of calculated melting temperature values for a nucleic acid with a length of approx. 100 nucleotides and a G+C content of 50% in the absence of formamide. The experimental conditions for DNA hybridization are described in relevant genetics textbooks, for example Sambrook et al., 1989, and can be calculated using formulae that are known by a person skilled in the art, for example depending on the length of the nucleic acids, the type of hybrids or the G+C content. A person skilled in the art can obtain further information on hybridization from the following textbooks: Ausubel et al. (eds), 1985, Current Protocols in Molecular Biology, John Wiley & Sons, New York; Hames and Higgins (eds), 1985, Nucleic Acids Hybridization: A Practical Approach, IRL Press at Oxford University Press, Oxford; Brown (ed), 1991, Essential Molecular Biology: A Practical Approach, IRL Press at Oxford University Press, Oxford.

"Hybridization" can in particular be carried out under stringent conditions. Such hybridization conditions are for example described in Sambrook, J., Fritsch, E. F., Maniatis, T., in: Molecular Cloning (A Laboratory Manual), 2nd edition, Cold Spring Harbor Laboratory Press, 1989, pages 9.31-9.57 or in Current Protocols in Molecular Biology, John Wiley & Sons, N.Y. (1989), 6.3.1-6.3.6.

"Stringent" hybridization conditions mean in particular: Incubation at 42° C. overnight in a solution consisting of 50% formamide, 5×SSC (750 mM NaCl, 75 mM tri-sodium citrate), 50 mM sodium phosphate (pH 7.6), 5×Denhardt Solution, 10% dextran sulfate and 20 g/ml denatured, sheared salmon sperm DNA, followed by washing of the filters with 0.1×SSC at 65° C.

The invention also relates to derivatives of the concretely disclosed or derivable nucleic acid sequences.

Thus, further nucleic acid sequences according to the invention can be derived from the sequences specifically disclosed herein and can differ from it by addition, substitution, insertion or deletion of individual or several nucleotides, and furthermore code for polypeptides with the desired profile of properties.

The invention also encompasses nucleic acid sequences that comprise so-called silent mutations or have been altered, in comparison with a concretely stated sequence, according to the codon usage of a special original or host organism, as well as naturally occurring variants, e.g. splicing variants or allelic variants, thereof.

It also relates to sequences that can be obtained by conservative nucleotide substitutions (i.e. the amino acid in question is replaced by an amino acid of the same charge, size, polarity and/or solubility).

The invention also relates to the molecules derived from the concretely disclosed nucleic acids by sequence polymorphisms. These genetic polymorphisms can exist between individuals within a population owing to natural variation. These natural variations usually produce a variance of 1 to 5% in the nucleotide sequence of a gene.

Derivatives of nucleic acid sequences according to the invention mean for example allelic variants, having at least 60% homology at the level of the derived amino acid, preferably at least 80% homology, quite especially preferably at least 90% homology over the entire sequence range (regarding homology at the amino acid level, reference should be made to the details given above for the polypeptides). Advantageously, the homologies can be higher over partial regions of the sequences.

Furthermore, derivatives are also to be understood to be homologues of the nucleic acid sequences according to the invention, for example animal, plant, fungal or bacterial homologues, shortened sequences, single-stranded DNA or RNA of the coding and noncoding DNA sequence. For example, homologues have, at the DNA level, a homology of at least 40%, preferably of at least 60%, especially preferably of at least 70%, quite especially preferably of at least 80% over the entire DNA region given in a sequence specifically disclosed herein.

Moreover, derivatives are to be understood to be, for example, fusions with promoters. The promoters that are added to the stated nucleotide sequences can be modified by at least one nucleotide exchange, at least one insertion, inversion and/or deletion, though without impairing the functionality or efficacy of the promoters. Moreover, the efficacy of the promoters can be increased by altering their sequence or can be exchanged completely with more effective promoters even of organisms of a different genus.

6. Constructs According to the Invention

The invention also relates to expression constructs, containing, under the genetic control of regulatory nucleic acid sequences, a nucleic acid sequence coding for a polypeptide or fusion protein according to the invention; as well as vectors comprising at least one of these expression constructs.

"Expression unit" means, according to the invention, a nucleic acid with expression activity, which comprises a promoter as defined herein and, after functional association with a nucleic acid that is to be expressed or a gene, regulates the expression, i.e. the transcription and the translation of this nucleic acid or of this gene. In this context, therefore, it is also called a "regulatory nucleic acid sequence". In addition to the promoter, other regulatory elements may be present, e.g. enhancers.

"Expression cassette" or "expression construct" means, according to the invention, an expression unit, which is functionally associated with the nucleic acid that is to be expressed or the gene that is to be expressed. In contrast to an expression unit, an expression cassette thus comprises not only nucleic acid sequences, which regulate transcription and translation, but also the nucleic acid sequences, which should be expressed as protein as a result of the transcription and translation.

The terms "expression" or "overexpression" describe, in the context of the invention, the production or increase of intracellular activity of one or more enzymes in a microorganism, which are encoded by the corresponding DNA. For this, it is possible for example to insert a gene in an organism, replace an existing gene by another gene, increase the number of copies of the gene or genes, use a strong promoter or use a gene that codes for a corresponding enzyme with a high activity, and optionally these measures can be combined.

Preferably such constructs according to the invention comprise a promoter 5'-upstream from the respective coding sequence, and a terminator sequence 3'-downstream, and optionally further usual regulatory elements, in each case functionally associated with the coding sequence.

A "promoter", a "nucleic acid with promoter activity" or a "promoter sequence" mean, according to the invention, a nucleic acid that, functionally associated with a nucleic acid that is to be transcribed, regulates the transcription of this nucleic acid.

"Functional" or "operative" association means, in this context, for example the sequential arrangement of one of the nucleic acids with promoter activity and of a nucleic acid sequence that is to be transcribed and optionally further regulatory elements, for example nucleic acid sequences that enable the transcription of nucleic acids, and for example a terminator, in such a way that each of the regulatory elements can fulfill its function in the transcription of the nucleic acid sequence. This does not necessarily require a direct association in the chemical sense. Genetic control sequences, such as enhancer sequences, can also exert their function on the target sequence from more remote positions or even from other DNA molecules. Arrangements are preferred in which the nucleic acid sequence that is to be transcribed is positioned behind (i.e. at the 3' end) the promoter sequence, so that the two sequences are bound covalently to one another. The distance between the promoter sequence and the nucleic acid sequence that is to be expressed transgenically can be less than 200 bp (base pairs), or less than 100 bp or less than 50 bp.

Apart from promoters and terminators, examples of other regulatory elements that may be mentioned are targeting sequences, enhancers, polyadenylation signals, selectable markers, amplification signals, replication origins and the like. Suitable regulatory sequences are described for example in Goeddel, Gene Expression Technology: Methods in Enzymology 185, Academic Press, San Diego, Calif. (1990).

Nucleic acid constructs according to the invention comprise in particular sequences selected from those, specifically mentioned herein or derivatives and homologues thereof, as well as the nucleic acid sequences that can be derived from amino acid sequences specifically mentioned herein which are advantageously associated operatively or functionally with one or more regulating signal for controlling, e.g. increasing, gene expression.

In addition to these regulatory sequences, the natural regulation of these sequences can still be present in front of the actual structural genes and optionally can have been altered genetically, so that natural regulation is switched off and the expression of the genes has been increased. The nucleic acid construct can also be of a simpler design, i.e. without any additional regulatory signals being inserted in front of the coding sequence and without removing the natural promoter with its regulation. Instead, the natural regulatory sequence is silenced so that regulation no longer takes place and gene expression is increased.

A preferred nucleic acid construct advantageously also contains one or more of the aforementioned enhancer sequences, functionally associated with the promoter, which permit increased expression of the nucleic acid sequence. Additional advantageous sequences, such as other regulatory elements or terminators, can also be inserted at the 3' end of the DNA sequences. One or more copies of the nucleic acids according to the invention can be contained in the construct. The construct can also contain other markers, such as antibiotic resistances or auxotrophy-complementing genes, optionally for selection on the construct.

Examples of suitable regulatory sequences are contained in promoters such as cos-, tac-, trp-, tet-, trp-tet-, lpp-, lac-, lpp-lac-, lacI$^{q}$-, T7-, T5-, T3-, gal-, trc-, ara-, rhaP (rhaP$_{BAD}$) SP6-, lambda-P$_R$- or in the lambda-P$_L$ promoter, which find application advantageously in Gram-negative bacteria. Other advantageous regulatory sequences are contained for example in the Gram-positive promoters ace, amy and SPO2, in the yeast or fungal promoters ADC1, MFalpha, AC, P-60, CYC1, GAPDH, TEF, rp28, ADH. Artificial promoters can also be used for regulation.

For expression, the nucleic acid construct is inserted in a host organism advantageously in a vector, for example a plasmid or a phage, which permits optimum expression of the genes in the host. In addition to plasmids and phages, vectors are also to be understood as meaning all other vectors known to a person skilled in the art, e.g. viruses, such as SV40, CMV, baculovirus and adenovirus, transposons, IS elements, phasmids, cosmids, and linear or circular DNA. These vectors can be replicated autonomously in the host organism or can be replicated chromosomally. These vectors represent a further embodiment of the invention.

Suitable plasmids are, for example in *E. coli*, pLG338, pACYC184, pBR322, pUC18, pUC19, pKC30, pRep4, pHS1, pKK223-3, pDHE19.2, pHS2, pPLc236, pMBL24, pLG200, pUR290, pIN-III$^{113}$-B1, λgt11 or pBdCI; in nocardioform actinomycetes pJAM2; in *Streptomyces* pIJ101, pIJ364, pIJ702 or pIJ361; in *bacillus* pUB110, pC194 or pBD214; in *Corynebacterium* pSA77 or pAJ667; in fungi pALS1, pIL2 or pBB116; in yeasts 2alphaM, pAG-1, YEp6, YEp13 or pEMBLYe23 or in plants pLGV23, pGHlac$^+$, pBIN19, pAK2004 or pDH51. The aforementioned plasmids represent a small selection of the possible plasmids. Other plasmids are well known to a person skilled in the art and will be found for example in the book Cloning Vectors (Eds. Pouwels P. H. et al. Elsevier, Amsterdam-New York-Oxford, 1985, ISBN 0 444 904018).

In a further embodiment of the vector, the vector containing the nucleic acid construct according to the invention or the nucleic acid according to the invention can be inserted advantageously in the form of a linear DNA in the microorganisms and integrated into the genome of the host organism through heterologous or homologous recombination. This linear DNA can comprise a linearized vector such as plasmid or just the nucleic acid construct or the nucleic acid according to the invention.

For optimum expression of heterologous genes in organisms, it is advantageous to alter the nucleic acid sequences in accordance with the specific codon usage employed in the organism. The codon usage can easily be determined on the basis of computer evaluations of other, known genes of the organism in question.

The production of an expression cassette according to the invention is based on fusion of a suitable promoter with a suitable coding nucleotide sequence and a terminator signal or polyadenylation signal. Common recombination and cloning techniques are used for this, as described for example in T. Maniatis, E. F. Fritsch and J. Sambrook, Molecular Cloning: A Laboratory Manual, Cold Spring Harbor Laboratory, Cold Spring Harbor, N.Y. (1989) as well as in T. J. Silhavy, M. L. Berman and L. W. Enquist, Experiments with Gene Fusions, Cold Spring Harbor Laboratory, Cold Spring Harbor, N.Y.

(1984) and in Ausubel, F. M. et al., Current Protocols in Molecular Biology, Greene Publishing Assoc. and Wiley Interscience (1987).

The recombinant nucleic acid construct or gene construct is inserted advantageously in a host-specific vector for expression in a suitable host organism, to permit optimum expression of the genes in the host. Vectors are well known to a person skilled in the art and will be found for example in "Cloning Vectors" (Pouwels P. H. et al., Publ. Elsevier, Amsterdam-New York-Oxford, 1985).

7. Hosts that can be Used According to the Invention

Depending on the context, the term "microorganism" means the starting microorganism (wild-type) or a genetically modified microorganism according to the invention, or both.

The term "wild-type" means, according to the invention, the corresponding starting microorganism, and need not necessarily correspond to a naturally occurring organism.

By means of the vectors according to the invention, recombinant microorganisms can be produced, which have been transformed for example with at least one vector according to the invention and can be used for production of the polypeptides according to the invention. Advantageously, the recombinant constructs according to the invention, described above, are inserted in a suitable host system and expressed. Preferably, common cloning and transfection methods that are familiar to a person skilled in the art are used, for example co-precipitation, protoplast fusion, electroporation, retroviral transfection and the like, in order to secure expression of the stated nucleic acids in the respective expression system. Suitable systems are described for example in Current Protocols in Molecular Biology, F. Ausubel et al., Publ. Wiley Interscience, New York 1997, or Sambrook et al. Molecular Cloning: A Laboratory Manual. 2nd edition, Cold Spring Harbor Laboratory, Cold Spring Harbor Laboratory Press, Cold Spring Harbor, N.Y., 1989.

In principle, all prokaryotic organisms can be considered as recombinant host organisms for the nucleic acid according to the invention or the nucleic acid construct. Bacteria are used advantageously as host organisms. Preferably they are selected from native or recombinant bacteria having the ability to produce inclusion bodies of the PHA-, TAG- or WE-type, as in particular the TAG-producing nocardioform actinomycetes, in particular of the genus *Rhodococcus, Mycobacterium, Nocardia, Gordonia, Skermania* and *Tsukamurella*; as well as TAG-producing Streptomycetes; WE-producing genera *Acinetobacter* and *Alcanivorax*; as well as recombinant strains of the genus *Escherichia*, especially *E. coli, Corynebacterium*, especially *C. glutamicum* and *Bacillus*, especially *B. subtilis*.

The host organism or host organisms according to the invention then preferably contain at least one of the nucleic acid sequences, nucleic acid constructs or vectors described in this invention, which code for an enzyme activity according to the above definition.

The organisms used in the method according to the invention are grown or bred in a manner familiar to a person skilled in the art, depending on the host organism. As a rule, microorganisms are grown in a liquid medium, which contains a source of carbon, generally in the form of sugars, a source of nitrogen generally in the form of organic sources of nitrogen such as yeast extract or salts such as ammonium sulfate, trace elements such as iron, manganese and magnesium salts and optionally vitamins, at temperatures between 0° C. and 100° C., preferably between 10° C. to 60° C. with oxygen aeration.

The pH of the liquid nutrient medium can be maintained at a fixed value, i.e. regulated or not regulated during growing. Growing can be carried out batchwise, semi-batchwise or continuously. Nutrients can be supplied at the start of fermentation or can be supplied subsequently, either semi-continuously or continuously.

8. Recombinant Production of Enzymes of the Invention

The invention also relates to methods for production of proteins according to the invention by cultivating a microorganism which expresses said protein, and isolating the desired product from the culture.

The microorganisms as used according to the invention can be cultivated continuously or discontinuously in the batch process or in the fed batch or repeated fed batch process. A review of known methods of cultivation will be found in the textbook by Chmiel (Bioprocesstechnik 1. Einführung in die Bioverfahrenstechnik (Gustav Fischer Verlag, Stuttgart, 1991)) or in the textbook by Storhas (Bioreaktoren and periphere Einrichtungen (Vieweg Verlag, Braunschweig/Wiesbaden, 1994)).

The culture medium that is to be used must satisfy the requirements of the particular strains in an appropriate manner. Descriptions of culture media for various microorganisms are given in the handbook "Manual of Methods for General Bacteriology" of the American Society for Bacteriology (Washington D.C., USA, 1981).

These media that can be used according to the invention generally comprise one or more sources of carbon, sources of nitrogen, inorganic salts, vitamins and/or trace elements.

Preferred sources of carbon are sugars, such as mono-, di- or polysaccharides. Very good sources of carbon are for example glucose, fructose, mannose, galactose, ribose, sorbose, ribulose, lactose, maltose, sucrose, raffinose, starch or cellulose. Sugars can also be added to the media via complex compounds, such as molasses, or other by-products from sugar refining. It may also be advantageous to add mixtures of various sources of carbon. Other possible sources of carbon are oils and fats such as soybean oil, sunflower oil, peanut oil and coconut oil, fatty acids such as palmitic acid, stearic acid or linoleic acid, alcohols such as glycerol, methanol or ethanol and organic acids such as acetic acid or lactic acid.

Sources of nitrogen are usually organic or inorganic nitrogen compounds or materials containing these compounds. Examples of sources of nitrogen include ammonia gas or ammonium salts, such as ammonium sulfate, ammonium chloride, ammonium phosphate, ammonium carbonate or ammonium nitrate, nitrates, urea, amino acids or complex sources of nitrogen, such as corn-steep liquor, soybean flour, soybean protein, yeast extract, meat extract and others. The sources of nitrogen can be used separately or as a mixture.

Inorganic salt compounds that may be present in the media comprise the chloride, phosphate or sulfate salts of calcium, magnesium, sodium, cobalt, molybdenum, potassium, manganese, zinc, copper and iron.

Inorganic sulfur-containing compounds, for example sulfates, sulfites, dithionites, tetrathionates, thiosulfates, sulfides, but also organic sulfur compounds, such as mercaptans and thiols, can be used as sources of sulfur.

Phosphoric acid, potassium dihydrogenphosphate or dipotassium hydrogenphosphate or the corresponding sodium-containing salts can be used as sources of phosphorus.

Chelating agents can be added to the medium, in order to keep the metal ions in solution. Especially suitable chelating agents comprise dihydroxyphenols, such as catechol or protocatechuate, or organic acids, such as citric acid.

The fermentation media used according to the invention may also contain other growth factors, such as vitamins or growth promoters, which include for example biotin, riboflavin, thiamine, folic acid, nicotinic acid, pantothenate and pyridoxine. Growth factors and salts often come from complex components of the media, such as yeast extract, molasses, corn-steep liquor and the like. In addition, suitable precursors can be added to the culture medium. The precise composition of the compounds in the medium is strongly dependent on the particular experiment and must be decided individually for each specific case. Information on media optimization can be found in the textbook "Applied Microbiol. Physiology, A Practical Approach" (Publ. P. M. Rhodes, P. F. Stanbury, IRL Press (1997) p. 53-73, ISBN 0 19 963577 3). Growing media can also be obtained from commercial suppliers, such as Standard 1 (Merck) or BHI (Brain heart infusion, DIFCO) etc.

All components of the medium are sterilized, either by heating (20 min at 1.5 bar and 121° C.) or by sterile filtration. The components can be sterilized either together, or if necessary separately. All the components of the medium can be present at the start of growing, or optionally can be added continuously or by batch feed.

The temperature of the culture is normally between 15° C. and 45° C., preferably 25° C. to 40° C. and can be kept constant or can be varied during the experiment. The pH value of the medium should be in the range from 5 to 8.5, preferably around 7.0. The pH value for growing can be controlled during growing by adding basic compounds such as sodium hydroxide, potassium hydroxide, ammonia or ammonia water or acid compounds such as phosphoric acid or sulfuric acid. Antifoaming agents, e.g. fatty acid polyglycol esters, can be used for controlling foaming. To maintain the stability of plasmids, suitable substances with selective action, e.g. antibiotics, can be added to the medium. Oxygen or oxygen-containing gas mixtures, e.g. the ambient air, are fed into the culture in order to maintain aerobic conditions. The temperature of the culture is normally from 20° C. to 45° C. Culture is continued until a maximum of the desired product has formed. This is normally achieved within 10 hours to 160 hours.

The cells can be disrupted optionally by high-frequency ultrasound, by high pressure, e.g. in a French pressure cell, by osmolysis, by the action of detergents, lytic enzymes or organic solvents, by means of homogenizers or by a combination of several of the methods listed.

9. Reaction Conditions

The at least one enzyme which is present during the method for producing a mono-acylated polyol, can be present in living cells naturally or recombinantly producing the enzyme or enzymes, in harvested cells, in dead cells, in permeabilized cells, in crude cell extracts, in purified extracts, or in essentially pure or completely pure form. The at least one enzyme may be present in solution or as an enzyme immobilized on a carrier. One or several enzymes may simultaneously be present in soluble and immobilised form.

The method according to the invention can be performed in common reactors, which are known to those skilled in the art, and in different ranges of scale, e.g. from a laboratory scale (few milliliters to dozens of liters of reaction volume) to an industrial scale (several liters to thousands of cubic meters of reaction volume). If the lipase is used in a form encapsulated by non-living, optionally permeabilized cells, in the form of a more or less purified cell extract or in purified form, a chemical reactor can be used. The chemical reactor usually allows controlling the amount of the at least one enzyme, the amount of the at least one substrate, the pH, the temperature and the circulation of the reaction medium. When the at least one enzyme is present in living cells, the process will be a fermentation. In this case the biocatalytic production will take place in a bioreactor (fermenter), where parameters necessary for suitable living conditions for the living cells (e.g. culture medium with nutrients, temperature, aeration, presence or absence of oxygen or other gases, antibiotics, and the like) can be controlled. Those skilled in the art are familiar with chemical reactors or bioreactors, e.g. with procedures for up-scaling chemical or biotechnological methods from laboratory scale to industrial scale, or for optimizing process parameters, which are also extensively described in the literature (for biotechnological methods see e.g. Crueger and Crueger, Biotechnologie-Lehrbuch der angewandten Mikrobiologie, 2. Ed., R. Oldenbourg Verlag, München, Wien, 1984).

Cells containing the at least one lopase can be permeabilized by physical or mechanical means, such as ultrasound or radiofrequency pulses, French presses, or chemical means, such as hypotonic media, lytic enzymes and detergents present in the medium, or combination of such methods. Examples for detergents are digitonin, n-dodecylmaltoside, octylglycoside, Triton® X-100, Tween® 20, deoxycholate, CHAPS (3-[(3-Cholamidopropyl)dimethylammonio]-1-propansulfonate), Nonidet® P40 (Ethylphenolpoly(ethyleneglycolether), and the like.

If the at least one enzyme is immobilised, it is attached to an inert carrier. Suitable carrier materials are known in the art and are, e.g., disclosed in EP-A-1149849, EP-A-1 069 183 and DE-OS100193773 as well as the literature references cited therein (all of which are specifically enclosed with regard to carrier materials). Examples for suitable carrier materials are clays, clay minerals such as kaolinite, diatomeceous earth, perlite, silica, alumina, sodium carbonate, calcium carbonate, cellulose powder, anion exchanger materials, synthetic polymers, such as polystyrene, acrylic resins, phenol formaldehyde resins, polyurethanes and polyolefins, such as polyethylene and polypropylene. For preparing carrier-bound enzymes the carrier materials usually are used in the form of fine powders, wherein porous forms are preferred. The particle size of the carrier material usually does not exceed 5 mm, in particular 2 mm. In case the at least one enzyme is present in a whole-cell-preparation, said whole-cell-preparation may be present in a free or immobilised form. Suitable carrier materials are e.g. Ca-alginate or Carrageenan. Enzymes as well as cells may directly be linked by glutaraldehyde. A wide range of immobilisation methods is known in the art (e.g. J. Lalonde and A. Margolin "Immobilization of Enzymes" in K. Drauz and H. Waldmann, Enzyme Catalysis in Organic Synthesis 2002, Vol. III, 991-1032, Wiley-VCH, Weinheim).

The conversion reaction can be carried out batch wise, semi-batch wise or continuously. Reactants (and optionally nutrients) can be supplied at the start of reaction or can be supplied subsequently, either semi-continuously or continuously.

The reaction may be performed in an aqueous or non-aqueous reaction medium.

An aqueous medium may contain a suitable buffer in order to adjust the pH to a value in the range of 5 to 9, like 6 to 8.

The non-aqueous medium may contain is substantially free of water, i.e. will contain less that about 1 wt.-% (weight percent) or 0.5 wt.-% of water.

In particular, the present method is performed in an organic non-aqueous medium. As suitable organic solvents there may be mentioned aliphatic carbohydrates having for example 5 to 8 carbon atoms, like pentane, cyclopentane, hexane, cyclohexane, heptane, octane or cyclooctane, halogenated aliphatic carbohydrates like dichloromethane, chloroformate, $CCl_4$, dichloroethane or tetrachloroethane, aromatic carbohydrates, like benzene, toluene, xyloles, chlorobenzene or dichlorobenzene, aliphatic acyclic and cyclic ethers. Like diethylether, methyl-tert.-butylether, ethyl-tert.-butylether, dipropylether, ddiisopropylether, dibutylether, tetrahydrofuran or esters like ethylacetate or n-butylacetate or ketones like methylisobutylketone or dioxan or mixtures thereof.

Particularly useful are solvents, which may also function as reactants, like the acyl donor ethyl acetate.

The concentration of the reactants may be adapted to the optimum reaction conditions, which may depend on the specific enzyme applied. For example, the initial substrate concentration may be in the range of 0.01 to 0.5 M, as for example 10 to 100 mM.

If appropriate one reactant, as for example the acyl donor may be used in molar excess in order to shift the reaction equilibrium to the side of the product.

The reaction temperature may be adapted to the optimum reaction conditions, which may depend on the specific enzyme applied. For example, the reaction may be performed at a temperature in a range of from 0 to 70° C., as for example 20 to 50 or 25 to 40° C. Examples for reaction temperatures are about 30° C., about 35° C., about 37° C., about 40° C., about 45° C., about 50° C., about 55° C. and about 60° C.

The process may proceed until equilibrium between the substrate and then product(s) is achieved, but may be stopped earlier. Usual process times are in the range from 1 minute to 25 hours, in particular 10 min to 6 hours, as for example in the range from 1 hour to 4 hours, in particular 1.5 hours to 3.5 hours.

10. Product Isolation

The methodology of the present invention can further include a step of recovering an acylated product, optionally in stereoisomerically or enantiomerically substantially pure form. The term "recovering" includes extracting, harvesting, isolating or purifying the compound from culture or reaction media. Recovering the compound can be performed according to any conventional isolation or purification methodology known in the art including, but not limited to, treatment with a conventional resin (e.g., anion or cation exchange resin, non-ionic adsorption resin, etc.), treatment with a conventional adsorbent (e.g., activated charcoal, silicic acid, silica gel, cellulose, alumina, etc.), alteration of pH, solvent extraction (e.g., with a conventional solvent such as an alcohol, ethyl acetate, hexane and the like), distillation, dialysis, filtration, concentration, crystallization, recrystallization, pH adjustment, lyophilization and the like.

Identity and purity of the isolated product may be determined by known techniques, like High Performance Liquid Chromatography (HPLC), gas chromatography (GC), Spektroskopy (like IR, UV, NMR), Colouring methods, TLC, NIRS, enzymatic or microbial assays. (see for example: Patek et al. (1994) Appl. Environ. Microbiol. 60:133-140; Malakhova et al. (1996) Biotekhnologiya 11 27-32; und Schmidt et al. (1998) Bioprocess Engineer. 19:67-70. Ullmann's Encyclopedia of Industrial Chemistry (1996) Bd. A27, VCH: Weinheim, S. 89-90, S. 521-540, S. 540-547, S. 559-566, 575-581 und S. 581-587; Michal, G (1999) Biochemical Pathways: An Atlas of Biochemistry and Molecular Biology, John Wiley and Sons; Fallon, A. et al. (1987) Applications of HPLC in Biochemistry in: Laboratory Techniques in Biochemistry and Molecular Biology, Bd. 17.)

The following examples only serve to illustrate the invention. The numerous possible variations that are obvious to a person skilled in the art also fall within the scope of the invention.

EXPERIMENTAL PART

A. Materials and Methods

1. Enzyme Immobilisation 5 g of Accurel <1500 micron MP1000/pp powder was used. The powder was soaked in 95% ethanol during 5 days. The powder was washed again in fresh ethanol, which was removed, prior to incubation. 21 ml of T40A mutated CALB of an approximate concentration of 2.7 mg/ml, dissolved in 100 mM $PO_4$ buffer, pH 7.2 were added.

Enzyme-containing supernatant from *P. pastoris* cultivation was concentrated to 3 g/l protein concentration. The pH was adjusted to 7.5. 100 g Resindion Diaoin HP 20 L beads were added per liter of enzyme solution. The slurry was incubated under shaking for 4 h. Then the solid was filtered off and dried in a slight air stream.

For the T40V mutated CALB, 5 g of Accurel <1500 micron MP1000/pp powder was used. The powder was soaked in 95% ethanol for >1 hour and then washed with fresh ethanol. The powder was washed with buffer, 100 mM $K_xH_yPO_4$, pH 7.2, to remove ethanol before immobilization. 70 ml of protein solution of a concentration of approximately 30-50 mg/l. The immobilization solution was left on a IKA® KS basic shaker at 80 rpm in 4° C. for 3 days. The supernatant was filtered off and the beads were washed by adding 3×100 ml of 50 mM $NH_4Ac$ (pH7) over a vacuum manifold. The 50 mM $NH_4Ac$ was used because it evaporates, so that there are no large amounts of salts left on the beads.

2. GC Parameters for the Analysis of Different Constituents 2.1 Glycol

The temperature for the inlet was set at 200° C. and the detector was set to 270° C. The temperature program started at 40° C. for 5 minutes, followed by a gradient of 10° C./min to 200° C., where the temperature was kept constant for a final 10 minutes.

2.2 1,3-Propanediol

Temperatures for inlet and detector were both 200° C. The temperature program started at 40° C. for 5 minutes, followed by a gradient of 5° C./min to 160° C., followed by a gradient of 10° C./min to 200° C., where the temperature was held constant for a final 5 minutes.

2.3 1,4-Butanediol

The temperature for the inlet was switched off and the detector was set to 270° C. The temperature program started at 30° C. for 5 minutes, followed by a gradient of 2° C./min to 40° C., followed by a gradient of 10° C./min to 200° C., where the temperature was held constant for a final 5 minutes.

2.4 2-Methyl-1,3-propanediol and 2-phenyl-1,3-propanediol

The temperature for the inlet was switched off and the detector was set to 270° C. The temperature program started at 40° C. for 5 minutes, followed by a gradient of 10° C./min to 200° C., where the temperature was held constant for a final 10 minutes.

2.5. 1,2-Ethanediol and 1,4-butanediol

The following parameters were used for mutants and determinations as described in the Examples 5, 6 or 7. The temperature for the inlet was set at 200° C. and the detector was set to 200° C. The temperature program started at 40° C. for 5 minutes, followed by a gradient of 10° C./min to 200° C., where the temperature was kept constant for a final 10 minutes.

2.6. 1,4-Butanediol, 4-hydroxybutane acrylate and butanediol diacrylate

The following parameters were used for mutants and determinations as described in Examples 8 and 9. The temperature for the inlet was set at 220° C. and the detector was set to 225° C. The temperature program started at 50° C. for 5 minutes, followed by a gradient of 10° C./min to 290° C., where the temperature was kept constant for a final 10 minutes.

B. Examples

Example 1

Preparation of CALB Wild Type and T40A and T40V Mutants and Immobilization

Wild type and T40A-mutated CALB were obtained from in-house productions from earlier experiments according to previously defined protocol [Magnusson, A., K. Hult, and M. Holmquist, *Creation of an enantioselective hydrolase by engineered substrate-assisted catalysis*. Journal of the American Chemical Society, 2001. 123(18): p. 4354-4355. Rotticci-Mulder, J. C., et al., *Expression in Pichia pastoris of Candida antarctica lipase B and lipase B fused to a cellulose-binding domain*. Protein Expression and Purification, 2001. 21(3): p. 386-392.]

The primers used for T40A mutated CALB were

```
5'-GACTGGTTCCAATTGACAAGC-3'    (SEQ ID NO: 5)
and

5'-GCAAATGGCATTCTGACATCC-3'    (SEQ ID NO: 6)
```

The T40V mutated CALB was prepared using pGAPZaB CALB construct obtained from earlier studies [Larsen M. W., et al., *Expression of Candida antarctica lipase B in Pichia pastoris and various Escerichia coli systems*, Protein Expression and Purification, 2008, 62(1): p. 90-97].

25 ng template was used together with 100 ng of the primers

```
                                                 (SEQ ID NO: 7)
5'-CCCATCCTTCTCGTCCCCGGAGTCGGCACCACAGGTCCA-3'
and (SEQ ID NO: 8)
5'-GTCGAACGACTGTGGACCTGTGGTGCCGACTCCGGGGAC-3'.
```

6% DMSO was used in the PCR reaction. The reaction was carried out at 98° C. for 1 min, 25 cycles with 10 s at 98° C., 50 s at 60° C. and 3 min at 72° C. The template DNA was digested with FastDigest Dpnl. Competent cells, *Echerichia coli* strain XL 10 GOLD from Stratagene, were transformed with 3 µl of the mutagenesis reaction mixture. The mutation was confirmed by sequencing by DNA cycle sequencing with BigDye-terminators. The plasmid was extracted using QIAprep Spin Miniprep Kit and linearised with FastDigest AvrII from Fermentas. Transformation of *Pichia pastoris* X33 from invitrogen was done by electroporation following the manual: pGAPZ A, B, C and pGAPZα A, B, C using a BIORAD Gene Pulser. Cultivation was done by inoculating a single cell colony in 10 ml of media, BMGY (10 g yeast extract, 20 g peptone, 100 mL 1 M $K_2HPO_4/KH_2PO_4$ pH 6.0 per liter, 13.4 g yeast nitrogen base with ammonium sulphate without amino acids (YNB), 0.4 mg biotin, and 10 mL glycerol in 1 L water), which was cultivated in 30° C. over night with an orbital agitation of 260 rpm. 500 µl was then used to inoculate 0.5 l BMGY in 5 l shake flask. Cultivation was done at 30° C. with an orbital agitation of 260 rpm for 3 days. Harvest was done by centrifugation on a Sorvall Super T21 centrifuge and removal of the cell pellet.

Protein expressions were done in recombinant yeast *Pichia pastoris*.

Purifications of wild type and T40A CALB were done by hydrophobic interactions chromatography followed by gel filtration. A previously defined protocol were used for purification of wild type and T40A CALB [Rotticci-Mulder, J. C., et al., *Expression in Pichia pastoris of Candida antarctica lipase B and lipase B fused to a cellulose-binding domain*. Protein Expression and Purification, 2001. 21(3): p. 386-392.]. The T40V CALB was purified by ion exchange chromatography. A protocol was followed [Trodler P. et al, *Rational design of a one-step purification strategy for Candida Antarctica lipase B by ion exchange chromatography*. Journal of Chromatography A 2008 1179(2) p. 386-392] with the exception that buffer exchange was carried out by dialysis instead of crossed-flow filtration. A dialysis bag from Spectra/Por®, dialysis membrane with molecular weight cut off 14,000 Da was filled with 0.5 l of filtered culture media. The media was equilibrated with 4×1.5 l of buffer, 10 mM sodium formate, 10 mM sodium citrate and 10 mM sodium acetate, pH 3.0, which was used for the ion exchange chromatography. The purification was done using 7 ml Source 15S matrix packed in a 16/20 column connected to an ÄKTA explorer.

The enzyme was immobilized on Accurel MP1000 carrier beads (see general method, above), dried and equilibrated over saturated lithium chloride. Equilibration of water activity could be achieved by storing the enzyme over lithium chloride for a few days. This T40A and wild type CALB had been stored for 3-4 years over lithium chloride since it is suitable to store immobilized CALB in this environment for a longer period of time to prevent loss of activity. The T40V CALB was stored for 3 days over lithium chloride before use.

The amount of enzyme loaded on the carriers was confirmed by active site titration using the inhibitor methyl 4-methylumbelliferyl hexylphosphonate. Inhibitor from an ampoule stored in a freezer (−20° C.) was dissolved to a concentration of 50 µM in acetonitrile. The inhibitor was previously synthesized and used for active site titration of CALB as described in Magnusson, A. O., et al., *Creating space for large secondary alcohols by rational redesign of Candida antarctica lipase B*. Chembiochem, 2005. 6(6): p. 1051-1056 and Rotticci, D., et al., *An active-site titration method for lipases*. Biochimica Et Biophysica Acta-Molecular and Cell Biology of Lipids, 2000. 1483(1): p. 132-140.

Inhibition reactions were run in three separate vials each containing 50 mg enzyme carrier beads with immobilized CALB wild type and T40A-mutant. The wild type was run in one of the reaction vials, and the other two contained T40A-mutant. The enzymes were incubated in 1 ml of 50 µM inhibitor dissolved in acetonitrile. Each vial were sealed and covered in aluminium foil, to prevent light from damaging the fluorophore, and stored in continuous end over end. Aliquots were taken after 2, 5 and 9 days. Each aliquot contained of 100 µl reaction solution from incubation dispensed in 900 µl buffer (100 mM Tris, 1 mM $CaCl_2$, pH 8.0) in a Perkin Elmer 10/4 mm quarts cuvette. Analysis was preformed by fluorescence using a Perkin Elmer LS 50 B fluorimeter. The wavelengths of excitation and emission were 360 nm and 445 nm respectively. Fluorescence was also measured in two different control samples. Inhibitor, 50 µM in acetonitrile, was incubated without enzyme for control of background fluorescence from spontaneous hydrolysis of the methyl 4-methylumbelliferyl hexylphosphonate. In addition to this, 50 mg of each enzyme was incubated in acetonitrile without inhibitor for control of any background fluorescence from the immobilized enzyme. The total fluorescence from these samples was subtracted from the fluorescence measured in the inhibition reactions. The same method was used for active site titration of immobilized CALB T40V. A sample taken and measured after two weeks of inhibition showed low levels of inhibition.

Remaining activity was measured after inhibition. The immobilized enzyme washed in 1 ml acetonitrile and stored over saturated LiCl for 3 days. A solution containing 100 mM 1-butanol, ≥99.5% from Riedel-deHaën, 20 mM decane, ≥98% from Fluka and 1 M vinyl butyrate, ≥99% from Fluka dissolved in MTBE, 99.5% from Labscan, were used as reaction solution for activity measurements. 4 ml of the reaction solution was added to inhibited enzyme. For comparison, the reaction was repeated with the enzyme used for control of background fluorescence. The amounts of enzyme used for activity measurements were adjusted to prevent high conversion of the substrate, which may affect reaction rates. The inhibited immobilized enzymes used in the reactions were 19 mg wild type and 20 mg T40A. The amounts of immobilized enzymes taken from the fluorescence controls used in the reactions were 2.8 mg of the wild type and 9.0 T40A. 5 Aliquots were taken from each reaction at reaction times between 50 and 350 seconds. Analyses were performed on GC as defined above, under the section analysis.

The activity measurements showed that 83% of the wild type and 21% of the T40A-mutant was inhibited. Remaining activity was to low to measure for CALB T40A. Taking these activities into considerations, 4.6 mg active enzyme was immobilized per g carrier beads for the T40A-mutant and 12 mg enzyme was immobilized per g carrier beads for the wild type. The amount of active CALB T40V immobilized was around 0.3 mg per g carrier beads.

Example 2

Enzyme-Catalyzed Acylation Reactions with Different Diols as Substrate and Ethyl Acetate as Acyl Donor Reactions were run with three different straight chain primary diols:
1,2-ethanediol, ≥99.5% from MERCK,
1,3-propanediol, 98% from Aldrich and
1,4-butanediol, ≥99% from Aldrich.
Additionally, reactions with 1,3-propanediol with different substitutions were run:
2-methyl-1,3-propanediol and
2-phenyl-1,3-propanediol,
3-Hexanone, ≥98% from Aldrich, was used as internal standard.

Each diol was dissolved to a concentration of 20 mM together with 5 mM of 3-hexanone in ethyl acetate, ≥99% from Fluka, which was used as acyl donor and solvent. Reactions were started by adding 4 ml reaction solution to 20 mg enzyme carrier beads loaded with either wild-type or T40A mutated CALB. Reactions were run at 29° C. on a HLC rotating thermo block. Aliquots of 50 µl were taken, filtered through wool in a Pasteur pipette and diluted with 50 µl ethyl acetate prior to analysis. The 3-hexanon used as internal standard were present in the reaction solution throughout both reaction and analysis.

5 mM 3-hexanone was used as internal standard in the reaction mixtures together with 20 mM diol. Aliquots were taken during the reaction by taking 50 µl of reaction sample. The samples were filtered though wool together with 50 µl ethyl acetate, thereby any remaining enzyme were removed and the reaction samples were diluted by a factor of 2 prior to analysis.

The reactions catalyzed by the T40A-mutant were rerun with 100 mg enzyme carrier beads for determination of maximum monoester yield. The reactions with 2-methyl-1,3-propanediol and 2-phenyl-1,3-propanediol were rerun at 100 mM concentration of diol and 50 mg enzyme carrier beads, both with CALB wild type and CALB T40A-mutant. This was done in order to determine the enantiomeric excess.

All reactions were analyzed on GC, Hewlett Packard 5890 series II. Two different 25 m×0.32 mm WCOT fused silica columns were used, depending on the different substrates and products that were analyzed. A polar GC-column with CP Chirasil-Dex CB coating was used for the reactions with 1,2-ethanediol and 1,3-propanediol. A non-polar GC-column with CP-SIL 5CB coating was used for the reactions with 1,4-butanediol, 2-methyl-1,3-propanediol and 2-phenyl-1,3-propanediol.

The response factor for each diol was determined in relationship to 3-hexanone. When all diol and mono-ester had converted to di-ester, the response factor for the di-ester could be determined in relationship to decane. The concentration of mono-ester in each reaction was determined by subtracting the concentration of di-ester from the starting concentration of diol.

Example 3

Enzyme-Catalyzed Acylation Reactions with Different Diols as Substrate and Vinyl Butyrate as Acyl Donor Reactions were run with two different diols:
1,4-butanediol, ≥99% from Aldrich.
2-methyl-1,3-propanediol.

Each diol was dissolved to a concentration of 10 mM together with 2 mM of decane ≥98% from Fluka and 200 mM vinyl butyrate >99% from Fluka in MTBE 99.5% from Lab-Scan, which was used as acyl donor and solvent. Reactions were started by adding 4 ml reaction solution to 20 mg enzyme carrier beads loaded with either wild-type or T40A mutated CALB. Reactions were run at 29° C. on a HLC rotating thermo block. Aliquots of 50 µl were taken, filtered through wool in a Pasteur pipette and diluted with 50 µl ethyl acetate prior to analysis. The decane used as internal standard were present in the reaction solution throughout both reaction and analysis.

All reactions were analyzed on GC, Hewlett Packard 5890 series II. A 25 m×0.32 mm WCOT fused silica non-polar GC-column with CP-SIL 5CB coating was used for the reactions.

The response factor for each diol was determined in relationship to decane. When all diol and mono-ester had converted to di-ester, the response factor for the di-ester could be determined in relationship to decane. The concentration of mono-ester in each reaction was determined by subtracting the concentration of di-ester from the starting concentration of diol.

Example 4

Enzyme-Catalyzed Acylation Reactions with Different Diols as Substrate in Competition with 1-Butanol Reactions were run with two different straight chain primary diols:
1,2-ethanediol, ≥99.5% from MERCK,
1,4-butanediol, ≥99% from Aldrich.
Additionally, 1-butanol, ≥99.5% from Riedel-de Haën, was used as a competing substrate.
25 mM decane ≥98% from Fluka, was used as internal standard.
Two different acyl donors were used:
Ethyl acetate, ≥99% from Fluka, used as both solvent and acyl donor
1 M Vinyl butyrate, >99% from Fluka, together with in MTBE, 99.5% from Lab-Scan, used as solvent.
Each diol was dissolved to a concentration of 100 mM together with 25 mM of decane in ethyl acetate, ≥99% from Fluka, used as acyl donor and solvent. Reactions were started by adding 3 ml reaction solution to 10 mg enzyme carrier beads loaded with wild-type CALB or 20 mg carrier beads loaded with T40A mutated CALB. Reactions were run at 29° C. in a temperature bath consisting of a HETO thermostat coupled to a Bom-roerder combined temperature bath and magnetic stirrer. 25 mM decane was used as internal standard were present in the reaction solution throughout both reaction and analysis. Aliquots of 60 µl were taken, filtered through wool in a Pasteur pipette together with 540 µl ethyl acetate prior to analysis. The filtration through wool removed any remaining enzyme from the reaction solution, and the reaction samples were diluted by a factor of 10 prior to analysis.

All reactions were analyzed on GC, Hewlett Packard 5890 series II. Two different 25 m×0.32 mm WCOT fused silica columns were used, depending on the different substrates and products that were analyzed. A polar GC-column with CP Chirasil-Dex CB coating was used for the reactions with 1,2-ethanediol. A non-polar GC-column with CP-SIL 5CB coating was used for the reactions with 1,4-butanediol.

The response factor for each diol was determined in relationship to decane. When all diol and mono-ester had converted to di-ester, the response factor for the di-ester could be determined in relationship to decane. The concentration of mono-ester in each reaction was determined by subtracting the concentration of di-ester from the starting concentration of diol.

Example 5

Preparation of CALB A282L Mutant and Immobilization

Freeze dried A282L mutated CALB was obtained from in-house productions from earlier experiments [Z. Marton, V. Léonard-Nevers, P.-O, Syrén, C. Bauer, S. Lamare, K. Hult, V. Tranc and M. Graber, *Mutations in the stereospecificity pocket and at the entrance of the active site of Candida antarctica lipase B enhancing enzyme enantioselectivity*. Journal of Molecular Catalysis B: Enzymatic].
A282L was proposed from structure-based enzyme engineering. The primer pair to introduce the mutation was

5'-CCTGGCGCCGGCATTGGCAGCC-3', (SEQ ID NO: 9)

and the corresponding reverse complementary sequence:

5'-GGCTGCCAATGCCGGCGCCAGG-3'. (SEQ ID NO: 10)

After the enzyme carrying this mutation showed enhanced selectivity, the position 282 was subjected to saturation mutagenesis. For saturation mutagenesis the primers 5'-CTGGCGCCGGCGNNNGCAGCCAT-3' (SEQ ID NO: 11)
and
5'-ATGGCTGCNNNCGCCGGCGCCAG-3, (SEQ ID NO: 12)

indicated in a generic form, wherein N represents A, T, C or G, were used. Consequently, NNN represents the random use of any possible codon triplett, because in the PCR a corresponding primer mix was used. 900 transformation positive colonies were picked, cultivated and the respective proteins expressed in microtitre plate scale. Screening the selectivity in the transesterification reaction ethyl acrylate+butane diol showed that position 282 is important for the selectivity in diol transesterification.

All mutations in position 282 were created by saturation mutagenesis as indicated above. 10 microtitre plates including 8 control wells each (expression of wild type (WT), empty *P. pastoris* X33) were picked with positive transformants. Enzyme expression was induced by addition of methanol. The cells and supernatant were freeze-dried. Freeze-dried pellets were used in transesterification assays. GC was used for detection of the reaction products.

For construction the mutant I285F the following pair of primers was used:

forward primer: 5'-GCAGCCTTTGTGGCG-3' (SEQ ID NO: 13)

reverse primer: 5'-CGCCACAAAGGCTGC-3' (SEQ ID NO: 14)

The double mutation A282L/I285F was simulataneously introduced by the following pair of primers:

forward primer:
5'-CCGGCGCTTGCAGCCTTTGTGGCGGGTCCAAAG-3' (SEQ ID NO: 15)

reverse primer:
5'-CTTTGGACCCGCCACAAAGGCTGCAAGCGCCGG-3' (SEQ ID NO: 16)

Using the primers forward: 5'-GCTCTCTGCGCCGGC-3' (SEQ ID NO: 17)

reverse: 5'-GCCGGCGCAGCGACG-3', (SEQ ID NO: 18)

the double mutant L278S/A282L was prepared by first separately introducing the L278S mutant and adding this to the A282L mutant.

Approximately 2 mg of the freeze dried A282L CALB or other mutants as described above were dissolved in 10 ml 100 mM $K_xH_yPO_4$, pH 7.0. The enzyme was immobilized on 1 g of Accurel beads according to the general protocol described under A. Materials and Methods, 1. Enzyme Immobilisation, with the following exceptions: The immobilisation solution was left in end over end in room temperature for 24 hours. After immobilisation, wash with NH4Ac and drying, the enzyme beads were subjected to an additional wash in 50 ml 10 mM MOPS, pH 7.5, for 24 hours in end over end in room temperature. The beads were dried under vacuum overnight and stored over lithium chloride.

The amount of enzyme loaded on the beads was analyzed by active site titration, as described for T40A and wild type CALB. An enzyme load of 0.17% (w/w) was confirmed.

Example 6

Preparation of CALB A281V and A281E Mutants and Immobilization

The A281V and A281E mutated CALB variants were prepared by overlapping extension PCR using pET22b+ vector obtained from earlier studies [Larsen M. W., et al., *Expression of Candida antarctica lipase B in Pichia pastoris and various Escerichia coli systems*, Protein Expression and Purification, 2008, 62(1): p. 90-97]. In the first step forward and reverse PCR reactions were done for the A281V and A281E mutated CALB. For the forward reaction, reverse NotI primer was used together with 5'-CGGCTGCGCTCCTGGCTCCTG-TAGCTG-3' (SEQ ID NO:19) for the A281V variant and 5'-CGGCTGCGCTCCTGGCTCCTGAGGCTG-3' (SEQ ID NO:21) for the A281E variant. For the reverse reaction, forward NocI primer was used together with 5'-CTGCAGCTA-CAGGAGCCAGGAGCGCAG-3' (SEQ ID NO:20) for the A281V variant and 5'-CAGCCTCAGGAGCCAGGAGCG-CAGCCG-3' (SEQ ID NO:22) for the A281E variant. Second PCR reactions were carried out for the A281V and A281E mutated CALB. 1 µl from the forward and 1 µl from the reverse reaction were used together with forward NcoI and reverse Not primers. The PCR temperature program was identical for both steps. 98° C. for 30s, 30 cycles with 10 s at 98° C., 15 s at 65° C. and 20 s at 72° C. and 5 min 72° C. Forward NcoI and reverse Not primers were from Thermo Scientific. The PCR products and pET22b+ were digested using FastDigest restriction enzymes NotI and NcoI, from Fermentas. The PCR products and linearised pET22b+ were purified on a 1% agarose gel and extracted using the QIAquick Gel Extraction Kit from QIAGEN. The PCR products were ligated back into the linearised pET22b+ using T4 DNA ligase from Fermentas. Incubations were done in room temperature for 1 hour and 20 min. Electro competent Rosetta strain *Escherichia coli* cells were transformed with the ligation solution. 1 µl of the solution containing A281V CALB and 0.5 µl of the solution containing A281E CALB were added to the cells. The mutation was confirmed by sequencing by Eurofins MWG Operon (Ebersberg, Germany).

Expression and purification of the protein was done according to a predefined protocol for periplasmic expression of CALB using *Escherichia coli* strain Rosetta [Larsen M. W., et al., *Expression of Candida antarctica lipase B in Pichia pastoris and various Escerichia coli systems*, Protein Expression and Purification, 2008, 62(1): p. 90-97]. The purified enzymes were subjected to buffer exchange using PD-10 columns from GE healthcare. The buffer was changed into 10 mM MOPS, pH7.2, which was used as immobilisation buffer.

For the A281V and A281E mutated CALB, 1.5 g and 2 g Accurel enzyme carrier beads were used, respectively. Prior to the immobilisation, the beads were washed for 2 hours in 95% ethanol and then washed in fresh ethanol. The ethanol was washed off with 3×10 ml immobilisation buffer, 10 mM MOPS, pH 7.2 The immobilisation solution was done in 10 ml 10 mM MOPS, pH 7.2, left in end over end in room temperature overnight.

The amount of enzyme loaded on the beads could not be analyzed by active site titration, the amounts were too low. Immobilisation of the A281V and A281E CALB were confirmed by a comassie stained gel with samples of the solution before and after the immobilisation.

Example 7

Determination of Enzyme Selectivities and Specificities of A282L, A281V and A281E Reactions using the CALB mutants as described in Example 5 and Example 6 were run with two different straight chain primary diols: 1,2-ethanediol, ≥99.5% from MERCK and 1,4-butanediol, ≥99% from Aldrich. Two different acyl donors were used: vinyl acetate, ≥99% from Fluka and vinyl butyrate, >99% from Fluka. Decane, ≥99% from Fluka, was used as internal standard. MTBE, 99.5% from Lab-Scan was used as solvent.

Each diol was dissolved to a concentration of 100 mM together with 1 M of the acyl donor and 20 mM decane in MTBE. Reactions were started by adding 3 ml reaction solution to a specific amount of enzyme carrier beads. Different amounts of enzyme carrier beads were used for the different reactions. For reactions with 1,2-ethanediol and vinyl acetate, 19.7 mg wild type, 22.5 mg A282L, 50.5 mg A281V, and 45.5 A281E CALB were used. For reactions with 1,2-ethanediol and vinyl butyrate, 19.3 mg wild type, 19.7 mg A282L, 40.5 mg A281V, and 40.6 A281E CALB were used. For reactions with 1,4-butanediol and vinyl acetate, 17.6 mg wild type, 22.5 mg A282L, 69 mg A281V, and 54 A281E CALB were used. For reactions with 1,4-butanediol and vinyl butyrate, 20.3 mg wild type, 25.4 mg A282L, 52.2 mg A281V, and 53 A281E CALB were used. The enzymes were evenly distributed in the reaction vials by magnetic stirrers. The vials were kept in a 29° C. water bath during the reactions for temperature control. Aliquots of 10 µl were taken, filtered through wool in a Pasteur pipette and diluted with 90 µl MTBE prior to analysis. The decane used as internal standard was present in the reaction solution throughout both reaction and analysis.

20 mM decane was used as internal standard in the reaction mixtures together with 100 mM diol. Aliquots were taken during the reaction by taking 10 µl of reaction sample. The samples were filtered though wool together with 90 µl MTBE, thereby any remaining enzyme was removed and the reaction samples were diluted by a factor of 10 prior to analysis.

The reactions catalyzed by the A281V-mutant were rerun with higher amounts of enzyme carrier beads to test selectivity determinations. For the reactions with 1,2-ethanediol and vinyl acetate, 121 mg beads with A281V CALB were used. For the reactions with 1,2-ethanediol and vinyl butyrate, 122.9 mg beads with A281V CALB were used. For the reactions with 1,4-butanediol and vinyl butyrate, 127.8 mg beads with A281V CALB were used.

All reactions were analyzed on GC, Hewlett Packard 5890 series II. Two different 25 m×0.32 mm WCOT fused silica columns were used, depending on the different substrates and products that were analyzed. A polar GC-column with CP Chirasil-Dex CB coating was used for the reactions with 1,2-ethanediol. A non-polar GC-column with CP-SIL 5CB coating was used for the reactions with 1,4-butanediol. The response factor for each diol was determined in relationship to decane. When all diol and mono-ester had converted to di-ester, the response factor for the di-ester could be determined in relationship to decane. The concentration of mono-ester in each reaction was determined by subtracting the concentration of di-ester from the starting concentration of diol.

Example 8

Enzymatic Catalysis in Mini-Reactor Scale

The enzymatic conversion of butandiole and ethylacrylate into 4-hydroxybutyl acrylate (4-HBA, butanediole monoacrylate) and butanediole diacrylate (BDDA) was examined in a 750 ml mini plant reactor with stream circulation over the enzyme column and a partial stream over the column (50 ml column) as stabilizer.

3.75 g immobilized CALB (Novozym® 435, herein also referred to as Novo 435 or Novo435; Novozymes NS, Denmark) or A282L (as prepared in Example 5 and immobilized on Diaion HP 20 L according to the procedure described in Materials and Methods, protein load: 3%), 50.0 g 1,4-butanediole (0.555 moles) and 555.7 g ethylacrylate (5.55 moles) were used, resulting in molar ratio of butanediole:ethylacrylate of 1:10. The total weight of the reaction mix was 0.606 kg. 200 ppm hydroquinone monomethylether (MeHQ, 121 mg) and 200 ppm phenothiazine (121 mg) were included as stabilizers. The educts were filled into the reactor. Prior to allowing the passage of the reaction mix over the immobilized enzyme the reaction mix was heated to reflux at 100 mbar (100 hPa). Samples were taken at various time points and analyzed by gas chromatography (gradient of 50° C. to 290° C. temperature increase: 10° C./min, injection temperature: 220° C.).

Example 9

Dependency of Substrate Conversion and Excess of Product From Flow Rate

For determining the impact of various flow rates on substrate conversion and product excess a double shell glass column of 49 ml total volume (volume of heated part: 26 ml, volume of part containing enzyme: 23 ml, filling height of enzyme material: 167 mm), attached to a Desaga pump and a Ministat was used. The column was filled with either CALB Novo 435 as described in Example 8 or 4.4 g CALB A282L (immobilized on Diaion HP 20 L, 3% protein load). The reaction mix comprised 90.0 g (1.0 mole) 1,4-butanediol and 1400 g (14 moles) ethylacrylate. The reactor was operated at flow rates ranging from 10 ml/h to 1000 ml/h, samples were taken after passage of 135-280 ml reaction mix, depending on the flow rate, and analyzed by gas chromatography as described in Example 8.

Example 10

Determination of Enzyme Selectivities and Specificities of A282T, A282C, A282P, A282I, A282D, A282V, A282M, A282R, I285, A282L/I285F and L278S/A282L 300 mg or another specified amount of the respective enzyme (on a HP20 L carrier) in a 50 ml Duran glass bottle were incubated together with 440 µl 1,4-butanediol, 5.4 ml ethylacrylate and 2 g molecular sieve (0.5 nm) at 40° C. in a shaking water bath (200 rpm). Samples were taken at 2, 4, 6, 24 and 48 hours. Prior to gas chromatography 160 µl sample and 240 µl dioxane were mixed and filtered.

C. Results

Results of Example 2: Enzyme-Catalyzed Acylation Reactions with Different Diols As Substrate and Ethyl Acetate as Acyl Donor

TABLE 1

| Maximum monoester yield: | | |
|---|---|---|
| Substance | T40A | WT |
| 1,2-ethanediol | 77% | 43% |
| 1,3-propanediol | 50% | 33% |
| 1,4-butanediol | 49% | 25% |
| 2-Me-1,3-propanediol | 55% | 42% |
| 2-Ph-1,3-propanediol | 55-65% | 52% |

TABLE 2

| Conversion at 3:1 (monoester:diester) | | |
|---|---|---|
| Substance | T40A | WT |
| 1,2-ethanediol | 99% | 17% |
| 1,3-propanediol | 22% | 19% |
| 1,4-butanediol | 64% | <5% |
| 2-Me-1,3-propanediol | 55% | 30% |
| 2-Ph-1,3-propanediol | >95% | 46% |

TABLE 3

| Conversion at 9:1 (monoester:diester) | | |
|---|---|---|
| Substance | T40A | WT |
| 1,2-ethanediol | 78% | <9% |
| 1,3-propanediol | 19% | 10% |
| 1,4-butanediol | 26% | <5% |

Tables 1-3 shows the difference in selectivity towards diol over monoester between wild type and T40A-mutated CALB. The presented were obtained at 20 mM starting concentration of the diols dissolved in ethyl acetate, which was used as both acyl donor and solvent. The reaction conditions were chosen for comparison between the two catalysts. Further optimisation of the reaction conditions could give higher yields. As diol is consumed in the reaction the formed monoester will be more favoured to react and form diester, due to differences in concentrations. Table 1 shows that the maximum yield of monoacetylated diol increased for all tested diols by using the T40A CALB mutant when compared to wild type CALB. Tables 2 and 3 demonstrates which maximum conversions can be acquired at a given purity of the product; 3:1 and 9:1 (monoester:diester). The figures in tables 2 and 3 shows that more diol can be converted before the product purity drops under the given levels when comparing T40A mutated to wild type CALB.

A great difference in concentration between acyl donor and diol was accomplished in the reactions by using ethyl acetate as solvent and acyldonor and a diol concentration of 20 mM. Therefore the reactions was considered to irreversible, following the reaction scheme:

(scheme 1)

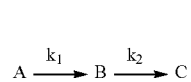

Irreversible reaction conditions validate the following equations:

$$[A] = [A]_0 e^{-k_1 t} \quad \text{(eq. 1)}$$

$$[B] = \frac{[A]_0 k_1}{k_2 - k_1}(e^{-k_1 t} - e^{-k_2 t}) \quad \text{(eq. 2)}$$

$$[C] = [A]_0 \left\{ 1 + \frac{1}{k_1 - k_2}(k_2 e^{-k_1 t} - k_1 e^{-k_2 t}) \right\} \quad \text{(eq. 3)}$$

A, B and C corresponds to diol, monoester and diester, respectively. $k_1$ and $k_2$ respectively corresponds to the reaction rates of the acylation of diol and monoester.

The reaction rates are dependent on enzyme concentrations and the $k_{cat}/K_M$ towards the substrates. By fitting the concentrations measured over time into the equations and using the enzyme concentration determined by active site titration, the following results were obtained.

TABLE 4

Specificity and selectivities towards diols and monoesters for wild type CALB

| Diol | $k_{cat}/K_M$ (s$^{-1}$M$^{-1}$) diol | monoester | Selectivity diol/monoester | $\Delta\Delta G$, diol-monoester (kJ/mol) |
|---|---|---|---|---|
| 1,4-butanediol | 7.7 | 12 | 0.6 | −1.2 |
| 1,3-propanediol | 12 | 13 | 0.9 | −0.17 |
| 1,2-ethanediol | 15 | 8.0 | 1.9 | 1.6 |
| 2-methyl-1,3-propanediol | 5.8 | 3.8 | 1.5 | 1.1 |

TABLE 5

Specificities and selectivities towards diols and monoesters for T40A CALB

| Diol | $K_{cat}/K_M$ (s$^{-1}$M$^{-1}$) diol | monoester | Selectivity diol/monoester | $\Delta\Delta G$, diol-monoester (kJ/mol) |
|---|---|---|---|---|
| 1,4-butanediol | 0.25 | 0.13 | 1.9 | 1.5 |
| 1,3-propanediol | 0.46 | 0.19 | 2.4 | 2.2 |
| 1,2-ethanediol | 0.76 | 0.10 | 7.6 | 5.1 |
| 2-methyl-1,3-propanediol | 0.15 | 0.06 | 2.5 | 2.4 |

TABLE 6

Differences between T40A and wild type CALB in selectivities towards diols over monoesters

| Diol | Selectivity diol/monoester wild type | T40A | Selectivity ratio diol/monoester T40A/WT | $\Delta\Delta\Delta G$, T40A-WT (kJ/mol) |
|---|---|---|---|---|
| 1,4-butanediol | 0.63 | 1.8 | 2.9 | 2.7 |
| 1,3-propanediol | 0.94 | 2.4 | 2.6 | 2.4 |
| 1,2-ethanediol | 1.9 | 7.7 | 4.0 | 3.5 |
| 2-methyl-1,3-propanediol | 1.5 | 2.6 | 1.7 | 1.3 |

Values of $k_{cat}/K_M$ towards diols and monoesters for wild type and T40A CALB are presented in tables 4-6. Table 4 presents $k_{cat}/K_M$ for wild type and table 5 presents $k_{cat}/K_M$ for T40A CALB. Additionally, the selectivities towards diols over monoesters, $(k_{cat}/K_M)_{diol}/(k_{cat}/K_M)_{monoester}$ are presented. The differences in activation energies, $\Delta\Delta G$, are calculated from these selectivities. The selectivities in tables 4 and 5 have been transferred to table 6 for comparison between wild type and T40A mutant. The figures presenting the ratio between the selectivities of T40A/wild type CALB, and the related difference in activation energies, $\Delta\Delta\Delta G$, shows the effect of the T40A mutation in CALB. The tested diols are favoured over their corresponding monoesters as an effect of the T40A mutation.

Figure 1:
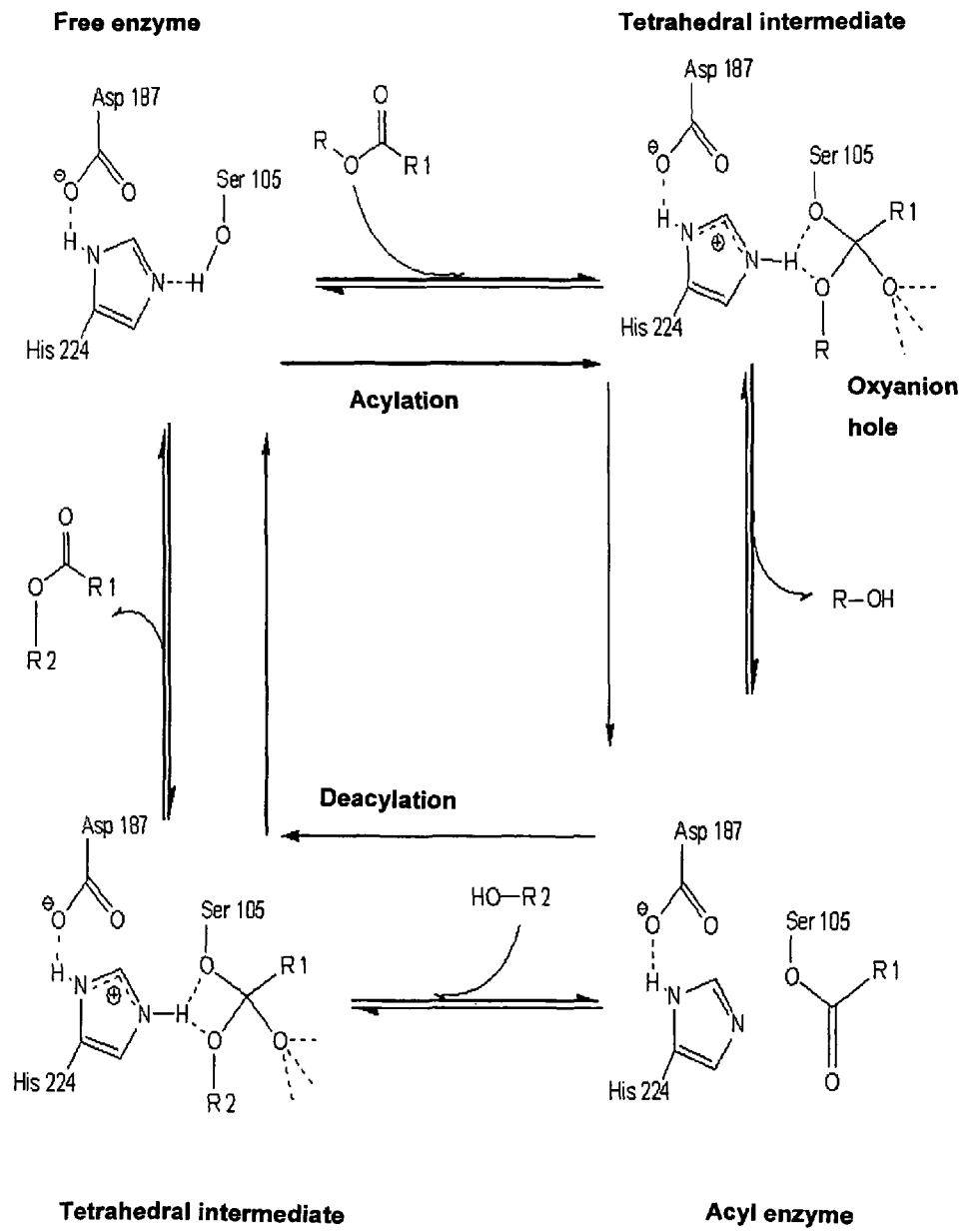
FIG. 1 represents a mechanistic scheme illustrating the interaction of amino acid residues Asp 187, Ser 105 and His 224 of the reactive centre of CALB during a transesterification reaction transferring the acyl residue $C(O)R_1$ of a first ester $ROC(O)R_1$ to an alcohol $HOR_2$ forming a new second ester compound $R_2OC(O)R_1$. The tetrahedral intermediates are stabilized in the oxianion hole of the reactive centre thus favouring the transesterification reaction.
Figure 2A:
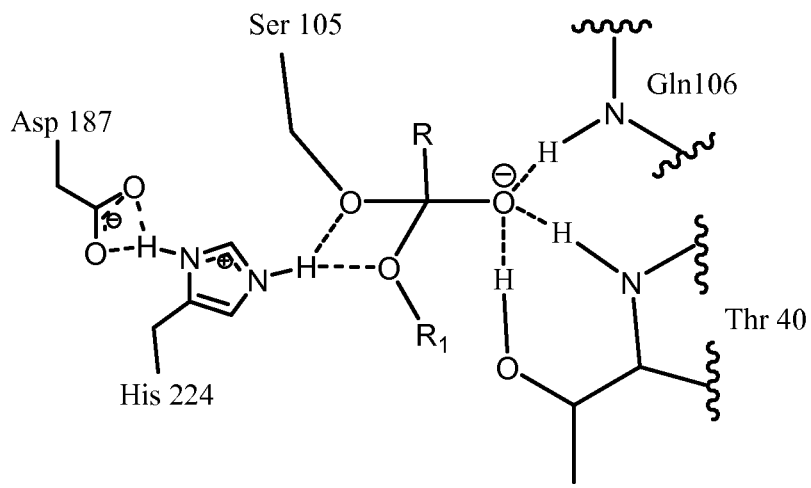
FIG. 2A illustrates the stabilization of the oxianion by formation of 3 hydrogen bonds between the oxianion and amino acid residues Gln 106 and Thr 40. The illustrated ester is of the formula $R_1OC(O)R$.
Figure 2B:
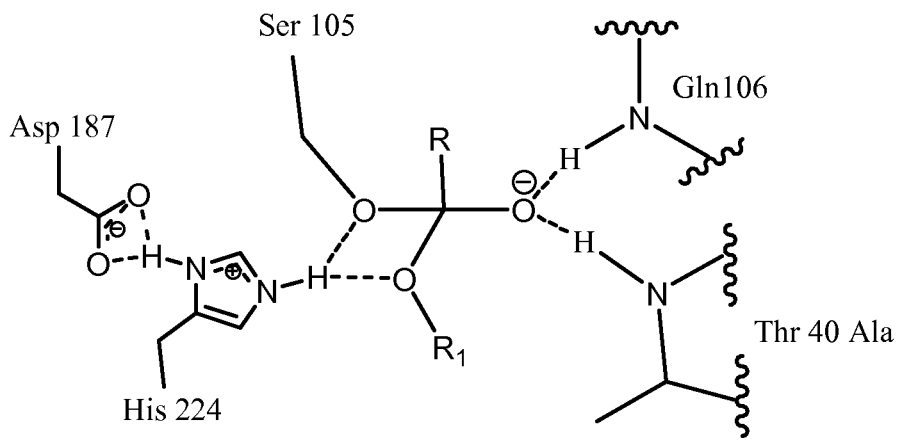
FIG. 2B shows the stabilization of the same substrate as in FIG. 2A but now in the single mutant T40A of CALB, wherein Thr 40 replaced by Ala as a result of which one stabilizing hydrogen bond is getting lost, thus destabilizing said transition state.
Figure 2C:
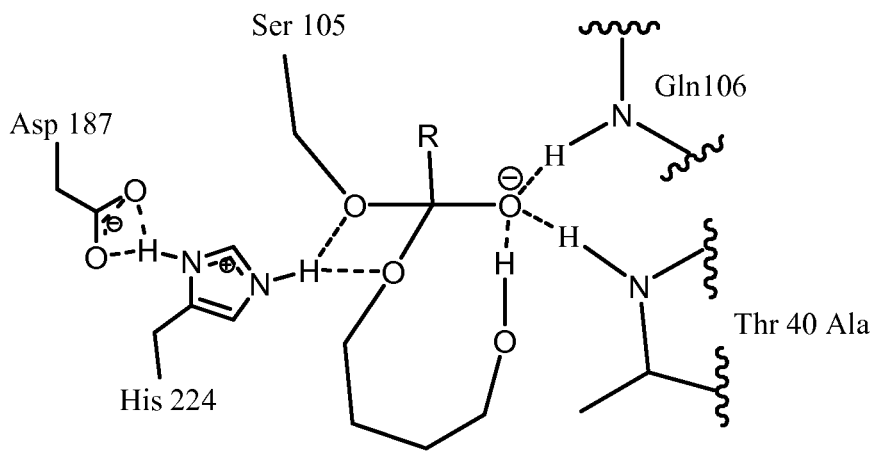
FIG. 2C illustrates the substrate assistance during stabilization of the transition state occurring in the same mutant T40A as observed during the transesterification reaction of a butanediol monoester HOBu-tOC(O)R. The free hydroxy group of the diol interacts with the oxianion via a hydrogen bond so that stability of the transition state is regained. Said substrate assistance by said diol molecule explains the diol preference during the transesterification reactions catalyzed by the T40A mutant.
Figure 3:
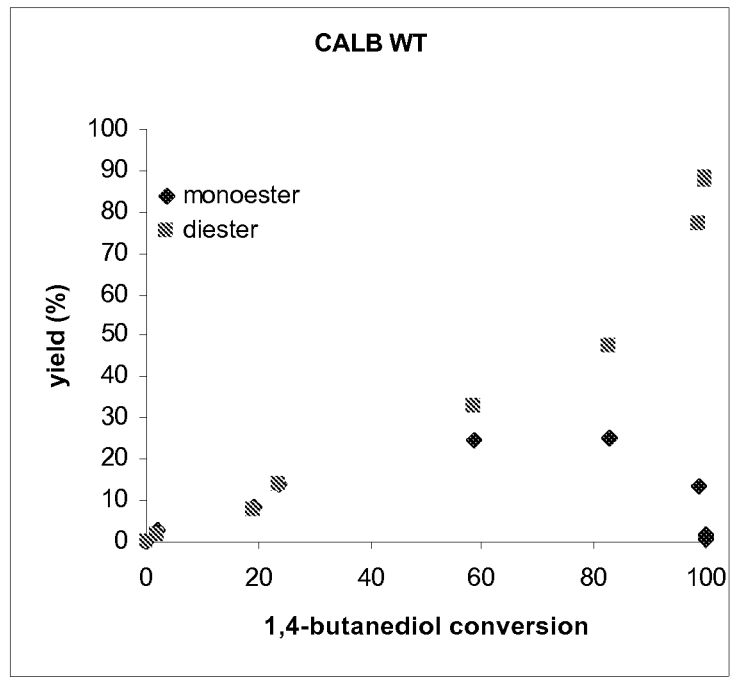
FIG. 3 illustrates the experimental results observed for the transesterification reaction catalyzed by the CALB wild type and the CALB T40A mutant in a transesterification reaction with 1,4-butanediol as substrate dissolved in ethyl acetate. The yield for the mono- and di-acetates is shown as functions of the % conversion. (A) illustrates the results for the CALB wild type. (B) illustrates the results obtained for the CALB mutant T40A. As can be seen, over a wide % conversion range the monoacetate ester is preferably obtained.
Figure 3:
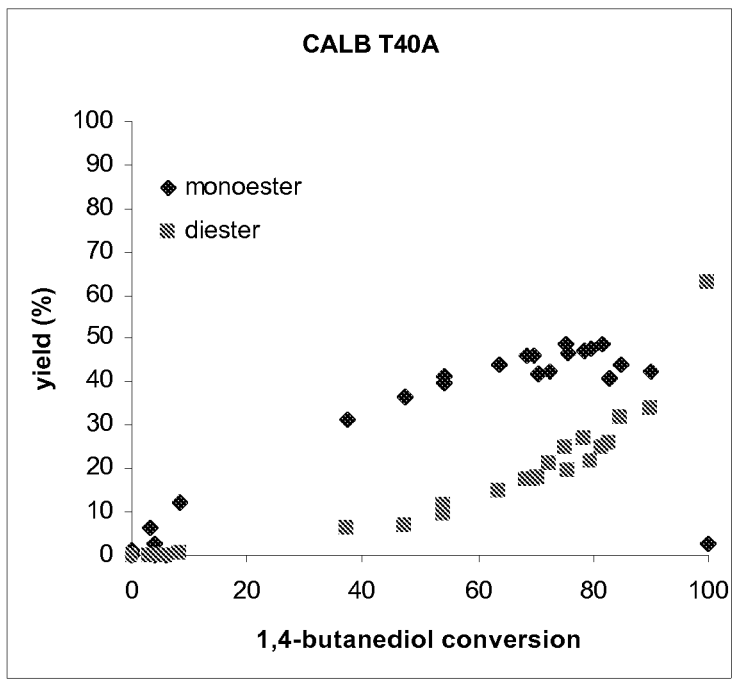
Figure 4:
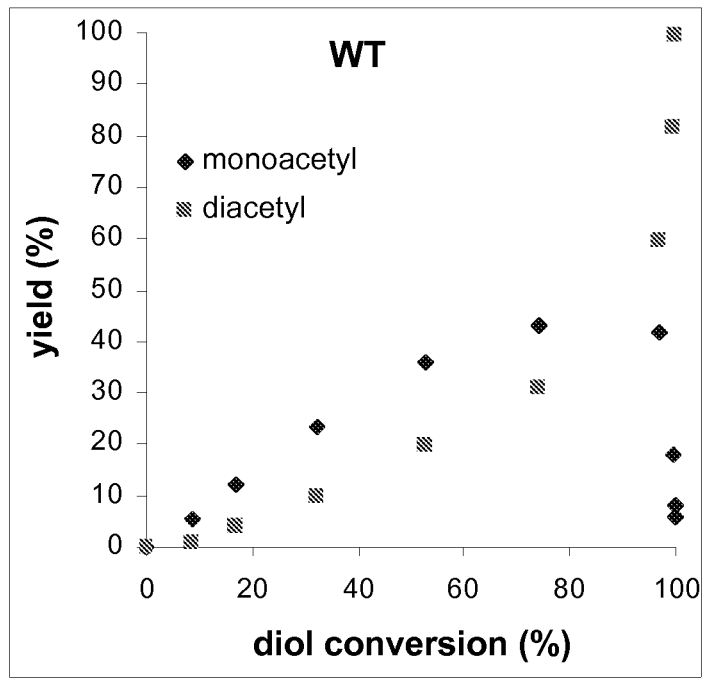
FIG. 4 illustrates the experimental results observed for the transesterification reaction catalyzed by the CALB wild type and the CALB T40A mutant in a transesterification reactions with 1,2-ethanediol as substrate dissolved in ethyl acetate. The yield for the mono- and di-acetate is shown as a function of % conversion. (A) illustrates the results obtained for the CALB wild type. (B) illustrates the results obtained for the CALB mutant T40A. As can be seen, with the T40A mutant the monoacetate ester is preferentially obtained over a wide % conversion range. The maximum monoester yield for the wild type enzyme is 43%; the maximum monoester yield for the mutant is significantly improved to 77% illustrating an improved selectivity of the mutant for the monoester.
Figure 4:
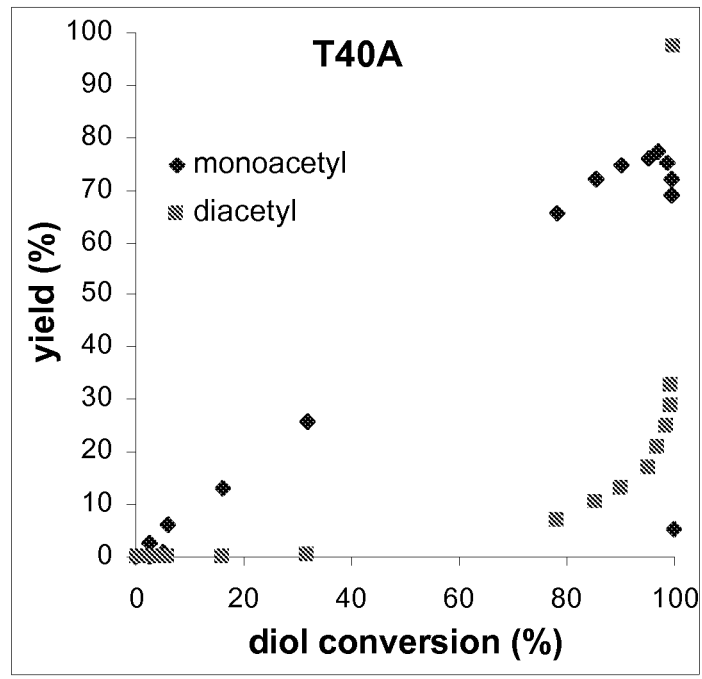

Further results are graphically summarized in FIGS. 3, 4, 5 and 6:

Examples of monoester and diester yield comparing reactions catalyzed with wild type and T40A CALB are illustrated in FIGS. 3 and 4. Reactions with 1,2-ethanediol and 1,4-butanediol are presented in FIGS. 3 and 4 respectively. In both figures the maximum monoester yields are improved by using T40A instead of wild type CALB.

Figure 5:
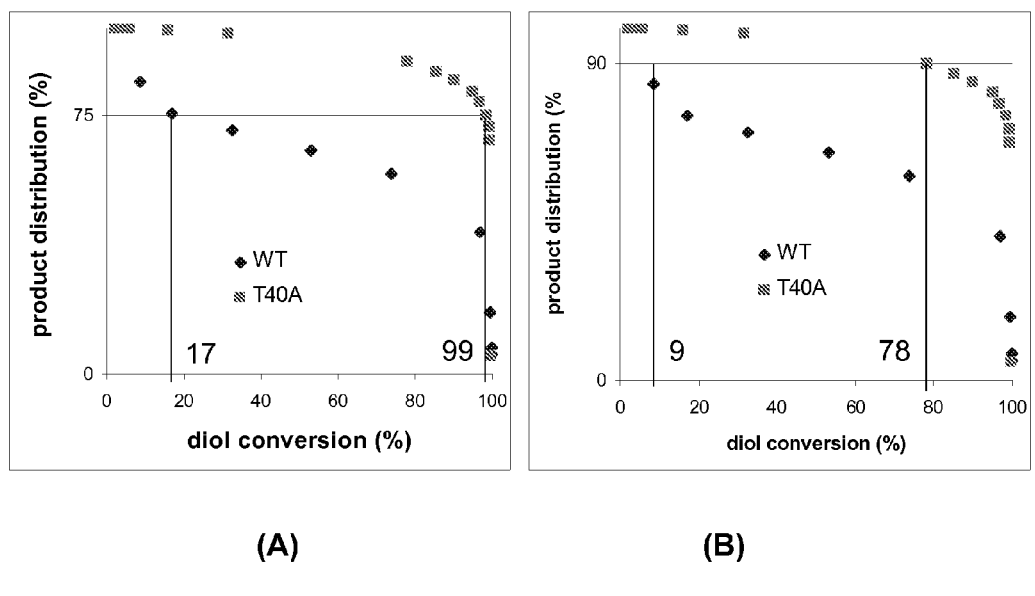
FIG. 5 shows differences between wild type and T40A CALB regarding product distributions in transesterification reactions with 1,2-ethanediol dissolved in ethyl acetate. Illustrated in (A) and (B) are diol conversions at two given product distributions from the same experiments. 17% of the diol was converted with wild type and 99% with T40A CALB for a product distribution of 75% (see (A)). The corresponding figures for a product distribution of 90% are 9% with wild type and 78% with T40A CALB (see (B)).

FIG. 5 shows examples of product distribution for reactions with 1,2-ethanediol catalyzed by wild type and T40A CALB. The product distribution is calculated by the following equation:

$$\text{product distribution} = \frac{[monoester]}{[monoester] + [diester]} \quad \text{(eq. 4)}$$

A product distribution of 75% corresponds to 3:1, monoester:diester, and 90% to 9:1, monoester:diester.

Figure 6:
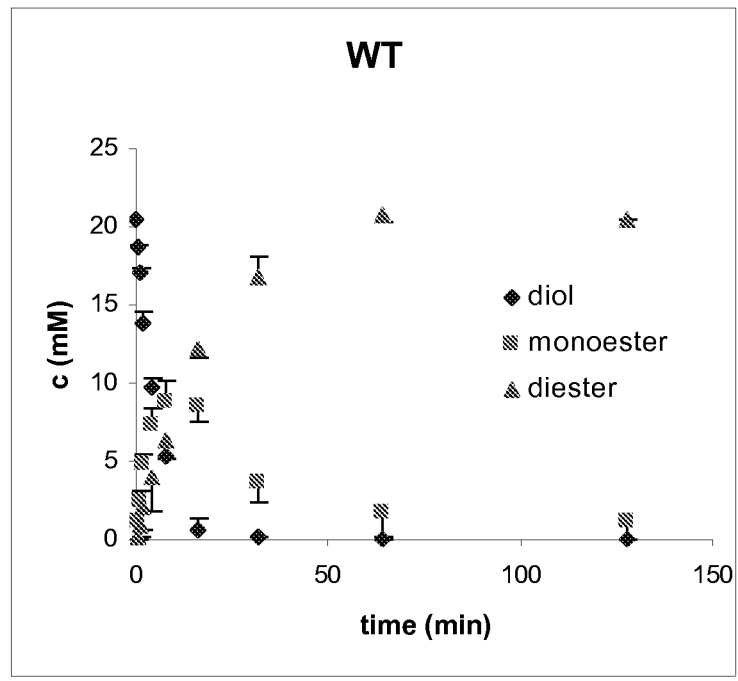
FIG. 6 illustrates the data fitted to a model based on equations 1-3. The dots showing diol (rhombi), monoester (squares) and diester (triangles) are measured values. The error bars show values calculated using the obtained $k_{cat}/K_M$-values in equations 1-3. (A) and (B) corresponds to wild type and T40A CALB respectively.
Figure 6:
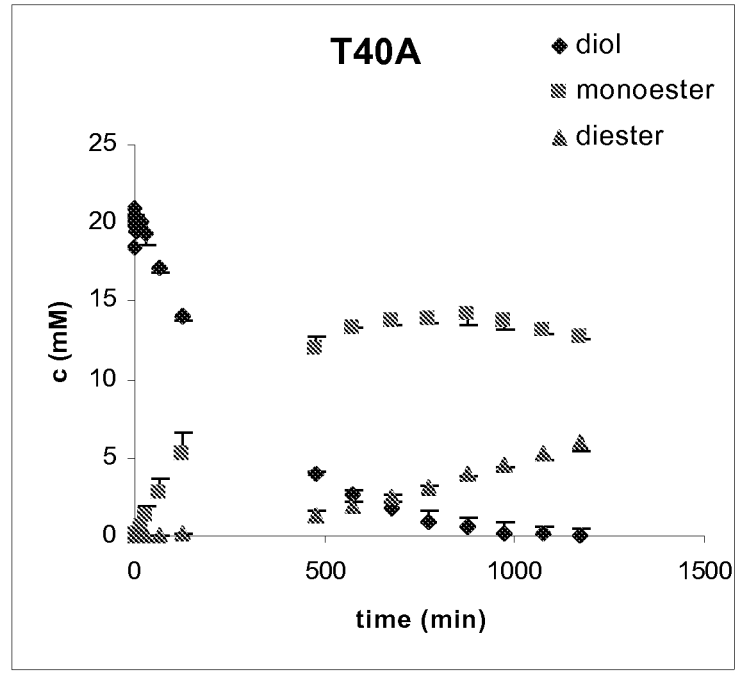

FIG. 6 gives a view of how concentrations of diols, mono- and diesters change over time for the reaction of 1,2-ethanediol and ethyl acetate catalyzed by wild type or T40A CALB. The error bars represent models from equations 1-3, fitted to the measured values. The models give values for $K_{cat}/K_M$ presented in tables 4-6.

Results of Example 3: Enzyme-Catalyzed Acylation Reactions with Different Diols As Substrate and Vinyl Butyrate as Acyl Donor

TABLE 7

Maximum monoester yields:

| Diol | T40A | WT |
|---|---|---|
| 1,4-butanediol | 44 | 25 |
| 2-methyl-1,3-propanediol | 56 | 34 |

Table 7 shows differences in measured maximum yields between wild type and T40A CALB. The selectivity towards the diols over their corresponding monobutyrate esters is higher for T40A than wild type CALB. These results agree with results presented in table 1.

Figure 7:
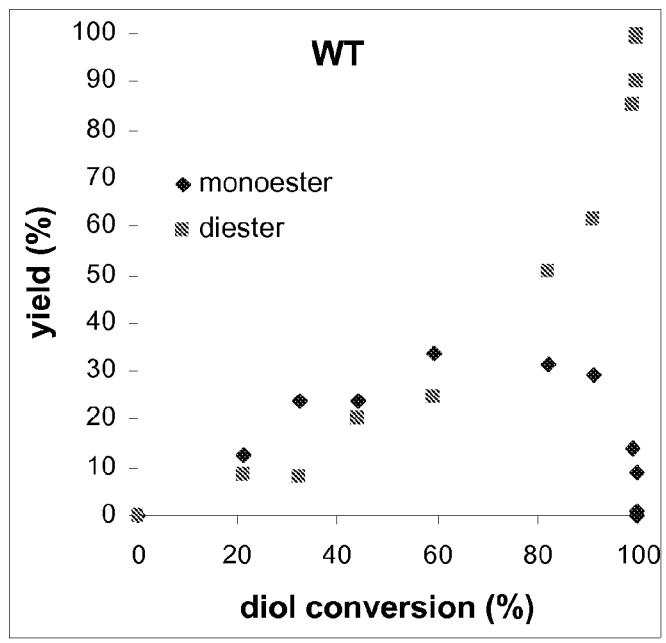
FIG. 7 illustrates the yields of monoester and diester in transacylation reactions with 2-methyl-1,3-propanediol as substrate and vinyl butyrate as acyl donor dissolved in MTBE. Wild type (A) and T40A (B) CALB are used as catalysts. As can be seen, over a wide % conversion range the monobutyrate ester is preferably obtained.
Figure 7:
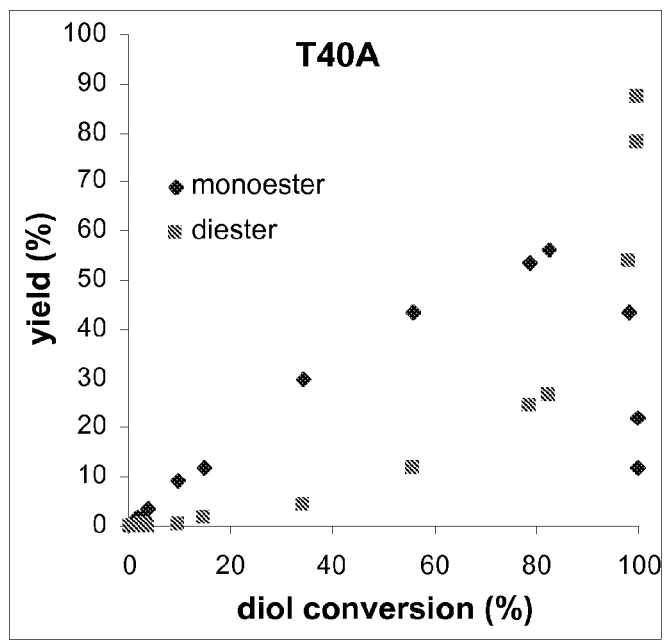
Figure 8:
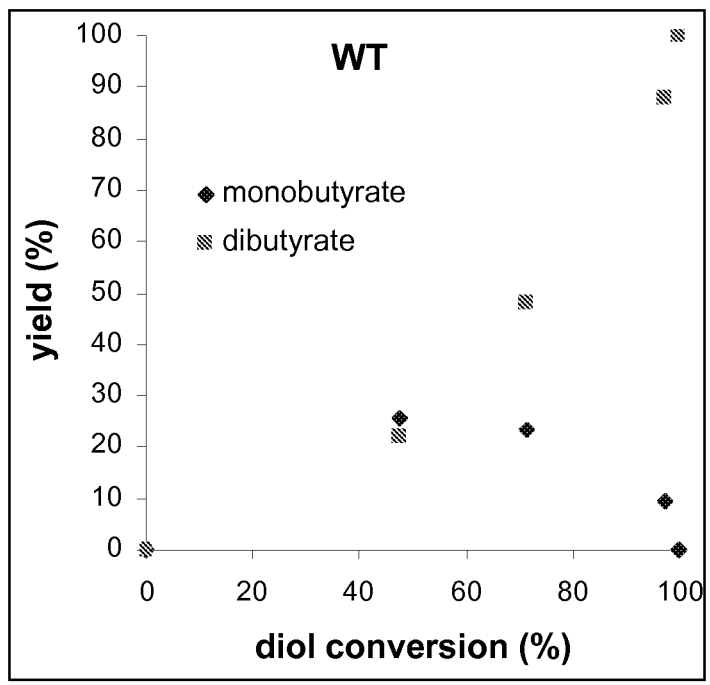
FIG. 8 shows yields of mono-end diester expressed as function of 1,4-butanediol conversion in reactions with vinyl butyrate as an acyl donor dissolved in MTBE. Wild type (A) and T40A (B) CALB are used as catalysts. As can be seen, over a wide % conversion range the monobutyrate ester is preferably obtained.
Figure 8:
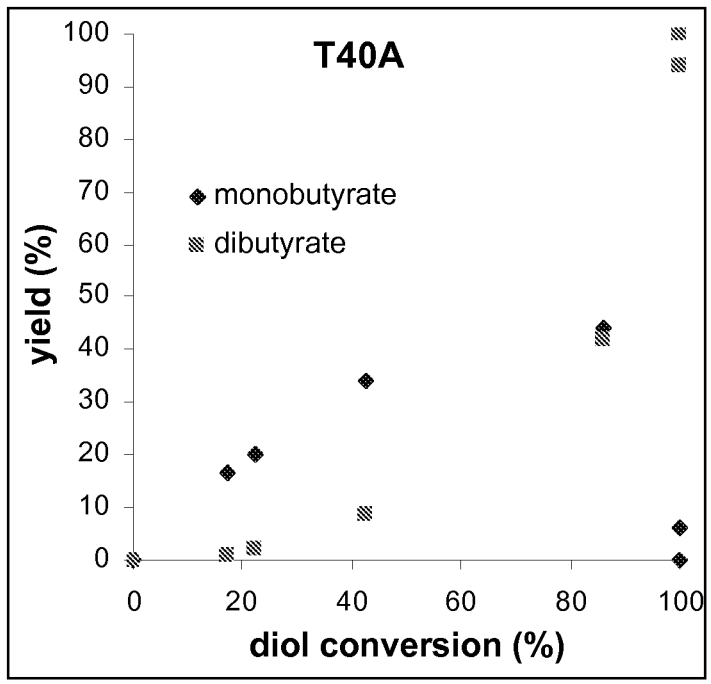

The results are summarized in FIGS. 7 and 8

FIGS. 7 and 8 shows yields of mono- and diesters from 2-methyl-1,3-propanediol and 1,4-butanediol in reactions with vinyl butyrate. MTBE was used as solvent. The difference in selectivity between wild type (7A, 8A) and T40A (7B, 8B) towards diol over its corresponding monoester is illustrated in the figures.

Results of Example 4: Competition Experiments Comparing Electivity of Wild Type, T40A and T40V CALB.

100 mM diol 100 mM 1-butanol 25 mM decane as internal standard

Ethyl acetate used as solvent and acyldonor. Alternatively 1 M vinyl butyrate and MTBE.

Figure 9:
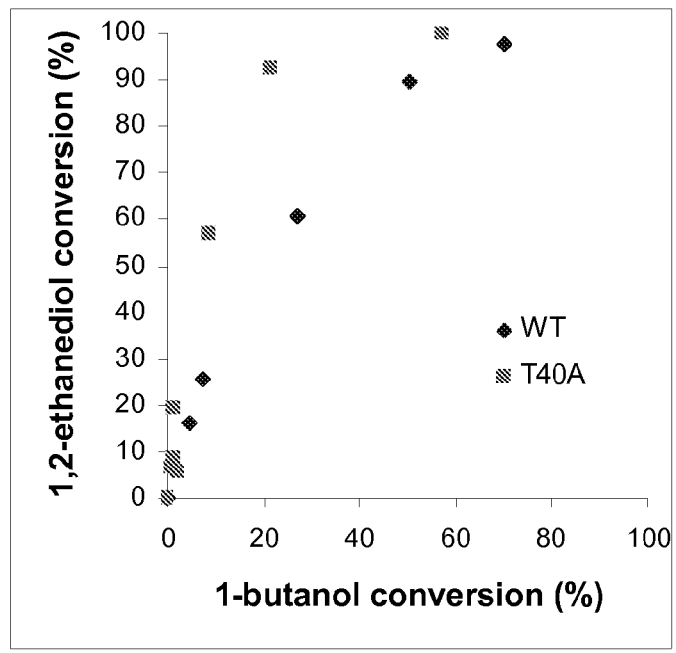
FIG. 9 shows conversions of competing substrates. Conversions of diols are expressed as functions of 1-butanol conversion. Two different diols are displayed, 1,2-ethanediol (A) and 1,4-butanediol (B). The reactions are carried out using ethyl acetate as acyl donor and solvent. Reactions catalyzed by wild type (rhombi) and T40A (squares) CALB are compared. In both A and B the selectivity towards diol over 1-butanol is higher for the reactions catalyzed by T40A than wild type CALB.
Figure 9:
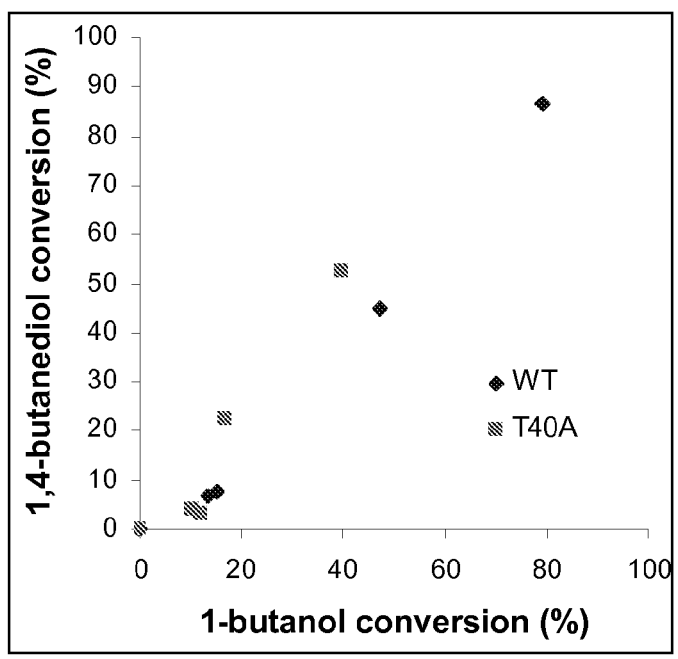
Figure 10:
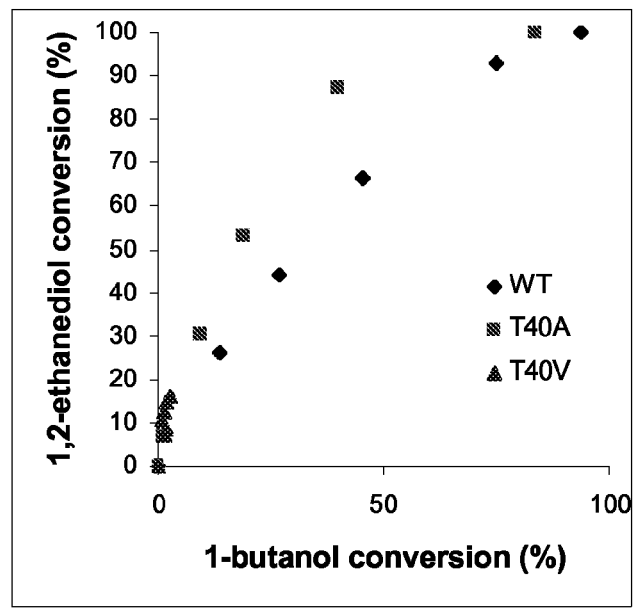
FIG. 10 shows conversions of competing substrates. Conversions of diols are expressed as functions of 1-butanol conversion. Two different diols are displayed, 1,2-ethanediol (A) and 1,4-butanediol (B). The reactions are carried out using vinyl butyrate as acyl donor and MTBE as solvent. Reactions catalyzed by wild type (rhombi), T40A (squares) and T40V (triangles) CALB are compared. In both A and B the selectivity towards diol over 1-butanol is higher for the reactions catalyzed by T40A and T40V than wild type CALB.
Figure 10:
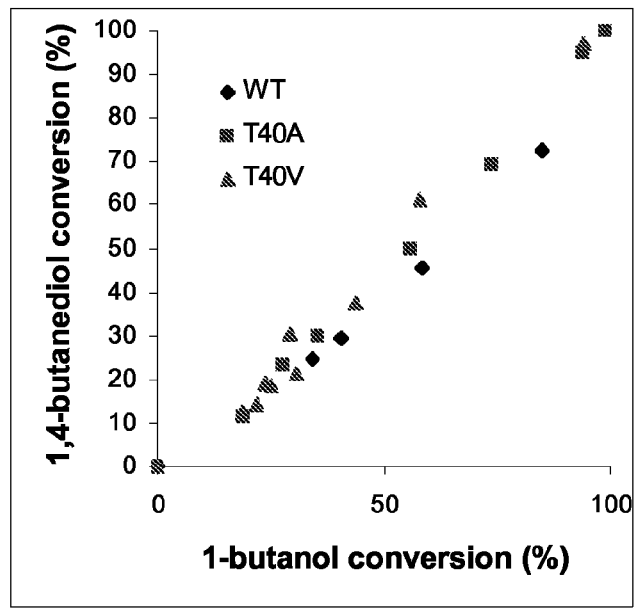

The results are summarized in FIGS. 9 and 10:

In FIGS. 9 and 10 the conversion of diols are expressed as functions of 1-butanol conversion. Ethyl acetate was used as acyl donor and solvent for the experiments presented in FIG. 9. Vinyl butyrate was used as acyl donor and MTBE as solvent for the experiments presented in FIG. 10. Comparisons between wild type and T40A CALB are done in the graphs in FIGS. 9 and 10. Additionally, the graphs in FIG. 10 show reactions catalyzed by T40V CALB. A significant difference between wild type and T40A CALB can be observed in all presented graphs. Diols are converted quicker than 1-butanol when using T40A instead of wild type CALB. Thereby a higher selectivity towards diol over 1-butanol is accomplished with T40A than with wild type CALB.

The higher selectivity towards diol over 1-butanol is observed when 1,2-ethanediol is used as a substrate than for 1,4-butanediol. These observations agree with results presented in table 6, where selectivities towards diols over monoesters are compared between wild type and T40A CALB. The highest selectivity was observed towards 1,2-ethanediol both in FIGS. 9 and 10 and in table 6.

Similar results were obtained when comparing T40V and wild type CALB. Low enzyme expression levels combined with low activity towards the tested substrates gives low reaction rates. Hence, only the reactions containing vinyl butyrate could be accurately measured for the T40V variant. For these reactions, the reaction with 1,4-butanediol were run for a longer period of time than the reaction containing 1,2-ethanediol. Therefore, higher conversions were measured in the reaction containing 1,4-butanediol. Here, it can be seen that the selectivity towards 1,4-butanediol over 1-butanol is higher for T40V than for wild type CALB. The results from the reaction with 1,2-ethanediol suggest that the selectivity is higher also in this case.

Figure 11:
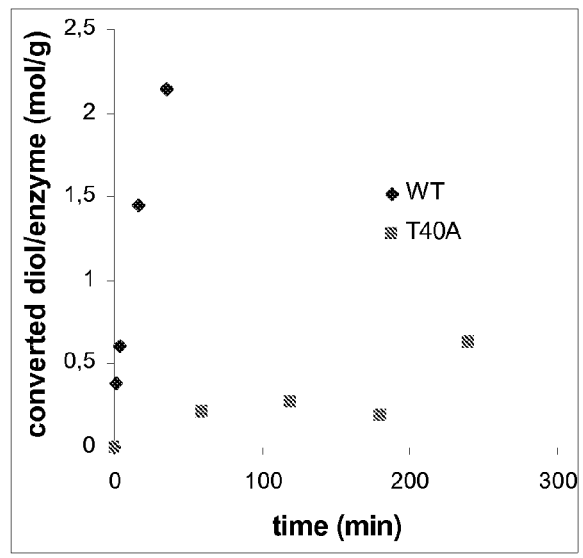
FIG. 11 shows converted 1,2-ethanediol per gram enzyme over time. Ethyl acetate is used as acyl donor and solvent in A.
Figure 11:
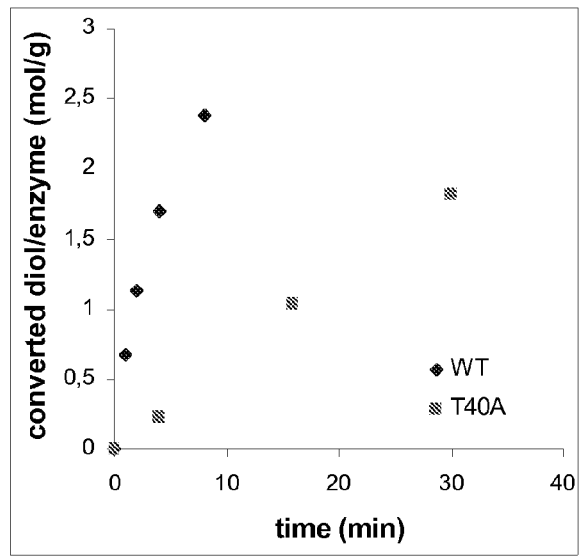

FIG. 11 shows differences in reaction rates for reactions with 1,2-ethanediol catalyzed with wild type and T40A CALB. The amounts of converted moles 1,2-ethanediol per gram enzyme are expressed as functions of time. In 11A ethyl acetate was used as acyl donor and solvent. Vinyl butyrate was used as acyl donor and MTBE as solvent in 11B.

TABLE 8

| | Initial reaction rates | | |
|---|---|---|---|
| | Initial reaction rates (mol/(g min)) | | Rate ratio, |
| Substrates | Wild type | T40A | T40A/WT (%) |
| 1,2-ethanediol ethyl acetate | 0.081 | 0.002 | 2.5 |
| 1,2-ethanediol vinyl butyrate | 0.41 | 0.065 | 16 |
| 1,4-butanediol ethyl acetate | 0.065 | 0.0008 | 1.2 |

TABLE 8-continued

| | Initial reaction rates | | |
|---|---|---|---|
| | Initial reaction rates (mol/(g min)) | | Rate ratio, |
| Substrates | Wild type | T40A | T40A/WT (%) |
| 1,4-butanediol vinyl butyrate | 0.16 | 0.016 | 9.6 |

In table 8 the initial reaction rates are presented for reactions catalyzed by wild type and T40A CALB. Two different diols, 1,2-ethanediol and 1,4-butanediol were used in transacylation reactions with two different acyl donors, ethyl acetate and vinyl butyrate. The rate ratios presented in the third column are a measure of remaining activity in T40A compared to wild type CALB. The rate ratio for T40A over wild type CALB is higher towards vinyl butyrate than towards ethyl acetate. A shift if the rate determining step from acylation to deacylation when shifting from ethyl acetate to vinyl butyrate can explain these differences. There is no substrate assistance in the acylation step which would slow down the acylation from ethyl acetate more than from vinyl butyrate, since the vinyl butyrate is a more activated ester.

The differences in rate ratios for T40A over wild type CALB towards vinyl butyrate and ethyl acetate together with the selectivity towards diol over 1-butanol gives support to the hypothesis of substrate assisted catalysis for diols in T40A.

Results of Example 7: Comparison of Selectivity of Wild Type, A282L, A281V and A281E CALB A different approach to increase monoester yield in transacylation reactions catalyzed by CALB was tested. Mutations A282L, A281V and A281E were made to prevent monoacylated diol to react. The mutations are thought to sterically hinder larger substrates selectively, but not smaller substrates. Thus, diols are better substrates than their corresponding monoester. The results are presented in tables 9 and 10. The reactions were run with a 10 times excess of the acyl donor over diol, and considered irreversible. The reaction scheme 1 and equations 1-3, discussed under Results of example 2, are valid. MTBE was used as solvent.

Table 9 shows selectivities for wild type, A282L, A281V and A281E towards diol over monoester. The selectivities are calculated directly from the rate constants obtained by fitting experimental data to equations 1-3. As the enzyme concentration is identical for both acylation steps, the $k_1/k_2$ is equal to $(k_{cat}/K_M)_{diol}/(k_{cat}/K_M)_{monoester}$. Furthermore, the selectivities have been recalculated into energy differences, $\Delta\Delta G$. The $\Delta\Delta G$ corresponds to the difference in energy in transition state. The tested diols are 1,2-ethanediol and 1,4-butanediol, reacting with either vinyl acetate or vinyl butyrate. Both diols and acyl donors influence the selectivity towards diol over monoester. All three mutants have higher selectivity than the wild type towards all tested substrates. The biggest difference between CALB variants is for A282L and wild type CALB towards 1,2-ethanetiol and vinyl butyrate.

TABLE 9

Selectivities and the correlating differences in activation energies.

| | 1,2-ethanediol | | | | 1,4-butanediol | | | |
|---|---|---|---|---|---|---|---|---|
| | vinyl acetate | | vinyl butyrate | | vinyl acetate | | vinyl butyrate | |
| PalB Variant | $k_1/k_2$* | $\Delta\Delta G$** (kJ/mol) | $k_1/k_2$* | $\Delta\Delta G$** (kJ/mol) | $k_1/k_2$* | $\Delta\Delta G$** (kJ/mol) | $k_1/k_2$* | $\Delta\Delta G$** (kJ/mol) |
| WT | 1.2 | 0.6 | 0.5 | −1.7 | 0.5 | −1.9 | 0.5 | −1.7 |
| A282L | 2.6 | 2.4 | 5.8 | 4.4 | 1.6 | 1.2 | 3.0 | 2.8 |

TABLE 9-continued

Selectivities and the correlating differences in activation energies.

| | 1,2-ethanediol | | | | 1,4-butanediol | | | |
| --- | --- | --- | --- | --- | --- | --- | --- | --- |
| | vinyl acetate | | vinyl butyrate | | vinyl acetate | | vinyl butyrate | |
| PalB Variant | $k_1/k_2$* | $\Delta\Delta G$** (kJ/mol) | $k_1/k_2$* | $\Delta\Delta G$** (kJ/mol) | $k_1/k_2$* | $\Delta\Delta G$** (kJ/mol) | $k_1/k_2$* | $\Delta\Delta G$** (kJ/mol) |
| A281V | 5.2 | 4.1 | 5.0 | 4.0 | 1.7 | 1.4 | 2.0 | 1.7 |
| A281E | 5.1 | 4.1 | 5.0 | 4.0 | 1.8 | 1.4 | 2.2 | 2.0 |

*$k_1/k_2$ are the constants in equations 1-3 and corresponds to $(k_{cat}/K_M)_{diol}/(k_{cat}/K_M)_{monoester}$.
**Values for $\Delta\Delta G$ are calculated from the presented $k_1/k_2$, and correspond to the difference in transition state energy between the substrates.

Table 10, contains more detailed information about some of the reactions presented in table 9. Specificity constants for wild type and A282L CALB towards 1,2-ethanediol and 1,4-butanediol and their corresponding monoesters, formed using vinyl acetate and vinyl butyrate as acyl donor, are shown. In the tested cases, the specificities are increased towards the diols by the A282L mutation. The specificity towards 1,2-ethanediol in reaction with vinylbutyrate increased from 1.6 to 8.1 s$^{-1}$ mM$^{-1}$. In most cases the specificity towards the monoester decreased as a result of the A282L mutation. The exception is towards monoacetylated 1,2-ethanediol, which may be too small for the sterical hindrance caused by the A282L mutation. As presented in table 9, the selectivity towards diols over their corresponding monoesters increased as a result of the A282L mutation. Changes in specificities towards both diols and monoesters presented in table 10 contributes to the increased selectivity.

TABLE 10

Individual specificities for wild type and A282L CALB towards various diols and monoesters, formed with various acyl donors.

| | Specificities, $k_{cat}/K_M$ (s−1 mM−1) | | | | | | | |
| --- | --- | --- | --- | --- | --- | --- | --- | --- |
| | 1,2-ethanediol | | | | 1,4-butanediol | | | |
| CALB | vinyl acetate | | vinyl butyrate | | vinyl acetate | | vinyl butyrate | |
| variant | diol | ester* | diol | ester* | diol | ester* | diol | ester* |
| WT | 1.6 | 1.2 | 1.6 | 3.2 | 0.9 | 1.9 | 1.4 | 2.8 |
| A282L | 3.2 | 1.2 | 8.1 | 1.4 | 1.6 | 1.0 | 1.7 | 0.6 |

*The ester is the corresponding diol monoacylated by the corresponding acyldonor.

Table 11 shows initial reaction rates for reactions catalyzed wild type and A282L CALB. The tested diols are 1,2-ethanediol and 1,4-butanediol. The acyl donors used for transacylation reactions were vinyl acetate and vinyl butyrate. Comparison of initial reaction rates of A282L over wild type CALB is presented in the last column as percentages. No significant decrease in initial reaction rates can be observed as a result of the A282L mutation. In fact, a significant increase can be seen in 3 out of 4 cases. A possible explanation for the increased initial reaction rates is that the selectivity towards diol over monoester is higher for A282L CALB than for the wild type, as discussed above in tables 9 and 10. As soon as monoester is formed it competes with the diol as substrate for the enzyme. Consequently, the diol conversion rate is reduced. Another possibility for the increased initial reaction rates is that the V$_{max}$, and thus k$_{cat}$, is higher towards the substrates for A282L CALB than for the wild type. An increased k$_{cat}$ means that the A282L-mutant is a better catalyst for the monoacylation of the diols than wild type CALB.

TABLE 11

Initial reaction rates

| | Initial reaction rates (mol/(g min) | | Rate ratio |
| --- | --- | --- | --- |
| Substrates | wild type | A282L | A282L/WT (%) |
| 1,2-ethanediol vinyl acetate | 0.21 | 0.35 | 173 |
| 1,2-ethanediol vinyl butyrate | 0.36 | 1.0 | 287 |
| 1,4-butanediol vinyl acetate | 0.12 | 0.21 | 178 |
| 1,4-butanediol vinyl butyrate | 0.24 | 0.22 | 92 |

Results of Example 8: Excess of Monoacrylate Using A282L Under Mini Reactor Conditions During the experiment the temperature of the reactor shell and the bottom of the reactor were kept at 55° C. and 41° C., respectively. The column temperature was fairly constant at 39° C. during the main part of the reactor runs. From the experimentally determined amounts of butanediol, 4-hydroxybutanediol and butanediol diacrylate the degree of conversion and the excess of 4-hydroxybutanediol over butanediole diacrylate were calculated. As shown in FIG. 12, a higher excess of 4-hydroxybutanediol over butanediole diacrylate within a wide range of substrate conversions after enzymatic catalysis by the A282L mutant or L278S is achieved. The excess obtained after enzymatic catalysis by Novo 435 is measurably lower.

Results of Example 9: Dependency of Substrate Conversion and Excess of Product from Flow Rate After initiation of the reactor run, samples were taken as indicated in Table 12:

TABLE 12

| Flow rate [ml/h] | Time of Sampling [hh:mm] | Volume passed over column at sampling [ml] |
| --- | --- | --- |
| 1000 | 00:00 | 0 |
| 1000 | 00.17 | 280 |
| 400 | 00:00 | 0 |
| 400 | 00:35 | 230 |
| 200 | 00:00 | 0 |
| 200 | 01:23 | 277 |
| 100 | 00:00 | 0 |
| 100 | 02:00 | 200 |
| 50 | 00:00 | 0 |
| 50 | 02:43 | 135 |
| 10 | 00:00 | 0 |
| 10 | 15:48 | 155 |

Table 13 shows the contents of 1,4-butanediol, 4-hydroxybutanediol and butanediol diacrylate of the samples taken at the respective end time points of table 12 after passage over a CALB A282L loaded column.

TABLE 13

| Flow rate [ml/h] | Percentage BD | Percentage 4-HBA | Percentage BDDA | Conversion [%] | Excess of 4HBA | Ratio 4HBA:BDDA |
|---|---|---|---|---|---|---|
| 1000 | 89.6 | 9.4 | 1.0 | 10.4 | 80.8 | 9.4 |
| 400 | 68.8 | 27.9 | 3.3 | 31.12 | 78.8 | 8.5 |
| 200 | 51.7 | 41.1 | 7.2 | 48.3 | 70.2 | 5.7 |
| 100 | 35.0 | 50.6 | 14.3 | 65.0 | 55.9 | 3.5 |
| 50 | 19.7 | 53.7 | 26.6 | 80.3 | 33.7 | 2.0 |
| 10 | 3.1 | 32.2 | 64.7 | 96.9 | −33.5 | 0.0 |

The dependency of product excess from conversion rates from flow rates are shown in FIG. 13. The excess of the desired product was comparable after conversion by CALB Novo 435 and CALB A282L at flow rates of 400 ml/h and higher. Due to a considerably higher conversion of substrate by CALB A282L at all flow rates, the mutant according to the invention is superior to CALB Novo 435 in these ranges.

When comparing Novo 435 and A282L at approximately the same conversion, the excess of monacrylate produced by A282L is higher.

Results of Example 10: Determination of Enzyme Selectivities and Specificities of A282T, A282C, A282P, A282I, A282Asp, A282V, A282M, A282R, I285, A282L/I285F and L278S/A282L The results of FIG. 14A and FIG. 14B are based on reactions containing 300 mg enzyme immobilized on HP20 L Diaion, those of FIGS. 15A and 15B on 134 mg enzyme (A282I), 117 mg enzyme (A282R), 140 mg enzyme (A282C), 300 mg enzyme (A282L/I285F) and 115 mg enzyme (I285F). From the results shown in FIG. 14A, FIG. 14B, and FIG. 15A, FIG. 15B it is clear that the mutations A282C, A282P, A282I, A282Asp, A282L, A282V, A282R, I285F as well as the double mutant L282S/A282L cause a measurable increase monoacrylate excess when compared to CALB Novo 435. The double mutant A282L/I285F leads to a slight deterioration of monoacrylate excess versus degree of conversion.

The references as cited herein and the attached sequence listing are explicitly referred to.

---

SEQUENCE LISTING

<160> NUMBER OF SEQ ID NOS: 22

<210> SEQ ID NO 1
<211> LENGTH: 954
<212> TYPE: DNA
<213> ORGANISM: Candida antarctica
<220> FEATURE:
<221> NAME/KEY: CDS
<222> LOCATION: (1)..(954)

<400> SEQUENCE: 1

```
cta cct tcc ggt tcg gac cct gcc ttt tcg cag ccc aag tcg gtg ctc       48
Leu Pro Ser Gly Ser Asp Pro Ala Phe Ser Gln Pro Lys Ser Val Leu
1               5                  10                  15 gat gcg ggt ctg acc tgc cag ggt gct tcg cca tcg tcg gtc tcc aaa       96
Asp Ala Gly Leu Thr Cys Gln Gly Ala Ser Pro Ser Ser Val Ser Lys
                20                  25                  30 ccc atc ctt ctc gtc ccc gga acc ggc acc aca ggt cca cag tcg ttc      144
Pro Ile Leu Leu Val Pro Gly Thr Gly Thr Thr Gly Pro Gln Ser Phe
            35                  40                  45 gac tcg aac tgg atc ccc ctc tct gcg cag ctg ggt tac aca ccc tgc      192
Asp Ser Asn Trp Ile Pro Leu Ser Ala Gln Leu Gly Tyr Thr Pro Cys
        50                  55                  60 tgg atc tca ccc ccg ccg ttc atg ctc aac gac acc cag gtc aac acg      240
Trp Ile Ser Pro Pro Pro Phe Met Leu Asn Asp Thr Gln Val Asn Thr
65                  70                  75                  80 gag tac atg gtc aac gcc atc acc acg ctc tac gct ggt tcg ggc aac      288
Glu Tyr Met Val Asn Ala Ile Thr Thr Leu Tyr Ala Gly Ser Gly Asn
                85                  90                  95 aac aag ctt ccc gtg ctc acc tgg tcc cag ggt ggt ctg gtt gca cag      336
Asn Lys Leu Pro Val Leu Thr Trp Ser Gln Gly Gly Leu Val Ala Gln
                100                 105                 110 tgg ggt ctg acc ttc ttc ccc agt atc agg tcc aag gtc gat cga ctt      384
Trp Gly Leu Thr Phe Phe Pro Ser Ile Arg Ser Lys Val Asp Arg Leu
            115                 120                 125 atg gcc ttt gcg ccc gac tac aag ggc acc gtc ctc gcc ggc cct ctc      432
Met Ala Phe Ala Pro Asp Tyr Lys Gly Thr Val Leu Ala Gly Pro Leu
        130                 135                 140 gat gca ctc gcg gtt agt gca ccc tcc gta tgg cag caa acc acc ggt      480
```

```
                                                             -continued

Asp Ala Leu Ala Val Ser Ala Pro Ser Val Trp Gln Gln Thr Thr Gly
145                 150                 155                 160 tcg gca ctc act acc gca ctc cga aac gca ggt ggt ctg acc cag atc    528
Ser Ala Leu Thr Thr Ala Leu Arg Asn Ala Gly Gly Leu Thr Gln Ile
                165                 170                 175 gtg ccc acc acc aac ctc tac tcg gcg acc gac gag atc gtt cag cct    576
Val Pro Thr Thr Asn Leu Tyr Ser Ala Thr Asp Glu Ile Val Gln Pro
            180                 185                 190 cag gtg tcc aac tcg cca ctc gac tca tcc tac ctc ttc aac gga aag    624
Gln Val Ser Asn Ser Pro Leu Asp Ser Ser Tyr Leu Phe Asn Gly Lys
        195                 200                 205 aac gtc cag gca cag gct gtg tgt ggg ccg ctg ttc gtc atc gac cat    672
Asn Val Gln Ala Gln Ala Val Cys Gly Pro Leu Phe Val Ile Asp His
    210                 215                 220 gca ggc tcg ctc acc tcg cag ttc tcc tac gtc gtc ggt cga tcc gcc    720
Ala Gly Ser Leu Thr Ser Gln Phe Ser Tyr Val Val Gly Arg Ser Ala
225                 230                 235                 240 ctg cgc tcc acc acg ggc cag gct cgt agt gca gac tat ggc att acg    768
Leu Arg Ser Thr Thr Gly Gln Ala Arg Ser Ala Asp Tyr Gly Ile Thr
                245                 250                 255 gac tgc aac cct ctt ccc gcc aat gat ctg act ccc gag caa aag gtc    816
Asp Cys Asn Pro Leu Pro Ala Asn Asp Leu Thr Pro Glu Gln Lys Val
            260                 265                 270 gcc gcg gct gcg ctc ctg gcg ccg gcg gct gca gcc atc gtg gcg ggt    864
Ala Ala Ala Ala Leu Leu Ala Pro Ala Ala Ala Ile Val Ala Gly
        275                 280                 285 cca aag cag aac tgc gag ccc gac ctc atg ccc tac gcc cgc ccc ttt    912
Pro Lys Gln Asn Cys Glu Pro Asp Leu Met Pro Tyr Ala Arg Pro Phe
    290                 295                 300 gca gta ggc aaa agg acc tgc tcc ggc atc gtc acc ccc tga              954
Ala Val Gly Lys Arg Thr Cys Ser Gly Ile Val Thr Pro
305                 310                 315

<210> SEQ ID NO 2
<211> LENGTH: 317
<212> TYPE: PRT
<213> ORGANISM: Candida antarctica

<400> SEQUENCE: 2

Leu Pro Ser Gly Ser Asp Pro Ala Phe Ser Gln Pro Lys Ser Val Leu
1               5                   10                  15

Asp Ala Gly Leu Thr Cys Gln Gly Ala Ser Pro Ser Ser Val Ser Lys
                20                  25                  30

Pro Ile Leu Leu Val Pro Gly Thr Gly Thr Thr Gly Pro Gln Ser Phe
            35                  40                  45

Asp Ser Asn Trp Ile Pro Leu Ser Ala Gln Leu Gly Tyr Thr Pro Cys
        50                  55                  60

Trp Ile Ser Pro Pro Pro Phe Met Leu Asn Asp Thr Gln Val Asn Thr
65                  70                  75                  80

Glu Tyr Met Val Asn Ala Ile Thr Thr Leu Tyr Ala Gly Ser Gly Asn
                85                  90                  95

Asn Lys Leu Pro Val Leu Thr Trp Ser Gln Gly Gly Leu Val Ala Gln
            100                 105                 110

Trp Gly Leu Thr Phe Phe Pro Ser Ile Arg Ser Lys Val Asp Arg Leu
        115                 120                 125

Met Ala Phe Ala Pro Asp Tyr Lys Gly Thr Val Leu Ala Gly Pro Leu
    130                 135                 140

Asp Ala Leu Ala Val Ser Ala Pro Ser Val Trp Gln Gln Thr Thr Gly
145                 150                 155                 160
```

-continued

```
Ser Ala Leu Thr Thr Ala Leu Arg Asn Ala Gly Gly Leu Thr Gln Ile
                165                 170                 175

Val Pro Thr Thr Asn Leu Tyr Ser Ala Thr Asp Glu Ile Val Gln Pro
            180                 185                 190

Gln Val Ser Asn Ser Pro Leu Asp Ser Ser Tyr Leu Phe Asn Gly Lys
        195                 200                 205

Asn Val Gln Ala Gln Ala Val Cys Gly Pro Leu Phe Val Ile Asp His
    210                 215                 220

Ala Gly Ser Leu Thr Ser Gln Phe Ser Tyr Val Val Gly Arg Ser Ala
225                 230                 235                 240

Leu Arg Ser Thr Thr Gly Gln Ala Arg Ser Ala Asp Tyr Gly Ile Thr
                245                 250                 255

Asp Cys Asn Pro Leu Pro Ala Asn Asp Leu Thr Pro Glu Gln Lys Val
            260                 265                 270

Ala Ala Ala Ala Leu Leu Ala Pro Ala Ala Ala Ile Val Ala Gly
        275                 280                 285

Pro Lys Gln Asn Cys Glu Pro Asp Leu Met Pro Tyr Ala Arg Pro Phe
    290                 295                 300

Ala Val Gly Lys Arg Thr Cys Ser Gly Ile Val Thr Pro
305                 310                 315

<210> SEQ ID NO 3
<211> LENGTH: 408
<212> TYPE: PRT
<213> ORGANISM: Artificial Sequence
<220> FEATURE:
<223> OTHER INFORMATION: T40 Mutant with alpha-factor
<220> FEATURE:
<221> NAME/KEY: SIGNAL
<222> LOCATION: (1)..(91)
<223> OTHER INFORMATION: alpha factor
<220> FEATURE:
<221> NAME/KEY: MISC_FEATURE
<222> LOCATION: (131)..(131)
<223> OTHER INFORMATION: Xaa is matated, in particular Ala, Val or Ser
<220> FEATURE:
<221> NAME/KEY: MISC_FEATURE
<222> LOCATION: (131)..(131)
<223> OTHER INFORMATION: Xaa is mutated, in particular Ala, Val or Ser

<400> SEQUENCE: 3

Met Arg Phe Pro Ser Ile Phe Thr Ala Val Leu Phe Ala Ala Ser Ser
1               5                   10                  15

Ala Leu Ala Ala Pro Val Asn Thr Thr Thr Glu Asp Glu Thr Ala Gln
            20                  25                  30

Ile Pro Ala Glu Ala Val Ile Gly Tyr Ser Asp Leu Glu Gly Asp Phe
        35                  40                  45

Asp Val Ala Val Leu Pro Phe Ser Asn Ser Thr Asn Asn Gly Leu Leu
    50                  55                  60

Phe Ile Asn Thr Thr Ile Ala Ser Ile Ala Ala Lys Glu Glu Gly Val
65                  70                  75                  80

Ser Leu Glu Lys Arg Glu Ala Glu Ala Glu Phe Leu Pro Ser Gly Ser
                85                  90                  95

Asp Pro Ala Phe Ser Gln Pro Lys Ser Val Leu Asp Ala Gly Leu Thr
            100                 105                 110

Cys Gln Gly Ala Ser Pro Ser Ser Val Ser Lys Pro Ile Leu Leu Val
        115                 120                 125

Pro Gly Xaa Gly Thr Thr Gly Pro Gln Ser Phe Asp Ser Asn Trp Ile
    130                 135                 140
```

-continued

```
Pro Leu Ser Ala Gln Leu Gly Tyr Thr Pro Cys Trp Ile Ser Pro Pro
145                 150                 155                 160

Pro Phe Met Leu Asn Asp Thr Gln Val Asn Thr Glu Tyr Met Val Asn
                165                 170                 175

Ala Ile Thr Thr Leu Tyr Ala Gly Ser Gly Asn Asn Lys Leu Pro Val
            180                 185                 190

Leu Thr Trp Ser Gln Gly Gly Leu Val Ala Gln Trp Gly Leu Thr Phe
        195                 200                 205

Phe Pro Ser Ile Arg Ser Lys Val Asp Arg Leu Met Ala Phe Ala Pro
    210                 215                 220

Asp Tyr Lys Gly Thr Val Leu Ala Gly Pro Leu Asp Ala Leu Ala Val
225                 230                 235                 240

Ser Ala Pro Ser Val Trp Gln Gln Thr Thr Gly Ser Ala Leu Thr Thr
                245                 250                 255

Ala Leu Arg Asn Ala Gly Gly Leu Thr Gln Ile Val Pro Thr Thr Asn
            260                 265                 270

Leu Tyr Ser Ala Thr Asp Glu Ile Val Gln Pro Gln Val Ser Asn Ser
        275                 280                 285

Pro Leu Asp Ser Ser Tyr Leu Phe Asn Gly Lys Asn Val Gln Ala Gln
    290                 295                 300

Ala Val Cys Gly Pro Leu Phe Val Ile Asp His Ala Gly Ser Leu Thr
305                 310                 315                 320

Ser Gln Phe Ser Tyr Val Val Gly Arg Ser Ala Leu Arg Ser Thr Thr
                325                 330                 335

Gly Gln Ala Arg Ser Ala Asp Tyr Gly Ile Thr Asp Cys Asn Pro Leu
            340                 345                 350

Pro Ala Asn Asp Leu Thr Pro Glu Gln Lys Val Ala Ala Ala Leu
        355                 360                 365

Leu Ala Pro Ala Ala Ala Ile Val Ala Gly Pro Lys Gln Asn Cys
    370                 375                 380

Glu Pro Asp Leu Met Pro Tyr Ala Arg Pro Phe Ala Val Gly Lys Arg
385                 390                 395                 400

Thr Cys Ser Gly Ile Val Thr Pro
                405
```

<210> SEQ ID NO 4
<211> LENGTH: 317
<212> TYPE: PRT
<213> ORGANISM: Artificial Sequence
<220> FEATURE:
<223> OTHER INFORMATION: T40 Mutant
<220> FEATURE:
<221> NAME/KEY: MISC_FEATURE
<222> LOCATION: (40)..(40)
<223> OTHER INFORMATION: Xaa is mutated, in particular Ala, Val or Ser

<400> SEQUENCE: 4

```
Leu Pro Ser Gly Ser Asp Pro Ala Phe Ser Gln Pro Lys Ser Val Leu
1               5                   10                  15

Asp Ala Gly Leu Thr Cys Gln Gly Ala Ser Pro Ser Val Ser Lys
            20                  25                  30

Pro Ile Leu Leu Val Pro Gly Xaa Gly Thr Thr Gly Pro Gln Ser Phe
        35                  40                  45

Asp Ser Asn Trp Ile Pro Leu Ser Ala Gln Leu Gly Tyr Thr Pro Cys
    50                  55                  60

Trp Ile Ser Pro Pro Pro Phe Met Leu Asn Asp Thr Gln Val Asn Thr
65                  70                  75                  80
```

```
Glu Tyr Met Val Asn Ala Ile Thr Thr Leu Tyr Ala Gly Ser Gly Asn
                85                  90                  95
Asn Lys Leu Pro Val Leu Thr Trp Ser Gln Gly Gly Leu Val Ala Gln
            100                 105                 110
Trp Gly Leu Thr Phe Phe Pro Ser Ile Arg Ser Lys Val Asp Arg Leu
        115                 120                 125
Met Ala Phe Ala Pro Asp Tyr Lys Gly Thr Val Leu Ala Gly Pro Leu
    130                 135                 140
Asp Ala Leu Ala Val Ser Ala Pro Ser Val Trp Gln Gln Thr Thr Gly
145                 150                 155                 160
Ser Ala Leu Thr Thr Ala Leu Arg Asn Ala Gly Gly Leu Thr Gln Ile
                165                 170                 175
Val Pro Thr Thr Asn Leu Tyr Ser Ala Thr Asp Glu Ile Val Gln Pro
            180                 185                 190
Gln Val Ser Asn Ser Pro Leu Asp Ser Ser Tyr Leu Phe Asn Gly Lys
        195                 200                 205
Asn Val Gln Ala Gln Ala Val Cys Gly Pro Leu Phe Val Ile Asp His
    210                 215                 220
Ala Gly Ser Leu Thr Ser Gln Phe Ser Tyr Val Val Gly Arg Ser Ala
225                 230                 235                 240
Leu Arg Ser Thr Thr Gly Gln Ala Arg Ser Ala Asp Tyr Gly Ile Thr
                245                 250                 255
Asp Cys Asn Pro Leu Pro Ala Asn Asp Leu Thr Pro Glu Gln Lys Val
            260                 265                 270
Ala Ala Ala Ala Leu Leu Ala Pro Ala Ala Ala Ile Val Ala Gly
        275                 280                 285
Pro Lys Gln Asn Cys Glu Pro Asp Leu Met Pro Tyr Ala Arg Pro Phe
    290                 295                 300
Ala Val Gly Lys Arg Thr Cys Ser Gly Ile Val Thr Pro
305                 310                 315

<210> SEQ ID NO 5
<211> LENGTH: 21
<212> TYPE: DNA
<213> ORGANISM: Artificial Sequence
<220> FEATURE:
<223> OTHER INFORMATION: PCR Primer

<400> SEQUENCE: 5
gactggttcc aattgacaag c                                         21

<210> SEQ ID NO 6
<211> LENGTH: 21
<212> TYPE: DNA
<213> ORGANISM: Artificial Sequence
<220> FEATURE:
<223> OTHER INFORMATION: PCR Primer

<400> SEQUENCE: 6
gcaaatggca ttctgacatc c                                         21

<210> SEQ ID NO 7
<211> LENGTH: 39
<212> TYPE: DNA
<213> ORGANISM: Artificial Sequence
<220> FEATURE:
<223> OTHER INFORMATION: PCR Primer

<400> SEQUENCE: 7
cccatccttc tcgtccccgg agtcggcacc acaggtcca                      39
```

<210> SEQ ID NO 8
<211> LENGTH: 39
<212> TYPE: DNA
<213> ORGANISM: Artificial Sequence
<220> FEATURE:
<223> OTHER INFORMATION: PCR Primer

<400> SEQUENCE: 8
gtcgaacgac tgtggacctg tggtgccgac tccggggac                                    39

<210> SEQ ID NO 9
<211> LENGTH: 22
<212> TYPE: DNA
<213> ORGANISM: Artificial Sequence
<220> FEATURE:
<223> OTHER INFORMATION: Primer

<400> SEQUENCE: 9
cctggcgccg gcattggcag cc                                                      22

<210> SEQ ID NO 10
<211> LENGTH: 22
<212> TYPE: DNA
<213> ORGANISM: Artificial Sequence
<220> FEATURE:
<223> OTHER INFORMATION: Primer

<400> SEQUENCE: 10
ggctgccaat gccggcgcca gg                                                      22

<210> SEQ ID NO 11
<211> LENGTH: 23
<212> TYPE: DNA
<213> ORGANISM: Artificial Sequence
<220> FEATURE:
<223> OTHER INFORMATION: Generic forward primer for mutating position
      282
<220> FEATURE:
<221> NAME/KEY: misc_feature
<222> LOCATION: (13)..(15)
<223> OTHER INFORMATION: N represents any of A, T, G or C

<400> SEQUENCE: 11
ctggcgccgg cgnnngcagc cat                                                     23

<210> SEQ ID NO 12
<211> LENGTH: 23
<212> TYPE: DNA
<213> ORGANISM: Artificial Sequence
<220> FEATURE:
<223> OTHER INFORMATION: Generic reverse primer for mutating position
      282
<220> FEATURE:
<221> NAME/KEY: misc_feature
<222> LOCATION: (9)..(11)
<223> OTHER INFORMATION: N represents any of A, T, C or G

<400> SEQUENCE: 12
atggctgcnn ncgccggcgc cag                                                     23

<210> SEQ ID NO 13
<211> LENGTH: 15
<212> TYPE: DNA
<213> ORGANISM: Artificial Sequence
<220> FEATURE:
<223> OTHER INFORMATION: Forward primer for I285F mutation

<400> SEQUENCE: 13

```
gcagcctttg tggcg                                                      15

<210> SEQ ID NO 14
<211> LENGTH: 15
<212> TYPE: DNA
<213> ORGANISM: Artificial Sequence
<220> FEATURE:
<223> OTHER INFORMATION: Reverse primer for I285F mutation

<400> SEQUENCE: 14
cgccacaaag gctgc                                                      15

<210> SEQ ID NO 15
<211> LENGTH: 33
<212> TYPE: DNA
<213> ORGANISM: Artificial Sequence
<220> FEATURE:
<223> OTHER INFORMATION: Forward primer for A282/I285F mutation

<400> SEQUENCE: 15
ccggcgcttg cagcctttgt ggcgggtcca aag                                  33

<210> SEQ ID NO 16
<211> LENGTH: 33
<212> TYPE: DNA
<213> ORGANISM: Artificial Sequence
<220> FEATURE:
<223> OTHER INFORMATION: Reverse primer for A282L/I285F mutation

<400> SEQUENCE: 16
ctttggaccc gccacaaagg ctgcaagcgc cgg                                  33

<210> SEQ ID NO 17
<211> LENGTH: 15
<212> TYPE: DNA
<213> ORGANISM: Artificial Sequence
<220> FEATURE:
<223> OTHER INFORMATION: Forward primer for L278S mutation

<400> SEQUENCE: 17
gctctctgcg ccggc                                                      15

<210> SEQ ID NO 18
<211> LENGTH: 15
<212> TYPE: DNA
<213> ORGANISM: Artificial Sequence
<220> FEATURE:
<223> OTHER INFORMATION: Reverse primer for L278S mutation

<400> SEQUENCE: 18
gccggcgcag cgacg                                                      15

<210> SEQ ID NO 19
<211> LENGTH: 27
<212> TYPE: DNA
<213> ORGANISM: Artificial Sequence
<220> FEATURE:
<223> OTHER INFORMATION: Forward primer for A281V mutation

<400> SEQUENCE: 19
cggctgcgct cctggctcct gtagctg                                         27

<210> SEQ ID NO 20
<211> LENGTH: 27
<212> TYPE: DNA
<213> ORGANISM: Artificial Sequence
```

```
<220> FEATURE:
<223> OTHER INFORMATION: Reverse primer for A281V mutation

<400> SEQUENCE: 20
ctgcagctac aggagccagg agcgcag                                    27

<210> SEQ ID NO 21
<211> LENGTH: 27
<212> TYPE: DNA
<213> ORGANISM: Artificial Sequence
<220> FEATURE:
<223> OTHER INFORMATION: Forward primer for A281E mutation

<400> SEQUENCE: 21
cggctgcgct cctggctcct gaggctg                                    27

<210> SEQ ID NO 22
<211> LENGTH: 27
<212> TYPE: DNA
<213> ORGANISM: Artificial Sequence
<220> FEATURE:
<223> OTHER INFORMATION: Reverse primer for A281E mutation

<400> SEQUENCE: 22
cagcctcagg agccaggagc gcagccg                                    27
```

The invention claimed is:

1. A biocatalytic method of preparing a mono-acylated polyol of the general formula (I):

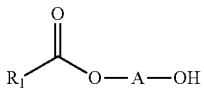

wherein
R₁ represents an optionally substituted, linear or branched, saturated or non-saturated hydrocarbyl residue; and
A represents an optionally substituted, linear or branched hydrocarbylene residue having at least two carbon atoms,
which method comprises
a) reacting a polyol of the formula (II) and an acyl donor compound of the formula (III)

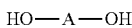

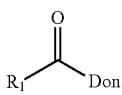

wherein R₁ and A are as defined above, and
Don represents a donor molecule residue carrying the said acyl group;
in the presence of a mutated triacylglycerole lipase (EC 3.1.1.3) until a mono-acylated polyol of the above formula (I) is formed; and
b) obtaining a monoacylated polyol product
wherein said lipase is a mutant of *Candida antarctica* lipase B (CALB) comprising an amino acid sequence of SEQ ID NO: 2, mutated in at least one position and up to fifteen positions; wherein the amino acid comprises a mutation in position Thr40.

2. The method of claim 1, wherein said mutated lipase contains at least one amino acid mutation, which increases the selectivity of the lipase for the mono-acylation of said polyol, if compared to the corresponding non-mutated lipase.

3. The method of claim 1, wherein said mutant comprises at least one mutation, which removes a stabilizing functional amino acid from that part of the reactive center of the enzyme which stabilizes an oxyanion transition state of the carbonyl group of the mono-acylated polyol of formula (I) to be formed.

4. The method of claim 1, wherein
a) a maximum monoester yield is obtained which is at last 1% above the maximum yield as obtained by the corresponding wild-type enzyme;
b) a 3:1 molar ratio of monoester to polyester is reached at a conversion rate of the polyol which is at last 1% above the corresponding conversion rate as obtained by the corresponding wild-type enzyme; and/or
c) the ratio of reaction times ($T_{90}$(mutant)/$T_{90}$(wild-type)) to reach 90% monoacylated polyol based on the total amount of polyol is above 1.

5. The method of claim 1, wherein the mutation is such that substantially no stabilizing interaction between the oxyanion intermediate and the amino acid residue in position 40 occurs.

6. The method of claim 5 wherein the mutation comprises the single mutations Thr40Ala, Thr40Val or Thr40Ser.

7. The method of claim 6, wherein said mutant is selected from mutants having an amino acid sequence of SEQ ID NO: 4 or variants of said mutant having a sequence identity of at least 60%, which variants still contain a mutation in an amino acid position corresponding to position Thr40 of SEQ ID NO:4.

8. The method of claim 5, wherein the mutant additionally comprises at least one mutation in one of the amino acid positions Leu 278, Ile 285 and Pro 280 of SEQ ID NO: 2 or 4.

9. The method of claim 8, wherein the mutants and the variants thereof are not mutated in other amino acid positions contributing to the catalytic site of the enzyme.

10. The method of claim 9, wherein the mutants are not mutated in amino acid positions Ser105, Asp187, His224 (catalytic triade) and Gln106 and wherein the variants are not mutated in amino acid positions corresponding thereto.

11. The method of claim 1, wherein in SEQ ID NO:2, or in SEQ ID NO:2 comprising a mutation at amino acid Thr40 according to SEQ ID NO:4, one or more of Leu278, Ala281, Ala282 or Ile285 are mutated.

12. The method of claim 11, wherein the one or more mutations are independently selected from Leu278Ser, Ala281Val or Ala281Glu, and Ala282Leu, Ala282Thr, Ala282Cys, Ala282Pro, Ala282Ile, Ala282Asp, Ala282Val, Ala282Met or Ala282Arg.

13. The method of claim 12, wherein SEQ ID NO:2 comprises one mutation, selected from Ala281Val, Ala281Glu, Ala282Leu, Ala282Thr, Ala282Cys, Ala282Pro, Ala282Ile, Ala282Asp, Ala282Val, Ala282Met, Ala282Arg and Ile285Phe, or wherein SEQ ID NO:2 comprises the double mutation Leu278Ser and Ala282Leu.

14. The method of claim 1, wherein the reaction is performed in the presence of the isolated enzyme mutant or a recombinant microorganism functionally expressing said mutant.

15. The method of claim 1, wherein the polyol is a compound of formula (II) wherein A is selected from the groups —$(CH_2)_n$— and —$(CH_2)_m$—, —$CR_2R_3$—$(CH_2)_{m'}$—
wherein
n is an integer of 2-6,
m and m' independently of each other are integers of 1-3
$R_2$ and $R_3$ independently of each other are selected from H, OH, SH, $NH_2$, optionally substituted carbo- or heterocyclic rings and hydrocarbyl-residues, provided that $R_2$ and
$R_3$ are not simultaneously H.

16. The method of claim 1, wherein the donor of formula (III) is selected from compounds wherein R1 is C1-C6-alkyl and Don is an —OR residue, wherein R is selected from C1-C6-alkyl and C2-C4-alkenyl.

17. An enzymatically catalyzed method of enantioselectively preparing an asymmetric mono-acylated polyol of the general formula (I):

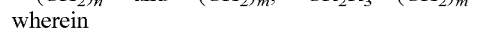
(I')

wherein
$R_1$ represents an optionally substituted, linear or branched, saturated or non-saturated hydrocarbyl residue; and
A* represents an optionally substituted, linear or branched, asymmetric hydrocarbylene residue having at least two carbon atoms;
which method comprises
a) reacting a stereoisomeric mixture of a polyol of the formula (II') and an acyl donor compound of the formula (III)

HO—A*—OH (II')

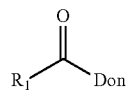
(III)

wherein $R_1$ and A* are as defined above, and
Don represents a donor molecule residue carrying the said acyl group;
in the presence of a mutated triacylglycerole lipase (EC 3.1.1.3) until a mono-acylated polyol of the above formula (I) is formed; and
b) obtaining an asymmetric monoacylated polyol product; wherein said lipase is a mutant of *Candida antarctica* lipase B (CALB) comprising an amino acid sequence of SEQ ID NO: 2, mutated in at least one position and up to fifteen positions; wherein the amino acid comprises a mutation in position Thr40.

18. The method of claim 17 wherein an enzyme mutant said mutated lipase contains at least one amino acid mutation, which increases the selectivity of the lipase for the monoacylation of said polyol, if compared to the corresponding non-mutated lipase in the form of an isolated enzyme mutant or a recombinant microorganism functionally expressing said mutant is applied.

19. The method of claim 17, wherein the polyol is a compound of formula (II') wherein A* is selected from the groups —$(CH_2)_m$—$CHR_2$—$(CH_2)_{m'}$— wherein m, m' and $R_2$ are as defined above.

20. The method of claim 1, wherein the lipase is a mutant of *Candida antarctica* lipase B (CALB) comprising an amino acid sequence of SEQ ID NO: 2, mutated in at least two positions, the mutations being selected from the group consisting of

| Thr40 | Leu278 | Ile285 | Pro280 |
|---|---|---|---|
| | 2-fold mutants | | |
| Ala | Phe | | |
| Ala | Trp | | |
| Ala | Ala | | |
| Ala | Ser | | |
| Ala | Asn | | |
| Ala | | Leu | |
| Ala | | Ser | |
| Ala | | Phe | |
| Ala | | Gln | |
| Ala | | | Ala |
| Val | Phe | | |
| Val | Trp | | |
| Val | Ala | | |
| Val | Ser | | |
| Val | Asn | | |
| Val | | Leu | |
| Val | | Ser | |
| Val | | Phe | |
| Val | | Gln | |
| Val | | | Ala |
| Ser | Trp | | |
| Ser | Ala | | |
| Ser | Ser | | |
| Ser | Asn | | |
| Ser | | Leu | |
| Ser | | Ser | |
| Ser | | Phe | |
| Ser | | Gln | |
| Ser | | | Ala |

-continued

| Thr40 | Leu278 | Ile285 | Pro280 |
|---|---|---|---|
| 3-fold mutants ||||
| Ala | Phe | Leu | |
| Ala | Phe | Ser | |
| Ala | Phe | Phe | |
| Ala | Phe | Gln | |
| Ala | Phe | | Ala |
| Ala | Trp | Leu | |
| Ala | Trp | Ser | |
| Ala | Trp | Phe | |
| Ala | Trp | Gln | |
| Ala | Trp | | Ala |
| Ala | Ala | Leu | |
| Ala | Ala | Ser | |
| Ala | Ala | Phe | |
| Ala | Ala | Gln | |
| Ala | Ala | | Ala |
| Ala | Ser | Leu | |
| Ala | Ser | Ser | |
| Ala | Ser | Phe | |
| Ala | Ser | Gln | |
| Ala | Ser | | Ala |
| Ala | Asn | Leu | |
| Ala | Asn | Ser | |
| Ala | Asn | Phe | |
| Ala | Asn | Gln | |
| Ala | Asn | | Ala |
| Val | Phe | Leu | |
| Val | Phe | Ser | |
| Val | Phe | Phe | |
| Val | Phe | Gln | |
| Val | Phe | | Ala |
| Val | Trp | Leu | |
| Val | Trp | Ser | |
| Val | Trp | Phe | |
| Val | Trp | Gln | |
| Val | Trp | | Ala |
| Val | Ala | Leu | |
| Val | Ala | Ser | |
| Val | Ala | Phe | |
| Val | Ala | Gln | |
| Val | Ala | | Ala |
| Val | Ser | Leu | |
| Val | Ser | Ser | |
| Val | Ser | Phe | |
| Val | Ser | Gln | |
| Val | Ser | | Ala |
| Val | Asn | Leu | |
| Val | Asn | Ser | |
| Val | Asn | Phe | |
| Val | Asn | Gln | |
| Val | Asn | | Ala |
| Ser | Phe | Leu | |
| Ser | Phe | Ser | |
| Ser | Phe | Phe | |
| Ser | Phe | Gln | |
| Ser | Phe | | Ala |
| Ser | Trp | Leu | |
| Ser | Trp | Ser | |
| Ser | Trp | Phe | |
| Ser | Trp | Gln | |
| Ser | Trp | | Ala |
| Ser | Ala | Leu | |
| Ser | Ala | Ser | |
| Ser | Ala | Phe | |
| Ser | Ala | Gln | |
| Ser | Ala | | Ala |
| Ser | Ser | Leu | |
| Ser | Ser | Ser | |
| Ser | Ser | Phe | |
| Ser | Ser | Gln | |
| Ser | Ser | | Ala |
| Ser | Asn | Leu | |
| Ser | Asn | Set | |
| Ser | Asn | Phe | |
| Ser | Asn | Gln | |
| Set | Asn | | Ala |
| and 4-fold mutants ||||
| Ala | Phe | Leu | Ala |
| Ala | Phe | Ser | Ala |
| Ala | Phe | Phe | Ala |
| Ala | Phe | Gln | Ala |
| Ala | Trp | Leu | Ala |
| Ala | Trp | Ser | Ala |
| Ala | Trp | Phe | Ala |
| Ala | Trp | Gln | Ala |
| Ala | Ala | Leu | Ala |
| Ala | Ala | Ser | Ala |
| Ala | Ala | Phe | Ala |
| Ala | Ala | Gln | Ala |
| Ala | Set | Leu | Ala |
| Ala | Ser | Ser | Ala |
| Ala | Ser | Phe | Ala |
| Ala | Ser | Gln | Ala |
| Ala | Asn | Leu | Ala |
| Ala | Asn | Set | Ala |
| Ala | Asn | Phe | Ala |
| Ala | Asn | Gln | Ala |
| Val | Phe | Leu | Ala |
| Val | Phe | Set | Ala |
| Val | Phe | Phe | Ala |
| Val | Phe | Gln | Ala |
| Val | Trp | Leu | Ala |
| Val | Trp | Set | Ala |
| Val | Trp | Phe | Ala |
| Val | Trp | Gln | Ala |
| Val | Ala | Leu | Ala |
| Val | Ala | Ser | Ala |
| Val | Ala | Phe | Ala |
| Val | Ala | Gln | Ala |
| Val | Ser | Leu | Ala |
| Val | Ser | Set | Ala |
| Val | Ser | Phe | Ala |
| Val | Ser | Gln | Ala |
| Val | Asn | Leu | Ala |
| Val | Asn | Ser | Ala |
| Val | Asn | Phe | Ala |
| Val | Asn | Gln | Ala |
| Ser | Phe | Leu | Ala |
| Ser | Phe | Ser | Ala |
| Ser | Phe | Phe | Ala |
| Ser | Phe | Gln | Ala |
| Ser | Trp | Leu | Ala |
| Ser | Trp | Ser | Ala |
| Ser | Trp | Phe | Ala |
| Ser | Trp | Gln | Ala |
| Ser | Ala | Leu | Ala |
| Ser | Ala | Ser | Ala |
| Ser | Ala | Phe | Ala |
| Ser | Ala | Gln | Ala |
| Ser | Ser | Leu | Ala |
| Ser | Ser | Ser | Ala |
| Ser | Ser | Phe | Ala |
| Ser | Ser | Gln | Ala |
| Ser | Asn | Leu | Ala |
| Ser | Asn | Ser | Ala |
| Ser | Asn | Phe | Ala |
| Ser | Asn | Gln | Ala. |

* * * * *